(12) United States Patent
Short

(10) Patent No.: US 10,513,699 B2
(45) Date of Patent: Dec. 24, 2019

(54) DISCOVERING AND PRODUCING CONDITIONALLY ACTIVE BIOLOGIC PROTEINS IN THE SAME EUKARYOTIC CELL PRODUCTION HOSTS

(71) Applicant: BioAtla, LLC, San Diego, CA (US)

(72) Inventor: Jay M. Short, Del Mar, CA (US)

(73) Assignee: BioAtla, LLC, San Diego, CA (US)

( * ) Notice: Subject to any disclaimer, the term of this patent is extended or adjusted under 35 U.S.C. 154(b) by 48 days.

(21) Appl. No.: 15/329,491

(22) PCT Filed: Sep. 3, 2015

(86) PCT No.: PCT/US2015/048258
§ 371 (c)(1),
(2) Date: Aug. 29, 2017

(87) PCT Pub. No.: WO2016/036916
PCT Pub. Date: Mar. 10, 2016

(65) Prior Publication Data
US 2017/0247685 A1  Aug. 31, 2017

Related U.S. Application Data

(60) Provisional application No. 62/045,207, filed on Sep. 3, 2014.

(51) Int. Cl.
| | | |
|---|---|---|
| C12N 15/10 | (2006.01) |
| G01N 33/68 | (2006.01) |
| C12Q 1/6811 | (2018.01) |
| C07K 16/46 | (2006.01) |
| C12N 15/80 | (2006.01) |
| C07K 16/00 | (2006.01) |
| C07K 14/435 | (2006.01) |
| C12P 21/00 | (2006.01) |

(52) U.S. Cl.
CPC ........ *C12N 15/1058* (2013.01); *C07K 14/435* (2013.01); *C07K 16/00* (2013.01); *C07K 16/46* (2013.01); *C12N 15/80* (2013.01); *C12P 21/00* (2013.01); *C07K 2317/14* (2013.01); *C07K 2317/31* (2013.01); *C07K 2317/52* (2013.01); *C07K 2317/622* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,318,905 A | 3/1982 | Nestor et al. |
| 4,676,980 A | 6/1987 | Segal et al. |
| 4,683,195 A | 7/1987 | Mullis et al. |
| 4,683,202 A | 7/1987 | Mullis |
| 4,704,362 A | 11/1987 | Itakura et al. |
| 4,777,127 A | 10/1988 | Suni et al. |
| 4,797,368 A | 1/1989 | Carter et al. |
| 4,800,189 A | 1/1989 | Eschwey et al. |
| 4,883,750 A | 11/1989 | Whiteley et al. |
| 4,946,778 A | 8/1990 | Ladner et al. |
| 5,112,946 A | 5/1992 | Maione |
| 5,139,941 A | 8/1992 | Muzyczka et al. |
| 5,143,854 A | 9/1992 | Pirrung et al. |
| 5,219,740 A | 6/1993 | Miller et al. |
| 5,336,603 A | 8/1994 | Capon et al. |
| 5,349,053 A | 9/1994 | Landofi |
| 5,359,046 A | 10/1994 | Capon et al. |
| 5,434,049 A | 7/1995 | Okano et al. |
| 5,447,851 A | 9/1995 | Beutler et al. |
| 5,556,752 A | 9/1996 | Lockhart et al. |
| 5,622,929 A | 4/1997 | Willner et al. |
| 5,632,957 A | 5/1997 | Heller et al. |
| 5,641,870 A | 6/1997 | Rinderknecht et al. |

(Continued)

FOREIGN PATENT DOCUMENTS

| | | |
|---|---|---|
| EP | 0320308 A2 | 6/1989 |
| EP | 345242 A2 | 12/1989 |

(Continued)

OTHER PUBLICATIONS

Chilean Office Action; dated Oct. 16, 2018 for CL Application No. 201700528.

(Continued)

*Primary Examiner* — Channing S Mahatan
(74) *Attorney, Agent, or Firm* — Mendelsohn Dunleavy, P.C.

(57) ABSTRACT

A method of preparing a conditionally active biologic protein by selecting a wild-type biologic protein, evolving the DNA which encodes the wild-type biologic protein using one or more evolutionary techniques to create mutant DNAs, expressing the mutant DNAs in a eukaryotic cell production host to obtain a mutant protein, subjecting the mutant protein and the wild-type protein to an assay under a normal physiological condition and to an assay under an aberrant condition, selecting a conditionally active mutant protein which exhibits at least one of: (a) a decrease in activity in the assay at the normal physiological condition compared to the wild-type protein, and (b) an increase in activity in the assay under the aberrant condition compared to the wild-type protein; and producing the conditionally active biologic protein in the same eukaryotic cell production host used in the expression step.

25 Claims, 7 Drawing Sheets
(6 of 7 Drawing Sheet(s) Filed in Color)

(56) References Cited

U.S. PATENT DOCUMENTS

| | | | |
|---|---|---|---|
| 5,723,125 | A | 3/1998 | Chang et al. |
| 5,744,305 | A | 4/1998 | Fodor et al. |
| 5,770,456 | A | 6/1998 | Holmes |
| 5,783,181 | A | 7/1998 | Browne et al. |
| 5,800,992 | A | 9/1998 | Fodor et al. |
| 5,807,522 | A | 9/1998 | Brown et al. |
| 5,830,645 | A | 11/1998 | Pinkel et al. |
| 5,844,095 | A | 12/1998 | Linsley et al. |
| 5,856,174 | A | 1/1999 | Lipshutz et al. |
| 5,908,626 | A | 6/1999 | Chang et al. |
| 5,959,098 | A | 9/1999 | Goldberg et al. |
| 5,965,452 | A | 10/1999 | Kovacs |
| 5,994,136 | A | 11/1999 | Naldini et al. |
| 6,013,440 | A | 1/2000 | Lipshutz et al. |
| 6,013,516 | A | 1/2000 | Verma et al. |
| 6,022,963 | A | 2/2000 | McGall et al. |
| 6,045,996 | A | 4/2000 | Cronin et al. |
| 6,048,695 | A | 4/2000 | Bradley et al. |
| 6,258,606 | B1 | 7/2001 | Kovacs |
| 6,262,776 | B1 | 7/2001 | Pirrung et al. |
| 6,277,628 | B1 | 8/2001 | Johann et al. |
| 7,045,337 | B2 | 5/2006 | Schultz et al. |
| 8,362,210 | B2 * | 1/2013 | Lazar ............... C07K 16/2803 424/130.1 |
| 2001/0008765 | A1 | 7/2001 | Shinoki et al. |
| 2001/0012537 | A1 | 8/2001 | Anderson et al. |
| 2001/0014448 | A1 | 8/2001 | Chappa et al. |
| 2001/0014449 | A1 | 8/2001 | Nerenberg et al. |
| 2001/0016322 | A1 | 8/2001 | Caren et al. |
| 2001/0018642 | A1 | 8/2001 | Balaban et al. |
| 2001/0019827 | A1 | 9/2001 | Dawson et al. |
| 2005/0100985 | A1 | 5/2005 | Short |
| 2007/0009930 | A1 | 1/2007 | Patten et al. |
| 2009/0130718 | A1 | 5/2009 | Short |
| 2010/0256340 | A1 | 10/2010 | Brinkmann et al. |
| 2010/0260739 | A1 | 10/2010 | Short et al. |
| 2012/0165201 | A1 | 6/2012 | Short |
| 2012/0245036 | A1 | 9/2012 | Short |
| 2013/0281303 | A1 | 10/2013 | Short |
| 2017/0191055 | A1 * | 7/2017 | Short ................ C12N 15/09 |

FOREIGN PATENT DOCUMENTS

| | | |
|---|---|---|
| EP | 0367166 A1 | 5/1990 |
| EP | 0394827 A1 | 10/1990 |
| GB | 2200651 A | 8/1988 |
| WO | WO8706270 A1 | 10/1987 |
| WO | WO8807089 A1 | 9/1988 |
| WO | WO8909284 A1 | 10/1989 |
| WO | WO9007936 A1 | 7/1990 |
| WO | WO9102805 A2 | 3/1991 |
| WO | WO9106570 A1 | 5/1991 |
| WO | WO9303769 A1 | 3/1992 |
| WO | WO9301919 A1 | 2/1993 |
| WO | WO9308829 A1 | 5/1993 |
| WO | WO9310218 A1 | 5/1993 |
| WO | WO9311230 A1 | 6/1993 |
| WO | WO9325234 A1 | 12/1993 |
| WO | WO9325698 A1 | 12/1993 |
| WO | WO9403622 A1 | 2/1994 |
| WO | WO9412649 A2 | 6/1994 |
| WO | WO9428938 A1 | 12/1994 |
| WO | WO9500655 A1 | 1/1995 |
| WO | WO9511984 A2 | 5/1995 |
| WO | WO9604388 A1 | 2/1996 |
| WO | WO9617958 A1 | 6/1996 |
| WO | WO9622024 A1 | 7/1996 |
| WO | WO9733899 A1 | 9/1997 |
| WO | WO9734631 A1 | 9/1997 |
| WO | WO9746313 A1 | 12/1997 |
| WO | WO9904813 A1 | 2/1999 |
| WO | WO9909217 A1 | 2/1999 |
| WO | WO9923105 A1 | 5/1999 |
| WO | WO9951773 A1 | 10/1999 |
| WO | WO2009089004 A1 | 7/2009 |
| WO | WO2010104821 A1 | 9/2010 |
| WO | WO2010132341 A2 | 11/2010 |
| WO | WO2012033953 A1 | 3/2012 |
| WO | WO2013134743 A1 | 9/2013 |

OTHER PUBLICATIONS

Ecker, Joseph R., and Ronald W. Davis. "Inhibition of gene expression in plant cells by expression of antisense RNA." Proceedings of the National Academy of Sciences 83.15 (1986): 5372-5376.

Feng, Li, et al. "High-level expression and mutagenesis of recombinant human phosphatidylcholine transfer protein using a synthetic gene: evidence for a C-terminal membrane binding domain." Biochemistry 39.50 (2000): 15399-15409.

Cardone, Rosa A., Valeria Casavola, and Stephan J. Reshkin. "The role of disturbed pH dynamics and the Na+/H+ exchanger in metastasis." Nature Reviews Cancer 5.10 (2005): 786-795.

Gluzman, Yakov. "SV40-transformed simian cells support the replication of early SV40 mutants." Cell 23.1 (1981): 175-182.

Lentz, Thomas L. "The recognition event between virus and host cell receptor: a target for antiviral agents." Journal of General Virology 71.4 (1990): 751-766.

Kondo, A., and M. Ueda. "Yeast cell-surface display—applications of molecular display." Applied microbiology and biotechnology 64.1 (2004): 28-40.

Kufer, Peter, Ralf Lutterbuse, and Patrick A. Baeuerle. "A revival of bispecific antibodies." Trends in biotechnology 22.5 (2004): 238-244.

Lee, Sang Yup, Jong Hyun Choi, and Zhaohui Xu. "Microbial cell-surface display." Trends in biotechnology 21.1 (2003): 45-52.

Makarova, Kira S., et al. "Evolution and classification of the CRISPR—Cas systems." Nature Reviews Microbiology 9.6 (2011): 467-477.

Narum, David L., et al. "Codon Optimization of Gene Fragments EncodingPlasmodium falciparum Merzoite Proteins Enhances DNA Vaccine Protein Expression and Immunogenicity in Mice." Infection and immunity 69.12 (2001): 7250-7253.

Ho, Mitchell, Satoshi Nagata, and Ira Pastan. "Isolation of anti-CD22 Fv with high affinity by Fv display on human cells." Proceedings of the National Academy of Sciences 103.25 (2006): 9637-9642.

Mali, Prashant, Kevin M. Esvelt, and George M. Church. "Cas9 as a versatile tool for engineering biology." Nature methods 10.10 (2013): 957-963.

Han, Junyan, and Kevin Burgess. "Fluorescent indicators for intracellular pH." Chemical reviews 110.5 (2009): 2709-2728.

Hagberg, Henrik. "Intracellular pH during ischemia in skeletal muscle: relationship to membrane potential, extracellular pH, tissue lactic acid and ATP." Pflügers Archiv 404.4 (1985): 342-347.

Needleman, Saul B., and Christian D. Wunsch. "A general method applicable to the search for similarities in the amino acid sequence of two proteins." Journal of molecular biology 48.3 (1970): 443-453.

Pearson, William R., and David J. Lipman. "Improved tools for biological sequence comparison." Proceedings of the National Academy of Sciences 85.8 (1988): 2444-2448.

Shawket, S., et al. "Selective suprasensitivity to calcitonin-gene-related peptide in the hands in Raynaud's phenomenon." The Lancet 334.8676 (1989): 1354-1357.

Roberge, Jacques Y., Xenia Beebe, and Samuel J. Danishefsky. "A strategy for a convergent synthesis of N-linked glycopeptides on a solid support." Science 269.5221 (1995): 202.

Waterman, Michael S., Temple F. Smith, and William A. Beyer. "Some biological sequence metrics." Advances in Mathematics 20.3 (1976): 367-387.

Rios, Eon J., et al. "Chronic hypoxia elevates intracellular pH and activates Na+/H+ exchange in pulmonary arterial smooth muscle cells." American Journal of Physiology-Lung Cellular and Molecular Physiology 289.5 (2005): L867-L874.

(56) References Cited

OTHER PUBLICATIONS

Outchkourov, Nikolay S., Willem J. Stiekema, and Maarten A. Jongsma. "Optimization of the expression of equistatin in Pichia pastoris." Protein expression and purification 24.1 (2002): 18-24.

Smith, Temple F., and Michael S. Waterman. "Overlapping genes and information theory." Journal of theoretical biology 91.2 (1981): 379-380.

Smith, Temple F., Michael S. Waterman, and Walter M. Fitch. "Comparative biosequence metrics." Journal of Molecular Evolution 18.1 (1981): 38-46.

Reidhaar-Olson, John F., and Robert T. Sauer. "Combinatorial cassette mutagenesis as a probe of the informational content of protein sequences." Science 241.4861 (1988): 53-58.

Xiong, Cheng-Yi, et al. "Development of tumor targeting anti-MUC-1 multimer: effects of di-scFv unpaired cysteine location on PEGylation and tumor binding." Protein Engineering Design and Selection 19.8 (2006): 359-367.

International Search Report and Written Opinion; dated Oct. 29, 2015 for PCT Application No. PCT/US2015/048258.

Köhler, Georges, and Cesar Milstein. "Continuous cultures of fused cells secreting antibody of predefined specificity." nature 256.5517 (1975): 495-497.

Boder, Eric T., and K. Dane Wittrup. "Yeast surface display for screening combinatorial polypeptide libraries." Nature Biotechnology 15.6 (1997): 553-557.

Nannemann, David P., et al. "Assessing directed evolution methods for the generation of biosynthetic enzymes with potential in drug biosynthesis." Future medicinal chemistry 3.7 (2011): 809-819.

European Search Report; dated Mar. 5, 2018 for EP Application No. EP15838974.

Australian Exam Report; dated Jun. 27, 2018 for AU Application No. 2015311911.

Chilean Office Action; dated May 23, 2018 for CL Application No. 201700528.

Berger, Carolina, et al. "Adoptive transfer of virus-specific and tumor-specific T cell immunity." Current opinion in immunology 21.2 (2009): 224-232.

Arulmani, Udayasankar, et al. "Calcitonin gene-related peptide and its role in migraine pathophysiology." European journal of pharmacology 500.1 (2004): 315-330.

Anderson, J. Christopher, et al. "An expanded genetic code with a functional quadruplet codon." Proceedings of the National Academy of Sciences of the United States of America 101.20 (2004): 7566-7571.

Chaudhary, Vijay K., et al. "A recombinant single-chain immunotoxin composed of anti-Tac variable regions and a truncated diphtheria toxin." Proceedings of the National Academy of Sciences 87.23 (1990): 9491-9494.

Beerli, Roger R., et al. "Isolation of human monoclonal antibodies by mammalian cell display." Proceedings of the National Academy of Sciences 105.38 (2008): 14336-14341.

Bedzyk, William D., et al. "Immunological and structural characterization of a high affinity anti-fluorescein single-chain antibody." Journal of biological chemistry 265.30 (1990): 18615-18620.

Ghatta, Srinivas, and D. Nimmagadda. "Calcitonin gene-related peptide: Understanding its role." Indian journal of pharmacology 36.5 (2004): 277.

Fonseca, Carmen, David Abraham, and Markella Ponticos. "Neuronal regulators and vascular dysfunction in Raynaud's phenomenon and systemic sclerosis." Current vascular pharmacology 7.1 (2009): 34-39.

Chi, Sulene L., and Salvatore V. Pizzo. "Angiostatin is directly cytotoxic to tumor cells at low extracellular pH: a mechanism dependent on cell surface-associated ATP synthase." Cancer research 66.2 (2006): 875-882.

Geysen, H. Mario, Rob H. Meloen, and Simon J. Barteling. "Use of peptide synthesis to probe viral antigens for epitopes to a resolution of a single amino acid." Proceedings of the National Academy of Sciences 81.13 (1984): 3998-4002.

EP Office Action; dated Dec. 21, 2018 for EP Application No. 15 838 974.2.

Guo, Jing, Thomas Gaj, and Carlos F. Barbas III. "Directed evolution of an enhanced and highly efficient FokI cleavage domain for zinc finger nucleases." Journal of molecular biology 400.1 (2010): 96-107.

Jager, Volker, et al., "High level transient production of recombinant antibodies and antibody fusion proteins in HEK293 cells" BMC Biotechnology, Jun. 26, 2013, 13:52.

* cited by examiner

DISCOVERING AND PRODUCING CONDITIONALLY ACTIVE BIOLOGIC PROTEINS IN THE SAME EUKARYOTIC CELL PRODUCTION HOSTS

RELATED APPLICATION DATA

This application claims priority to International Application No. PCT/US15/48258, filed Sep. 3, 2015, and U.S. Provisional Application No. 62/045,207, filed Sep. 3, 2014, the entire disclosure of which is hereby incorporated by reference as if set forth fully herein.

FIELD OF THE DISCLOSURE

This disclosure relates to the fields of protein evolution and activity. Specifically, this disclosure relates to a method of generating conditionally active biologic proteins from wild type proteins, in particular therapeutic proteins, which generated proteins are reversibly or irreversibly virtually inactivated at normal physiological conditions typically encountered by the wild-type protein but active at other conditions. For example, evolved proteins are virtually inactive at body temperature, but are active at lower temperatures.

BACKGROUND OF THE DISCLOSURE

There is a considerable body of literature describing the potential for evolving proteins for a variety of characteristics, especially enzymes for example, to be stabilized for operation at different conditions. For example, enzymes have been evolved to be stabilized at higher temperatures, with varying activity. In situations where there is an activity improvement at the high temperature, a substantial portion of the improvement can be attributed to the higher kinetic activity commonly described by the Q10 rule where it is estimated that in the case of an enzyme the turnover doubles for every increase of 10 degrees Celsius. In addition, there exist examples of natural mutations that destabilize proteins at their normal operating conditions, such as the activity of the molecule at a given temperature. For temperature mutants, these mutants can be active at a lower temperature, but typically are active at a reduced level compared to the wild type molecules from which they are derived. This may be described by a reduction in activity guided by the Q10 or similar rules.

It is desirable to generate useful molecules that are conditionally active. For example, such molecules may be virtually inactive under conditions typically encountered by the corresponding wild-type molecule from which they are derived, but are active at other conditions at a level that is equal to or higher than the activity under the conditions typically encountered by the corresponding wild-type molecule, or that are activated or inactivated in certain microenvironments, or that are activated or inactivated over time. Besides temperature, other conditions for which the proteins can be evolved or optimized include pH, osmotic pressure, osmolality, oxidative stress and electrolyte concentration. Other desirable properties that can be optimized during evolution include chemical resistance, and proteolytic resistance.

Many strategies for evolving or engineering molecules have been published. However, engineering or evolving a protein to be inactive or virtually inactive (less than 10% activity and especially 1% activity) at its wild type operating condition, while maintaining activity equivalent or better than its wild type condition at new conditions, requires that the destabilizing mutation(s) co-exist with activity increasing mutations that do not counter the destabilizing effect. It is expected that destabilization would reduce the protein's activity greater than the effects predicted by standard rules such as Q10, therefore the ability to evolve proteins that work efficiently at lower temperature, for example, while being inactivated under their normal operating condition, creates an unexpected new class of proteins we refer to as Mirac Proteins.

Throughout this application, various publications are referenced by author and date. The disclosures of these publications in their entireties are hereby incorporated by reference into this application in order to more fully describe the state of the art as known to those skilled therein as of the date of the disclosure described and claimed herein.

SUMMARY OF THE DISCLOSURE

The disclosure provides a method of preparing a conditionally active biologic protein, the method comprising the steps of: selecting a wild-type biologic protein, evolving the DNA which encodes the wild-type biologic protein using one or more evolutionary techniques to create mutant DNAs, expressing the mutant DNAs in a eukaryotic cell production host to obtain a mutant protein, subjecting the mutant protein and the wild-type protein to an assay under a normal physiological condition and to an assay under an aberrant condition, selecting a conditionally active mutant protein which exhibits at least one of: (a) a decrease in activity in the assay at the normal physiological condition compared to the wild-type protein, and (b) an increase in activity in the assay under the aberrant condition compared to the wild-type protein; and producing the conditionally active biologic protein in the same eukaryotic cell production host used in the expression step. In another aspect, the conditionally active mutant protein exhibits both: (a) a decrease in activity in the assay at the normal physiological condition compared to the wild-type protein, and (b) an increase in activity in the assay under the aberrant condition compared to the wild-type protein. In various aspects, the normal physiological condition is selected from one or more of temperature, pH, osmotic pressure, osmolality, oxidative stress and electrolyte concentration. In a particular aspect, the normal physiological condition is temperature; wherein the conditionally active biologic protein is virtually inactive at the normal physiological temperature, but is active at an aberrant temperature less than the normal physiological temperature. In other aspects, the conditionally active biologic protein is reversibly or irreversibly inactivated at the wild type normal physiological conditions. In one specific aspect, the protein is reversibly inactivated at the wild type normal physiological conditions. Alternatively, conditionally active biologic proteins are selected from those proteins which exhibit changes in activity, reversibly or irreversibly, in two or more different physiological conditions.

In one embodiment, the wild-type biologic protein is an enzyme, in certain aspects the wild-type biologic protein is selected from the group consisting of tissue plasminogen activator, streptokinase, urokinase, renin, and hyaluronidase.

In another embodiment, the wild-type biologic protein is selected from calcitonin gene-related peptide (CGRP), substance P (SP), neuropeptide Y (NPY), vasoactive intestinal peptide (VTP), vasopressin, and angiostatin.

In another embodiment, the biologic protein is an antibody.

In another embodiment, the normal physiological condition in any of the preceding embodiments is temperature; and the conditionally active biologic protein is substantially inactive at the normal physiological temperature, and is active at an aberrant temperature less than the normal physiological temperature.

In another embodiment, the evolving step in any of the preceding embodiments comprises a technique selected from the group consisting of PCR, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis, in vitro mutagenesis, ligase chain reaction, oligonucleotide synthesis and combination thereof.

In another embodiment, the eukaryotic cell production host in any of the preceding embodiments is selected from a fungal cell, an insect cell, a mammalian cell, an adenovirus, and a plant cell.

In another embodiment, the mammalian cell in any of the preceding embodiments is selected from Bowes melanoma cells, COS-7 cells, C127 cells, HeLa cells, BHK cells, 3T3 mouse fibroblast cells, BHK21 Syrian hamster fibroblast cells, MDCK dog epithelial cells, PtK1 rat kangaroo epithelial cells, SP2/0 mouse plasma cells, NS0 mouse plasma cells, HEK 293 human embryonic kidney cells, COS monkey kidney cells, CHO cells, CHO-S, R1 mouse embryonic cells, E14.1 mouse embryonic cells, H1 human embryonic cells, H9 human embryonic cells, and PER C.6, human embryonic cells.

In another embodiment, the producing step of any of the preceding embodiments comprises manufacturing.

In another embodiment, the conditionally active biologic protein in any of the preceding embodiments is used as a recognition protein by a viral particle.

In another embodiment, the conditionally active biologic protein in any of the preceding embodiments that binds with a target protein on a target cell is integrated into a chimeric antigen receptor.

In another embodiment, the conditionally active biologic protein prepared by the method of any of the preceding embodiments is reversibly or irreversibly inactivated at the normal physiological condition.

In another embodiment, the conditionally active biologic protein of the previous paragraph comprises at least one non-natural amino acid.

In another embodiment, the conditionally active biologic protein of the previous two paragraphs is a part of a chimeric antigen receptor.

In another embodiment, the disclosure provides a pharmaceutical composition comprising a conditionally active biologic protein, and a pharmaceutically acceptable carrier.

BRIEF DESCRIPTION OF THE DRAWING

The application file contains at least one drawing executed in color. Copies of this patent application publication with color drawings will be provided by the Office upon request and payment of the necessary fee.

DEFINITIONS

Figure 1:
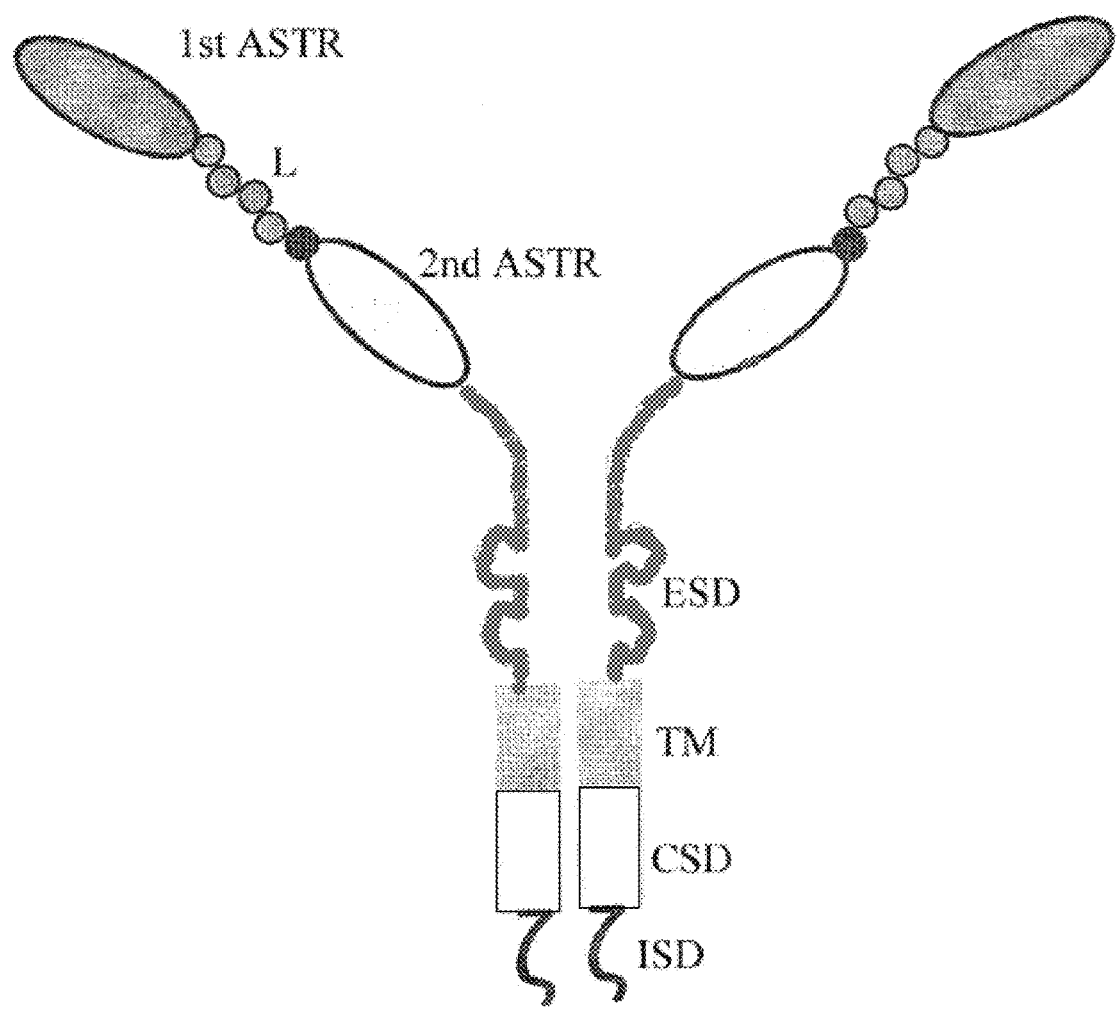
FIG. 1 depicts a schematic representation of a chimeric antigen receptor in accordance with one embodiment of the present invention. ASTR is an antigen-specific targeting region, L is a linker, ESD is an extracellular spacer domain, TM is a transmembrane domain, CSD is a co-stimulatory domain, and ISD is an intracellular signaling domain.

In order to facilitate understanding of the examples provided herein, certain frequently occurring methods and/or terms will be defined herein.

As used herein in connection with a measured quantity, the term "about" refers to the normal variation in that measured quantity that would be expected by the skilled artisan making the measurement and exercising a level of care commensurate with the objective of the measurement and the precision of the measuring equipment used. Unless otherwise indicated, "about" refers to a variation of +/−10% of the value provided.

The term "agent" is used herein to denote a chemical compound, a mixture of chemical compounds, an array of spatially localized compounds (e.g., a VLSIPS peptide array, polynucleotide array, and/or combinatorial small molecule array), biological macromolecule, a bacteriophage peptide display library, a bacteriophage antibody (e.g., scFv) display library, a polysome peptide display library, or an extract made from biological materials such as bacteria, plants, fungi, or animal (particular mammalian) cells or tissues. Agents are evaluated for potential enzyme activity by inclusion in screening assays described herein below. Agents are evaluated for potential activity as conditionally active biologic therapeutic enzymes by inclusion in screening assays described herein below.

An "ambiguous base requirement" in a restriction site refers to a nucleotide base requirement that is not specified to the fullest extent, i.e. that is not a specific base (such as, in a non-limiting exemplification, a specific base selected from A, C, G, and T), but rather may be any one of at least two or more bases. Commonly accepted abbreviations that are used in the art as well as herein to represent ambiguity in bases include the following: R=G or A; Y=C or T; M=A or C; K=G or T; S=G or C; W=A or T; H=A or C or T; B=G or T or C; V=G or C or A; D=G or A or T; N=A or C or G or T.

The term "amino acid" as used herein refers to any organic compound that contains an amino group (—NH$_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gin or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (tip or W), tyrosine (tyr or Y), and valine (val or V).

The term "amplification" means that the number of copies of a polynucleotide is increased.

The term "antibody", as used herein, refers to intact immunoglobulin molecules, as well as fragments of immunoglobulin molecules, such as Fab, Fab', (Fab')2, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like. Chimeric, human-like, humanized or fully human antibodies are particularly useful for administration to human patients.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

The term "blood-brain barrier" or "BBB" refers to the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The blood-brain barrier within the brain, the blood-spinal cord barrier within the spinal cord, and the blood-retinal barrier within the retina are contiguous capillary barriers within the central nerve system (CNS), and are herein collectively referred to as the "blood-brain barrier" or "BBB." The BBB also encompasses the blood-cerebral spinal fluid barrier (choroid plexus) where the barrier is comprised of ependymal cells rather than capillary endothelial cells.

The term "cell production host", or "manufacturing host", refers to a cell line used for the production or manufacturing of proteins. Eukaryotic cell production hosts such as mammalian cells, including, but not limited to human, mouse, hamster, rat, monkey cell lines as well as yeast, insect and plant cell lines. Prokaryotic cell production hosts can alternatively be utilized. In one aspect, a mammalian cell production host is selected from a member of the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells. In another aspect, the eukaryotic cell production host is a GS-NS0 or GS-CHOK1 cell line. In another aspect, the eukaryotic cell production host is selected from S. cerevisiae yeast cells; and picchia yeast cells. In another aspect, the cell production host is a bacterial cell line.

The terms "cancer" and "cancerous" as used herein refer to or describe the physiological condition in mammals that is typically characterized by unregulated cell growth. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

The term "chimeric antigen receptor" or "CAR" or "CARs" as used herein refers to engineered receptors, which graft an antigen specificity onto cytotoxic cell, for example T cells, NK cells and macrophages. The CARs of the invention may comprise at least one antigen specific targeting region (ASTR), an extracellular spacer domain (ESD), a transmembrane domain (TM), one or more co-stimulatory domains (CSD), and an intracellular signaling domain (ISD). In an embodiment, the ESD and/or CSD are optional. In another embodiment, the CAR is a bispecific CAR, which is specific to two different antigens or epitopes. After the ASTR binds specifically to a target antigen, the ISD activates intracellular signaling. For example, the ISD can redirect T cell specificity and reactivity toward a selected target in a non-MHC-restricted manner, exploiting the antigen-binding properties of antibodies. The non-MHC-restricted antigen recognition gives T cells expressing the CAR the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains.

A molecule that has a "chimeric property" is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assembling a reassortment of partial molecular sequences. In a non-limiting aspect, a chimeric polynucleotide molecule may be prepared by synthesizing the chimeric polynucleotide using plurality of molecular templates, such that the resultant, chimeric polynucleotide has properties of a plurality of templates.

The term "cognate" as used herein refers to a gene sequence that is evolutionarily and functionally related between species. For example, but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

The term "commercial scale" means production of a protein or antibody at a scale appropriate for resale.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith (Smith and Waterman, 1981 "Comparison of biosequences", Adv Appl Math, 2:482-489; Smith and Waterman, 1981, "Overlapping genes and information theory", J Theor Biol, 91:379-380; Smith and Waterman, J Mol Biol, "Identification of common molecular subsequences", 1981, 147:195-197; Smith et al., 1981, "Comparative biosequence metrics", J Mol Evol, 18:38-46), by the homology alignment algorithm of Needleman (Needleman and Wunsch, 1970, "A general method applicable to the search for similarities in the amino acid sequence of two proteins" J Mol Biol, 48(3):443-453), by the search of similarity method of Pearson (Pearson and Lipman, 1988, "Improved tools for biological sequence comparison", Proc Nat Acad Sci USA, 85:2444-2448), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "conditionally active biologic protein" refers to a variant, or mutant, of a wild-type protein which is more or less active than the parent wild-type protein under one or more normal physiological conditions. This conditionally active protein also exhibits activity in selected regions of the body and/or exhibits increased or decreased activity under aberrant, or permissive, physiological conditions. Normal physiological conditions are those of temperature, pH, osmotic pressure, osmolality, oxidative stress and electrolyte concentration which would be considered within a normal range at the site of administration, or at the tissue or organ at the site of action, to a subject. An aberrant condition is that which deviates from the normally acceptable range for that condition. In one aspect, the conditionally active biologic protein is virtually inactive at wild-type conditions but is active at other than wild-type conditions at a level that is equal or better than at wild-type conditions. For example, in one aspect, an evolved conditionally active biologic protein is virtually inactive at body temperature, but is active at lower temperatures. In another aspect, the conditionally active biologic protein is reversibly or irreversibly inactivated at the wild type conditions. In a further aspect, the wild-type protein is a therapeutic protein. In another aspect, the conditionally active biologic protein is used as a drug, or therapeutic agent. In yet another aspect, the protein is more or less active in highly oxygenated blood, such as, for example, after passage through the lung or in the lower pH environments found in the kidney.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "co-stimulatory ligand" as used herein includes a molecule on an antigen presenting cell (e.g., dendritic cell, B cell, and the like) that specifically binds a cognate co-stimulatory molecule on a T cell, thereby providing a signal which, in addition to the primary signal provided by, for instance, by the binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, an inducible costimulatory ligand (ICOS-L), an intercellular adhesion molecule (ICAM), CD30L, CD40, CD70, CD83, HLA-G, MICA, MICB, HVEM, a lymphotoxin beta receptor, 3/TR6, ILT3, ILT4, HVEM, an agonist or an antibody that binds to a Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, a lymphocyte function-associated antigen-1 (LFA-1), CD2, CD7, LIGHT, NKG2C, B7-H3, and a ligand that specifically binds with CD83.

The term "co-stimulatory molecule" as used herein refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class 1 molecule, BTLA and a Toll ligand receptor.

The term "co-stimulatory signal" as used herein refers to a signal, which in combination with a primary signal, such as TCR/CD3 ligation, leads to T cell proliferation and/or upregulation or down regulation of key molecules.

The term "cytotoxic cell" as used herein means a cell which can injure or destroy invading microorganisms, tumor cells or other diseased tissue cells. This term is meant to include natural killer (NK) cells, activated NK cells, neutrophils, T cells, eosinophils, basophils, B-cells, macrophages and lymphokine-activated killer (LAK) cells among other cell types. The cytotoxic cell, through an antibody, receptor, ligand or fragments/derivatives thereof, is bound to a target cell to form a stable complex, and stimulates the cytotoxic cell to destroy the target cell.

The term "degrading effective" amount refers to the amount of enzyme which is required to process at least 50% of the substrate, as compared to substrate not contacted with the enzyme.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a .beta.-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues, and the like, either segmentally or over the entire length of the individual selected library member sequence. Defined sequence kernels can refer to either amino acid sequences or polynucleotide sequences. Of illustration and not limitation, the sequences $(NNK)_{10}$ and $(NNM)_{10}$, wherein N represents A, T, G, or C; K represents G or T; and M represents A or C, are defined sequence kernels.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 microgram of plasmid or DNA fragment is used with about 2 units of enzyme in about 20 microliters of buffer solution. For the purpose of isolating DNA fragments for plasmid construction, typically 5 to 50 micrograms of DNA are digested with 20 to 250 units of enzyme in a larger volume. Appropriate buffers and substrate amounts for particular restriction enzymes are specified by the manufacturer. Incubation times of about 1 hour at 37 degrees C. are ordinarily used, but may vary in accordance with the supplier's instructions. After digestion the reaction is electrophoresed directly on a gel to isolate the desired fragment.

"Directional ligation" refers to a ligation in which a 5' end and a 3' end of a polynucleotide are different enough to specify a preferred ligation orientation. For example, an otherwise untreated and undigested PCR product that has two blunt ends will typically not have a preferred ligation orientation when ligated into a cloning vector digested to produce blunt ends in its multiple cloning site; thus, directional ligation will typically not be displayed under these circumstances. In contrast, directional ligation will typically be displayed when a digested PCR product having a 5' EcoR I-treated end and a 3' BamH I is ligated into a cloning vector that has a multiple cloning site digested with EcoR I and BamH I.

The term "disease targeted by genetically modified cytotoxic cells" as used herein encompasses the targeting of any cell involved in any manner in any disease by the genetically modified cells of the invention, irrespective of whether the genetically modified cells target diseased cells or healthy cells to effectuate a therapeutically beneficial result. The genetically modified cells include but are not limited to genetically modified T cells, NK cells, and macrophages. The genetically modified cells express the CARs of the invention, which CARs may target any of the antigens expressed on the surface of target cells. Examples of antigens which may be targeted include but are not limited to antigens expressed on B-cells; antigens expressed on carcinomas, sarcomas, lymphomas, leukemia, germ cell tumors, and blastomas; antigens expressed on various immune cells; and antigens expressed on cells associated with various hematologic diseases, autoimmune diseases, and/or inflammatory diseases. Other antigens that may be targeted will be apparent to those of skill in the art and may be targeted by the CARs of the invention in connection with alternate embodiments thereof.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like. DNA shuffling can be random or non-random.

The term "drug" or "drug molecule" refers to a therapeutic agent including a substance having a beneficial effect on a human or animal body when it is administered to the human or animal body. Preferably, the therapeutic agent includes a substance that can treat, cure or relieve one or more symptoms, illnesses, or abnormal conditions in a human or animal body or enhance the wellness of a human or animal body.

An "effective amount" is an amount of a conditionally active biologic protein or fragment which is effective to treat or prevent a condition in a living organism to whom it is administered over some period of time, e.g., provides a therapeutic effect during a desired dosing interval.

As used herein, the term "electrolyte" is used to define a mineral in the blood or other body fluids that carries a charge. For example, in one aspect, the normal physiological condition and aberrant condition can be conditions of "electrolyte concentration". In one aspect, the electrolyte concentration to be tested is selected from one or more of ionized calcium, sodium, potassium, magnesium, chloride, bicarbonate, and phosphate concentration. For example, in one aspect, normal range of serum calcium is 8.5 to 10.2 mg/dL. In this aspect, aberrant serum calcium concentration may be selected from either above or below the normal range, m another example, in one aspect, normal range of serum chloride is 96-106 milliequivalents per liter (mEq/L). In this aspect, aberrant serum chloride concentration may be selected from either above or below the normal range, in another example, in one aspect, a normal range of serum magnesium is from 1.7-2.2 mg/dL. In this aspect, an aberrant serum magnesium concentration may be selected from either above or below the normal range, in another example, in one aspect, a normal range of serum phosphorus is from 2.4 to 4.1 mg/dL. In this aspect, aberrant serum phosphorus concentration may be selected from either above or below the normal range. In another example, in one aspect, a normal range of serum, or blood, sodium is from 135 to 145 mEq/L. In this aspect, aberrant serum, or blood, sodium concentration may be selected from either above or below the normal range. In another example, in one aspect, a normal range of serum, or blood, potassium is from 3.7 to 5.2 mEq/L. In this aspect, aberrant serum, or blood, potassium concentration maybe selected from either above or below the normal range. In a further aspect, a normal range of serum bicarbonate is from 20 to 29 mEq/L. In this aspect, aberrant serum, or blood, bicarbonate concentration may be selected from either above or below the normal range. In a different aspect, bicarbonate levels can be used to indicate normal levels of acidity (pH), in the blood. The term "electrolyte concentration" may also be used to define the condition of a particular electrolyte in a tissue or body fluid other than blood or plasma. In this case, the normal physiological condition is considered to be the clinically normal range for that tissue or fluid. In this aspect, aberrant tissue or fluid electrolyte concentration may be selected from either above or below the normal range.

As used in this disclosure, the term "epitope" refers to an antigenic determinant on an antigen, such as an enzyme polypeptide, to which the paratope of an antibody, such as an enzyme-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

As used herein, an "enzyme" is a protein with specific catalytic properties. Factors such as, for example, substrate concentration, pH, temperature and presence or absence of inhibitors can affect the rate of catalysis. Typically, for a wild type enzyme, Q10 (the temperature coefficient) describes the increase in reaction rate with a 10 degree C. rise in temperature. For wild type enzymes, the Q10=2 to 3; in other words, the rate of reaction doubles or triples with every 10 degree increase in temperature. At high temperatures, proteins denature. At pH values slightly different from an enzymes optimum value, small changes occur in the charges of the enzyme and perhaps the substrate molecule. The change in ionization can affect the binding of the substrate molecule. At extreme pH levels, the enzyme will produce denaturation, where the active site is distorted, and the substrate molecule will no longer fit.

As used herein, the term "evolution", or "evolving", refers to using one or more methods of mutagenesis to generate a novel polynucleotide encoding a novel polypeptide, which novel polypeptide is itself an improved biological molecule &/or contributes to the generation of another improved biological molecule. In a particular non-limiting aspect, the present disclosure relates to evolution of conditionally active biologic proteins from a parent wild type protein. In one aspect, for example, evolution relates to a method of performing both non-stochastic polynucleotide chimerization and non-stochastic site-directed point mutagenesis disclosed in U.S. patent application publication 2009/0130718, which is incorporated herein by reference. More particularly, the present disclosure provides methods for evolution of conditionally active biologic enzymes which exhibit reduced activity at normal physiological conditions compared to a wild-type enzyme parent molecule, but enhanced activity under one or more aberrant conditions compared to the wild-type enzyme.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

A method is provided herein for producing from a template polypeptide a set of progeny polypeptides in which a "full range of single amino acid substitutions" is represented at each amino acid position. As used herein, "full range of single amino acid substitutions" is in reference to the 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (nitrons) between individual coding segments (exons).

"Genetic instability", as used herein, refers to the natural tendency of highly repetitive sequences to be lost through a process of reductive events generally involving sequence simplification through the loss of repeated sequences. Deletions tend to involve the loss of one copy of a repeat and everything between the repeats.

The terms "genetically modified cells", "redirected cells", "genetically engineered cells" or "modified cells" as used herein refer to cells that express the conditionally active CARs of the invention.

The term "heterologous" means that one single-stranded nucleic acid sequence is unable to hybridize to another single-stranded nucleic acid sequence or its complement. Thus, areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The benefits of this disclosure extend to "industrial applications" (or industrial processes), which term is used to include applications in commercial industry proper (or simply industry) as well as non-commercial industrial applications (e.g. biomedical research at a non-profit institution). Relevant applications include those in areas of diagnosis, medicine, agriculture, manufacturing, and academia.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide.

The term "immune cell" as used herein refers to cells of the mammalian immune system including but not limited to antigen presenting cells, B-cells, basophils, cytotoxic T cells, dendritic cells, eosinophils, granulocytes, helper T cells, leukocytes, lymphocytes, macrophages, mast cells, memory cells, monocytes, natural killer cells, neutrophils, phagocytes, plasma cells and T cells.

The term "immune response" as used herein refers to immunities including but not limited to innate immunity, humoral immunity, cellular immunity, immunity, inflammatory response, acquired (adaptive) immunity, autoimmunity and/or overactive immunity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The term "isolated nucleic acid" is used to define a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The term "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient ways to deliver a gene delivery vector. HIV, SIV, and FIV are all examples of lentiviruses. Vectors derived from lentiviruses offer the means to achieve significant levels of gene transfer in vivo.

As used herein "ligand" refers to a molecule, such as a random peptide or variable segment sequence that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Sambrook et al., (1982). Molecular Cloning: A Laboratory Manual. Cold Spring Harbour Laboratory, Cold Spring Harbor, N.Y., p. 146; Sambrook et al., Molecular Cloning: a laboratory manual, $2^{nd}$ Ed., Cold Spring Harbor Laboratory Press, 1989). Unless otherwise provided, ligation may be accomplished using known buffers and conditions with 10 units of T4 DNA ligase ("ligase") per 0.5 micrograms of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

The term "mammalian cell surface display" refers to a technique whereby a protein or antibody, or a portion of an antibody, is expressed and displayed on a mammalian host cell surface for screening purposes; for example, by screening for specific antigen binding by a combination of magnetic beads and fluorescence-activated cell sorting. In one aspect, mammalian expression vectors are used for simultaneous expression of immunoglobulins as both a secreted and cell surface bound form as in DuBridge et al., US 2009/0136950, which is incorporated herein by reference. In another aspect, the techniques are employed for a viral vector encoding for a library of antibodies or antibody fragments that are displayed on the cell membranes when expressed in a cell as in Gao et al., US 2007/0111260, incorporated herein by reference. Whole IgG surface display on mammalian cells is known. For example, Akamatsuu et al. developed a mammalian cell surface display vector, suitable for directly isolating IgG molecules based on their antigen-binding affinity and biological activity. Using an Epstein-Barr virus-derived episomal vector, antibody libraries were displayed as whole IgG molecules on the cell surface and screened for specific antigen binding by a combination of magnetic beads and fluorescence-activated cell sorting. Plasmids encoding antibodies with desired binding characteristics were recovered from sorted cells and converted to the form suitable for production of soluble IgG. See Akamatsuu et al. *J. Immunol. Methods, vol.* 327, pages 40-52, 2007, incorporated herein by reference. Ho et al. used human embryonic kidney 293T cells that are widely used for transient protein expression for cell surface display of single-chain Fv antibodies for affinity maturation. Cells expressing a rare mutant antibody with higher affinity were enriched 240-fold by single-pass cell sorting from a large excess of cells expressing WT antibody with a slightly lower affinity. Furthermore, a highly enriched mutant was obtained with increased binding affinity for CD22 after a single selection of a combinatory library randomizing an intrinsic antibody hotspot. See Ho et al., "Isolation of anti-CD22 Fv with high affinity by Fv display on human cells," *Proc Natl Acad Sci USA, vol.* 103, pages 9637-9642, 2006, incorporated herein by reference.

B cells specific for an antigen can also be used. Such cells may be directly isolated from peripheral blood mononuclear cells (PBMC) of human donors. Recombinant, antigen-specific single-chain Fv (scFv) libraries are generated from this pool of B cells and screened by mammalian cell surface display by using a Sindbis virus expression system. This method allows isolating antigen-specific antibodies by a single round of FACS. The variable regions (VRs) of the heavy chains (HCs) and light chains (LCs) were isolated from positive clones and recombinant fully human antibodies produced as whole IgG or Fab fragments. In this manner, several hypermutated high-affinity antibodies binding the Qβ virus like particle (VLP), a model viral antigen, as well as antibodies specific for nicotine were isolated. All antibodies showed high expression levels in cell culture. The human nicotine-specific mAbs were validated preclinically in a mouse model. See Beerli et al., "Isolation of human monoclonal antibodies by mammalian cell display," *Proc Natl Acad Sci USA*, vol. 105, pages 14336-14341, 2008, incorporated herein by reference.

Yeast cell surface display may also be used in the present invention, for example, see Kondo and Ueda, "Yeast cell-surface display-applications of molecular display," *Appl. Microbiol. Biotechnol.*, vol. 64, pages 28-40, 2004, which describes for example, a cell-surface engineering system using the yeast *Saccharomyces cerevisiae*. Several representative display systems for the expression in yeast *S. cerevisiae* are described in Lee et al, "Microbial cell-surface display," *TRENDS in Bitechnol.*, vol. 21, pages 45-52, 2003. Also Boder and Wittrup, "Yeast surface display for screening combinatorial polypeptide libraries," *Nature Biotechnol.*, vol. 15, pages 553, 1997.

The term "manufacturing" refers to production of a protein at a sufficient quantity to permit at least Phase I clinical testing of a therapeutic protein, or sufficient quantity for regulatory approval of a diagnostic protein.

As used herein "microenvironment" means any portion or region of a tissue or body that has constant or temporal, physical or chemical differences from other regions of the tissue or regions of the body.

As used herein, a "molecular property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting-examples of molecular properties to be evolved include protein activities at specified conditions, such as related to temperature; salinity; osmotic pressure; pH; oxidation, and concentration of glycerol, DMSO, detergent, &/or any other molecular species with which contact is made in a reaction environment. Additional particularly relevant—but by no means limiting—examples of molecular properties to be evolved include stabilities—e.g. the amount of a residual molecular property that is present after a specified exposure time to a specified environment, such as may be encountered during storage.

The term "multispecific antibody" as used herein is an antibody having binding affinities for at least two different epitopes. Multispecific antibodies can be prepared as full-length antibodies or antibody fragments (e.g. F(ab')2 bispecific antibodies). Engineered antibodies may bind to two, three or more (e.g. four) antigens (see, e.g., US 2002/0004587 A1). One conditionally active antibody may be engineered to be multispecific, or two antibodies may be engineered to comprise a hetero-dimer that binds to two antigens. Multispecific antibodies can also be multifunctional.

The term "mutations" means changes in the sequence of a wild-type nucleic acid sequence or changes in the sequence of a peptide. Such mutations may be point mutations such as transitions or transversions. The mutations may be deletions, insertions or duplications.

As used herein, the degenerate "N,N,G/T" nucleotide sequence represents 32 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

As used herein, "normal physiological conditions", or "wild type operating conditions", are those conditions of temperature, pH, osmotic pressure, osmolality, oxidative stress and electrolyte concentration which would be considered within a normal range at the site of administration, or the site of action, in a subject.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a nonradioactive label, is likewise considered a "nucleic acid molecule".

The terms "nucleic acid sequence coding for" or a "DNA coding sequence of or a "nucleotide sequence encoding" a particular enzyme—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an enzyme (protein)" or "DNA encoding an enzyme (protein)" or "polynucleotide encoding an enzyme (protein)" and other synonymous terms encompasses a polynucleotide which includes only coding sequence for the enzyme as well as a polynucleotide which includes additional coding and/or non-coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable to its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present disclosure provides a "nucleic acid construct" or alternatively a "nucleotide construct" or alternatively a "DNA construct". The term "construct" is used herein to describe a molecule, such as a polynucleotide (e.g., an enzyme polynucleotide) which may optionally be chemically bonded to one or more additional molecular moieties, such as a vector, or parts of a vector. In a specific—but by no means limiting-aspect, a nucleotide construct is exemplified by DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "parental polynucleotide set" is a set comprised of one or more distinct polynucleotide species. Usually this term is used in reference to a progeny polynucleotide set which is preferably obtained by mutagenization of the parental set, in which case the terms "parental", "starting" and "template" are used interchangeably.

The term "patient", or "subject", refers to an animal, for example a mammal, such as a human, who is the object of treatment. The subject, or patient, may be either male or female.

As used herein the term "physiological conditions" refers to temperature, pH, osmotic pressure, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45 degrees C. and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0 percent nonspecific protein (e.g., bovine serum albumin (BSA)). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants. In some embodiments, the buffer may contain at least one of BSA, carbonates, bicarbonates, chloride salts, etc. Normal physiological conditions refer to conditions of temperature, pH, osmotic pressure, osmolality, oxidative stress and electrolyte concentration in vivo in a patient or subject at the site of administration, or the site of action, which would be considered within the normal range in a patient.

Standard convention (5' to 3') is used herein to describe the sequence of double stranded polynucleotides.

The term "population" as used herein means a collection of components such as polynucleotides, portions or polynucleotides or proteins. A "mixed population" means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g. glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When two or more chemical modifications (e.g. two proteolytic cleavages, or a proteolytic cleavage and a deglycosylation) can be distinguished en route to the production of a mature molecule, the reference precursor molecule may be termed a "pre-pro-form" molecule.

As used herein, the term "pseudorandom" refers to a set of sequences that have limited variability, such that, for example, the degree of residue variability at another position, but any pseudorandom position is allowed some degree of residue variation, however circumscribed.

"Quasi-repeated units", as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reasserted by this approach, they can be referred to as "quasi-repeated" units.

As used herein "random peptide library" refers to a set of polynucleotide sequences that encodes a set of random peptides, and to the set of random peptides encoded by those polynucleotide sequences, as well as the fusion proteins that contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

The term "recombinant antibody", as used herein, refers to an antibody (e.g. a chimeric, humanized, or human antibody or antigen-binding fragment thereof) that is expressed by a recombinant host cell comprising nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia. coli* cells or *Bacillus subtilis* cells, etc.

"Recombinant" enzymes refer to enzymes produced by recombinant DNA techniques, i.e., produced from cells transformed by an exogenous DNA construct encoding the desired enzyme. "Synthetic" enzymes are those prepared by chemical synthesis.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

"Repetitive Index (RI)", as used herein, is the average number of copies of the quasi-repeated units contained in the cloning vector.

The term "restriction site" refers to a recognition sequence that is necessary for the manifestation of the action of a restriction enzyme, and includes a site of catalytic cleavage. It is appreciated that a site of cleavage may or may not be contained within a portion of a restriction site that comprises a low ambiguity sequence (i.e. a sequence containing the principal determinant of the frequency of occurrence of the restriction site). Thus, in many cases, relevant restriction sites contain only a low ambiguity sequence with an internal cleavage site (e.g. G/AATTC in the EcoR I site) or an immediately adjacent cleavage site (e.g. /CCWGG in the EcoR II site), in other cases, relevant restriction enzymes [e.g. the EcoR I site or CTGAAG(16/14)] contain a low ambiguity sequence (e.g. the CTGAAG sequence in the Eco57 1 site) with an external cleavage site (e.g. in the N.sub.16 portion of the EcoR I site). When an enzyme (e.g. a restriction enzyme) is said to "cleave" a polynucleotide, it is understood to mean that the restriction enzyme catalyzes or facilitates a cleavage of a polynucleotide.

In a non-limiting aspect, a "selectable polynucleotide" is comprised of a 5' terminal region (or end region), an intermediate region (i.e. an internal or central region), and a 3' terminal region (or end region). As used in this aspect, a 5' terminal region is a region that is located towards a 5' polynucleotide terminus (or a 5' polynucleotide end); thus it is either partially or entirely in a 5' half of a polynucleotide. Likewise, a 3' terminal region is a region that is located towards a 3' polynucleotide terminus (or a 3' polynucleotide end); thus it is either partially or entirely in a 3' half of a polynucleotide. As used in this non-limiting exemplification, there may be sequence overlap between any two regions or even among all three regions.

As used herein, the term "single-chain antibody" refers to a polypeptide comprising a VH domain and a VL domain in a polypeptide linkage, generally linked via a spacer peptide, and which may comprise additional amino acid sequences at the amino- and/or carboxy-termini. For example, a single-chain antibody may comprise a tether segment for linking to the encoding polynucleotide. As an example a scFv is a single-chain antibody. Single-chain antibodies are generally proteins consisting of one or more polypeptide segments of at least 10 contiguous amino acids substantially encoded by genes of the immunoglobulin superfamily (e.g., see The Immunoglobulin Gene Superfamily, A. F. Williams and A. N. Barclay, in Immunoglobulin Genes, T. Honjo, F. W. Alt, and THE. Rabbits, eds., (1989) Academic press: San Diego, Calif., pp. 361-368, which is incorporated herein by reference), most frequently encoded by a rodent, non-human primate, avian, porcine bovine, ovine, goat, or human heavy chain or light chain gene sequence. A functional single-chain antibody generally contains a sufficient portion of a immunoglobulin superfamily gene product so as to retain the property of binding to a specific target molecule, typically a receptor or antigen (epitope).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprise two different specific polynucleotides.

The term "stimulation" as used herein means a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

The term "stimulatory molecule" as used herein means a molecule on a T cell that specifically binds with a cognate stimulatory ligand present on an antigen presenting cell.

The term "stimulatory ligand" as used herein means a ligand that when present on an antigen presenting cell (e.g., a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "target cell" as used herein refers to cells which are involved in a disease and can be targeted by the genetically modified cytotoxic cells of the invention (including but not limited to genetically modified T cells, NK cells, and macrophages). Other target cells will be apparent to those skilled in the art and may be used in connection with alternate embodiments of the invention.

The terms "T cell" and "T-lymphocyte" are interchangeable and used synonymously herein. Examples include, but are not limited to, naive T cells, central memory T cells, effector memory T cells and combinations thereof.

The term "transduction" as used herein refers to the introduction of a foreign nucleic acid into a cell using a viral vector. "Transfection" as used herein refers to the introduction of a foreign nucleic acid into a cell using recombinant DNA technology. The term "transformation" means the introduction of a "foreign" (i.e. extrinsic or extracellular) gene, DNA or RNA sequence to a host cell, so that the host cell will express the introduced gene or sequence to produce a desired substance, such as a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

"Stringent hybridization conditions" means hybridization will occur only if there is at least 90% identity, preferably at least 95% identity and most preferably at least 97% identity between the sequences. See Sambrook et al., Molecular Cloning: a laboratory manual, $2^{nd}$ Ed., Cold Spring Harbor Laboratory Press, 1989, which is hereby incorporated by reference in its entirety.

Also included in the disclosure are polypeptides having sequences that are "substantially identical" to the sequence of an enzyme polypeptide. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site of the molecule, and provided that the polypeptide essentially retains its behavioural properties. For example, one or more amino acids can be deleted from an enzyme polypeptide, resulting in modification of the structure of the polypeptide, without significantly altering its biological activity. For example, amino- or carboxyl-terminal amino acids that are not required for enzyme biological activity can be removed. Such modifications can result in the development of smaller active enzyme polypeptides.

The present disclosure provides a "substantially pure enzyme". The term "substantially pure enzyme" is used herein to describe a molecule, such as a polypeptide (e.g., an enzyme polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The term "treating" includes: (1) preventing or delaying the appearance of clinical symptoms of the state, disorder or condition developing in an animal that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated is either statistically significant or at least perceptible to the patient or to the physician.

"Tumor," as used herein refers to all neoplastic cell growth and proliferation, whether malignant or benign, and all pre-cancerous and cancerous cells and tissues.

As used herein, the term "variable segment" refers to a portion of a nascent peptide which comprises a random, pseudorandom, or defined kernal sequence. A "variable segment" refers to a portion of a nascent peptide which comprises a random pseudorandom, or defined kernal sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

The term "variant" refers to polynucleotides or polypeptides of the disclosure modified at one or more base pairs, codons, introns, exons, or amino acid residues (respectively) of a wild-type protein parent molecule. Variants can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, saturation mutagenesis and any combination thereof. Techniques for producing variant proteins having reduced activity compared to the wild-type protein at a normal physiological condition of e.g., one or more conditions of temperature, pH, osmotic pressure, osmolality, oxidative stress and electrolyte concentration; and enhanced activity at an aberrant condition, are disclosed herein. Variants may additionally be selected for the properties of enhanced chemical resistance, and proteolytic resistance, compared to the wild-type protein.

"Vector", "cloning vector" and "expression vector" as used herein refer to the vehicle by which a polynucleotide sequence (e.g. a foreign gene) can be introduced into a host cell, so as to transform the host and promote expression (e.g. transcription and translation) of the introduced sequence. Vectors include plasmids, phages, viruses, etc.

As used herein, the term "wild-type" means that the polynucleotide does not comprise any mutations. A "wild type protein", "wild-type protein", "wild-type biologic protein", or "wild type biologic protein", refers to a protein which can be isolated from nature that will be active at a level of activity found in nature and will comprise the amino acid sequence found in nature. The wild-type proteins may be human proteins, mammalian proteins, human viral proteins or mammalian proteins. The terms "parent molecule" and "target protein" also refer to the wild-type protein. The wild-type protein preferably has some desired properties, such as a higher binding affinity and/or enzymatic activity, a better stability at a particular temperature and/or pH, improved selectivity and/or solubility. Such wild-type proteins may be obtained by screening a library of proteins for a desired property.

The term "working", as in "working sample", for example, is simply a sample with which one is working. Likewise, a "working molecule", for example is a molecule with which one is working.

DETAILED DESCRIPTION

The present disclosure is directed to methods of engineering or evolving proteins to generate new molecules that are reversibly or irreversibly inactivated at the wild type condition, but active at non-normal conditions at the same or equivalent level as the wild-type condition. These new proteins are referred to as "Mirac" proteins herein. Mirac proteins are particularly valuable for development of novel therapeutics that are active for short or limited periods of time within the host. This is particularly valuable where extended operation of the protein at the given dose would be harmful to the host, but where limited activity is required to perform the desired therapy. Examples of beneficial applications include topical or systemic treatments at high dose, as well as localized treatments in high concentration. Inactivation under the physiological condition can be determined by a combination of the dosing and the rate of inactivation of the protein. This condition based inactivation is especially important for enzyme therapeutics where catalytic activity cause substantial negative effects in a relatively short period of time.

The present disclosure is also directed to methods of engineering or evolving proteins to generate new molecules that are different from wild type molecules in that they are reversibly or irreversibly activated or inactivated over time, or activated or inactivated only when they are in certain microenvironments in the body, including in specific organs in the body (such as the bladder or kidney).

Target Wild-Type Proteins

Any therapeutic protein can serve as a target protein, or wild-type protein, for production of a conditionally active biologic protein. In one aspect, the target protein is a wild-type enzyme. Currently used therapeutic enzymes include urokinase and streptokinase, used in the treatment of blood clots; and hyaluronidase, used as an adjuvant to improve the absorption and dispersion of other drugs, in one aspect, the wild-type protein selected for generation of a conditionally active biologic protein can be a currently used therapeutic enzyme, in order to avoid or minimize deleterious side effects associated with the wild-type protein or enzyme. Alternatively, an enzyme not in current usage as a therapeutic can be selected for generation of a conditionally active biologic protein. Certain non-limiting examples will be discussed in further detail below.

Therapeutic proteins are those which can be used in medicine either alone or in conjunction with other therapies to treat various diseases or medical conditions. The conditionally active biologic proteins of the disclosure could be appropriate for use in one or more indications including the treatment of circulatory disorders, arthritis, multiple sclerosis, autoimmune disorders, cancer, dermatologic conditions and use in various diagnostic formats. Depending on the protein and indication, the conditionally active biologic enzyme protein could be administered in parenteral, topical or oral formulations as discussed below.

Some representative target wild-type proteins include enzymes, antibodies, cytokines, receptors, DNA binding proteins, chelating agents, and hormones. More examples include industrial and pharmaceutical proteins, such as ligands, cell surface receptors, antigens, transcription factors, signaling modules, and cytoskeletal proteins.

Some suitable classes of enzymes are hydrolases such as proteases, carbohydrases, lipases; isomerases such as racemases, epimerases, tautomerases, and mutases; transferases, kinases, oxidoreductases, and phophatases.

The target wild-type proteins can be discovered by generating and screening a library for a protein with a desired property or properties, such as enzymatic activity, binding affinity/selectivity, thermostability, tolerance to high or low pH, expression efficiency, or any other biological activity.

The target wild-type proteins may be discovered by screening a cDNA library. A cDNA library is a combination of cloned cDNA (complementary DNA) fragments inserted into a collection of host cells, which together constitute some portion of the transcriptome of the organism. cDNA is produced from fully transcribed mRNA and therefore contains the coding sequence for expressed proteins of an organism.

In embodiments where the target wild-type proteins are antibodies, the wild-type antibodies can be discovered by generating and screening antibody libraries. The antibody libraries can be either polyclonal antibody libraries or monoclonal antibody libraries. A polyclonal antibody library against an antigen can be generated by direct injection of the antigen into an animal or by administering the antigen to a non-human animal. The antibodies so obtained represent a library of polyclonal antibodies that bind to the antigen. For preparation of monoclonal antibody libraries, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96). Techniques described for the generating single chain antibodies (see, e.g., U.S. Pat. No. 4,946,778) can be adapted to produce single chain antibody library.

There are other methods for generation and screening of antibody libraries for discovery of the wild-type antibody. For example, fully human antibody display libraries can be utilized. Such a library is a population of antibodies displayed on the surface of host cell(s). Preferably, the antibody library is representative of the human repertoire of antibodies in that they have broad capability of binding to a wide range of antigens. Because the antibodies are displayed on the surface of cells, the effective affinity (due to avidity) of each antibody in the library is increased. Unlike other popular library types, such as phage display libraries, where avidity of the antibodies for screening and identification purposes is less desirable, the super avidity provided by cell surface display in the present invention, is desirable. Cell surface display libraries enable the identification of low, medium and high binding affinity antibodies, as well as the identification of non-immunogenic and weak epitopes in the screening or selection step.

Circulatory Disorders-Thrombosis and Thrombolytic Therapy.

A thrombus (blood clot) is defined as a solid mass derived from blood constituents that forms in the circulatory system. The thrombus is formed by a series of events involving blood coagulation factors, platelets, red blood cells, and interactions with the vessel wall. A platelet is an intravascular aggregation of platelets, fibrin and entrapped blood cells which can cause vascular obstruction. By obstructing or blocking blood flow, the thrombus deprives downstream tissue of oxygen supply. Fragments (emboli) of the thrombus may break away and obstruct smaller vessels. Arterial thrombus formation is precipitated by any of a variety of factors including an underlying stenosis-atherosclerosis, a low flow state-cardiac function, hypercoagubility as in cancer or a coagulation factor deficiency, or a foreign body such as a stent or catheter. A thrombus leading to arterial ischemia can result in limb or tissue injury, acute myocardial infarction (AMI), stroke, amputation, or bowel infarction. Major causes of morbidity and mortality are the formation of arterial thrombi (coronary arterial thrombi and cerebral arterial thrombi) and pulmonary thrombi. Venous thrombus formation can occur due to endothelial injury such as trauma, stasis due to e.g. immobility, or hypercoagulability, but atherosclerosos is not a factor. Treatment strategies include mechanical thrombectomy, pharmacomechanical thrombectomy and thrombolysis. Thrombotic therapy is used to minimize formation and aid in removal of thrombi.

Thrombotic therapy includes the use of antiplatelet agents which inhibit platelet activation, anticoagulant therapies, and/or thrombolytic therapy to degrade blood clots. Examples of antiplatelets include aspirin, dipyridamole, and ticlopidine. Examples of anticoagulants include heparin, warfarin, hirudin, and activated human protein C. Examples of thrombolytics include tissue plasminogen activator (tPA)/tPA variants, urokinase and streptokinase. The thrombolytics display a catalytic mode of action.

Thrombolytic therapy in acute myocardial infarction is well established. Use of thrombolytic agents has become standard emergency treatment. Although effective, these products achieve complete reperfusion in only about 50% of patients and side effects include risk of hemorrhage (in particular intracranial bleeding) as well as hypertension. The degradation of blood clots from a damaged or diseased vessel is termed "fibrinolysis" or the "fibrinolytic process". Fibrinolysis is a proteolytic process, by a plasminogen activator which activates the protein plasminogen, thereby forming plasmin. Plasmin proteolytically degrades the fibrin strands of the blood clot to dissolve the clot. Fibrin specific plasminogen activators include tissue plasminogen activators or variants. Non-specific plasminogen activators can include streptokinase and urokinase.

Certain commonly used thrombolytic therapies utilize one of several available tissue plasminogen activator (tPA) variants. For example, tPA based product variants which have been previously approved for use are Alteplase (rt-PA), Reteplase (r-PA) and Tenecteplase (TNK). Approved uses for tPA variants include, for example, acute myocardial infarction for the improvement of ventricular function following AMI, the reduction of incidence of congestive heart failure, and reduction of mortality associated with AMI, management of ischemic stroke in adults for improving neurological recovery and reducing incidence of disability, management of acute massive pulmonary embolism in adults for the lysis of acute pulmonary emboli, and for the lysis of pulmonary emboli accompanied by unstable hemodynamics.

Another commonly used thrombolytic therapy utilizes urokinase. Urokinase is a standard lytic agent used in the management of peripheral vascular disease.

Streptokinase is a protein secreted by several species of streptococci that can bind and activate human plasminogen. Complexes of streptokinase with human plasminogen can hydrolytically activate other unbound plasminogen by activating through bond cleavage to produce plasmin. The usual activation of plasminogen is through the proteolysis of the Arg561-Val562 bond. The amino group of Val562 then forms a salt-bridge with Asp740, which causes a conformational change to produce the active protease plasmin. Plasmin is produced in the blood to break down fibrin, the major constituent of blood clots.

Streptokinase is used as an effective clot-dissolving medication in some cases of myocardial infarction (heart attack), pulmonary embolism (lung blood clots), and deep venous thrombosis (leg blood clots). Streptokinase belongs to a group of medications called fibrinolytics. Streptokinase is given as soon as possible after the onset of a heart attack to dissolve clots in the arteries of the heart wall and reduce damage to the heart muscle. Streptokinase is a bacterial product, so the body has the ability to build up immunity against the protein. Therefore, it is recommended that this product should not be given again after four days from the first administration, as it may not be as effective and cause an allergic reaction. For this reason it is usually given only after a first heart attack, and further thrombotic events are typically treated with tissue plasminogen activator (TPA). Streptokinase is also sometimes used to prevent post-operative adhesions.

Side effects of streptokinase include bleeding (major and minor), hypotension, and respiratory depression as well as possible allergic reaction. In addition, anticoagulants, agents that alter platelet function (e.g. aspirin, other NSAIDs, dipyridamole) may increase risk of bleeding.

Administration of the thrombolytics is generally by infusion or by bolus intravenous dose; or by a mechanical infusion system. Adverse effects can include serious intracranial, gastrointestinal, retroperitoneal, or pericardial bleeding. If bleeding occurs the administration must be discontinued immediately.

In certain embodiments of the disclosure, tPA, streptokinase or urokinase is selected as the target, or wild-type protein.

In one embodiment, the methods of the disclosure are used to select for a conditionally active recombinant or synthetic streptokinase variant with high activity at aberrant temperature conditions below normal physiological conditions; and substantial deactivation or inactivation at normal physiological conditions (e.g. 37 degrees C.). In one aspect, the aberrant temperature condition is room temperature, e.g. 20-25 degrees C. In another aspect, the disclosure provides a method of treating a stroke or heart attack, the method comprising administering a high dose of the conditionally active streptokinase variant to stroke or heart attack victims in order to clear clots, yet allow for rapid inactivation of the streptokinase variant to avoid excessive bleeding.

Circulatory Disorders-Renin/Angiotensin

The renin-angiotensin system is a hormone system that regulates blood pressure and water (fluid) balance. The kidneys secrete renin when the blood volume is low. Renin is an enzyme which hydrolyzes angiotensinogen secreted from the liver into the peptide angiotensin I. Angiotensin I is further cleaved in the lungs by endothelial-bound angiotensin converting enzyme (ACE) into angiotensin II, the most vasoactive peptide. Angiotensin II causes the blood vessels to constrict, resulting in increased blood pressure. However, angiotensin π also stimulates the secretion of the hormone aldosterone from the adrenal cortex. Aldosterone causes the tubules of the kidneys to increase the resorption of sodium and water. This increases the volume of fluid in the body, which also increases blood pressure. An overactive renin-angiotensin system leads to vasoconstriction and retention of sodium and water. These effects lead to hypertension. There are many drugs which interrupt different steps in this system to lower blood pressure. These drugs are one of the main ways to control high blood pressure (hypertension), heart failure, kidney failure, and harmful effects of diabetes.

Hypovolemic shock is an emergency condition in which severe blood and/or fluid loss makes the heart unable to adequately perfuse the body's cells with oxygenated blood. Blood loss can be from trauma, injuries and internal bleeding. The amount of circulating blood may drop due to excessive fluid loss from burns, diarrhea, excessive perspiration or vomiting. Symptoms of hypovolemic shock include anxiety, cool clammy skin, confusion, rapid breathing, or unconsciousness. Examination shows signs of shock including low blood pressure, low body temperature, and rapid pulse, which may be weak or thready. Treatment includes intravenous fluids; blood or blood products; treatment for shock; and medication such as dopamine, dobutamine, epinephrine and norepinephrine to increase blood pressure and cardiac output.

In one embodiment, the disclosure provides a method of selecting for a conditionally active recombinant renin variant to be reversibly deactivated at normal physiological temperature, but reactivated at the aberrant lower temperatures in a patient with hypovolemic shock. The conditionally active protein can be used to treat hypovolemic shock to help increase the volume of fluid in the body, and increase blood pressure.

Circulatory Disorders-Reynaud's Phenomenon

Reynaud's phenomenon (RP) is a vasospastic disorder causing discoloration of the fingers, toes and occasionally other extremities. Emotional stress and cold are classic triggers of the phenomenon. When exposed to cold temperatures, the extremities lose heat. The blood supply to fingers and toes is normally slowed to preserve the body's core temperature. Blood flow is reduced by the narrowing of small arteries under the skin of the extremities. Stress causes similar reaction to cold in the body. Li Reynaud's, the normal response is exaggerated. The condition can cause pain, discoloration, and sensations of cold and numbness. The phenomenon is the result of vasospasms that decrease the blood supply to the respective regions, in Reynaud's disease (Primary Raynaud's phenomenon), the disease is idiopathic. Li Raynaud's syndrome (Secondary Reynaud's), the phenomenon is caused by some other instigating factor. Measurement of hand-temperature gradients is one tool to distinguish between the primary and secondary forms. The primary form can progress to the secondary form, and in extreme cases, the secondary form can progress to necrosis or gangrene of the fingertips.

Raynaud's phenomenon is an exaggeration of responses to cold or emotional stress. Primary RP is essentially mediated by microvascular vasospasm. Hyperactivation of the sympathetic system causes extreme vasoconstriction of the peripheral blood vessels, leading to hypoxia. Chronic, recurrent cases can result in atrophy of the skin, subcutaneous tissue, and muscle. It can also rarely result in ulceration and ischemic gangrene.

Traditional treatment options for Reynaud's phenomenon include prescription medication that dilates blood vessels and promotes circulation. These include calcium channel blockers, such as nifedipine or diltiazem; alpha blockers, which counteract the actions of norepinephrine, a hormone that constricts blood vessels, such as prazosin or doxazosin; and vasodilators, to relax blood vessels, such as nitroglycerin cream, or the angiotensin II inhibitor losartan, sildenafil, or prostaglandins. Fluoxetine, a selective serotonin reuptake inhibitor and other antidepressant medications may reduce the frequency and severity of episodes due to psychological stressors. These drugs may cause side effects such as headache, flushing and ankle edema. A drug may also lose effectiveness over time.

The regulation of cutaneous vasoconstriction and vasodilation involves altered sympathetic nerve activity and a number of neuronal regulators, including adrenergic and non-adrenergic, as well as REDOX signaling and other signaling such as the RhoA/ROCK pathway. Vasoconstriction of vascular smooth muscle cells (vSMC) in the skin is thought to be activated by norepinephrine mediated by alpha1 and alpha2 adrenoreceptors. Alpha2C-ARs translocate from the trans Golgi to the cell surface of the vSMC where they respond to stimulation and signaling of these responses involves the RhoA/Rhokinase (ROCK) signaling pathway. Cold stimulation in cutaneous arteries results in the immediate generation of reactive oxygen species (ROS) in the vSMC mitochondria. ROS are involved in the REDOX signaling through the RhoA/ROCK pathway. RhoA is a GTP-binding protein whose role is the regulation of actin-myosin dependent processes such as migration and cell contraction in vSMC. Non-adrenergic neuropeptides with known function in vasculature with possible involvement in RP include calcitonin gene-related peptide (CGRP), Substance P (SP), Neuropeptide Y (NPY), and vasoactive intestinal peptide (VIP). Fonseca et al., 2009, "Neuronal regulators and vascular dysfunction in Raynaud's phenomenon and systemic sclerosis", *Curr. Vascul. Pharmacol.* 7:34-39.

New therapies for RP include alpha-2c adrenergic receptor blockers, protein tyrosine kinase inhibitors, Rho-kinase inhibitors and calcitonin gene related peptide.

Calcitonin gene related peptide (CGRP) is a member of the calcitonin family of peptides and exists in two forms; alpha-CGRP and beta-CGRP. Alpha-CGRP is a 37-amino acid peptide formed from alternative splicing of the calcitonin/CGRP gene. CGRP is one of the most abundant peptides produced in peripheral and central neurons. It is a potent peptide vasodilator and can function in the transmission of pain. Migraine is a common neurological disorder that is associated with an increase in CGRP levels. CGRP dilates intracranial blood vessels and transmits vascular nociception. CGRP receptor antagonists have been tested as treatments for migraines. Arulmani et al., 2004, "Calcitonin gene-related peptide and it role in migraine pathophysiology", *Eur. J. Pharmacol.* 500(1-3): 315-330. At least three receptor subtypes have been identified and CGRP acts through G protein-coupled receptors whose presence and changes in function modulate the peptide's effect in various tissues. CGRP's signal transduction through the receptors is dependent on two accessory proteins: receptor activity modifying protein 1 (RAMP1) and receptor component protein (RCP). Ghatta 2004, Calcitonin gene-related peptide: understanding its role. *Indian J. Pharmacol.* 36(5): 277-283. One study of the effects of intravenous infusion of three vasodilators: endothelium-dependent vasodilator adenosine triphosphate (ATP), endothelium-independent vasodilator prostacyclin (epoprostenol; PGI2), and CGRP, to patients with Reynaud's phenomenon, and a similar number of age and sex matched controls, using laser Doppler flowmetry (LDF) showed CGRP induced flushing of the face and hands by a rise in skin blood flow in the Reynaud's patients, whereas in controls CGRP caused flushing only in the face. PGI2 caused similar rises in blood flow in hands and face of both groups. ATP did not cause any significant changes in blood flow in hands or face of the patients, but increased blood flow to the face of controls. Shawket et al., 1989, "Selective suprasensitivity to calcitonin-gene-related peptide in the hands in Reynaud's phenomenon". *The Lancet,* 334(8676):1354-1357. In one aspect, the wild-type protein target molecule is CGRP.

In one embodiment, the disclosure provides methods of selecting for conditionally active recombinant protein variants of proteins associated with Reynaud's syndrome to be reversibly deactivated at normal physiological temperature, but reactivated at the aberrant lower temperatures in digits. The conditionally active proteins can be used to treat Reynaud's phenomenon, to prevent or reduce loss of digit function due to low circulation.

Circulatory Disorders—Vasopressin

Arginine vasopressin (AVP, vasopressin, antidiuretic hormone (ADH)) is a peptide hormone found in most mammals that controls reabsorption of molecules in the tubules of the kidney by affecting tissue permeability. One of the most important roles of vasopressin is to regulate water retention in the body. In high concentrations it raises blood pressure by introducing moderate vasoconstriction. Vasopressin has three effects which result in increased urine osmolality (increased concentration) and decreased water excretion. First, vasopressin causes an increase in the permeability of water of the collecting duct cells in the kidney allowing water resorption and excretion of a smaller volume of concentrated urine (antidiuresis). This occurs through insertion of aquaporin-2 water channels into the apical membrane of the collecting duct cells. Secondly, vasopressin causes an increase in the permeability of the inner medullary portion of the collecting duct to urea, allowing increased reabsorption urea into the medullary interstitium. Thirdly, vasopressin causes stimulation of sodium and chloride reabsorption in the thick ascending limb of the loop of Heme by increasing the activity of the $Na^+$—$K^+$-$2Cl''$-cotransporter. NaCl reabsorption drives the process of countercurrent multiplication, which furnishes the osmotic gradient for aquaporin mediated water reabsorption in the medullary collecting ducts.

The hypertonic interstitial fluid surrounding the collecting ducts of the kidney provides a high osmotic pressure for the removal of water. Transmembrane channels made of proteins called aquaporins are inserted in the plasma membrane greatly increasing its permeability to water. When open, an aquaporin channel allows 3 billion molecules of water to pass through each second. Insertion of aquaporin-2 channels requires signaling by vasopressin. Vasopressin binds to receptors (called V2 receptors) on the basolateral surface of the cells of the collecting ducts. Binding of the hormone triggers a rising level of cAMP within the cell. This "second messenger" initiates a chain of events culminating in the insertion of aquaporin-2 channels in the apical surface of the collecting duct cells. The aquaporins allow water to move out of the nephron, increasing the amount of water re-absorbed from the forming urine back into the bloodstream.

The main stimulus for the release of vasopressin from the pituitary gland is increased osmolality of the blood plasma. Anything that dehydrates the body, such as perspiring heavily increases the osmotic pressure of the blood and turns on the vasopres sin to V2 receptor to aquaporin-2 pathway. As a result, as little as 0.5 liters/day of urine may remain of the original 180 liters/day of nephric filtrate. The concentration of salts in urine can be as high as four times that of the blood.

If the blood should become too dilute, as would occur from drinking a large amount of water, vasopressin secretion is inhibited and the aquaporin-2 channels are taken back into the cell by endocytosis. The result is that a large volume of watery urine is formed with a salt concentration as little as one-fourth of that of the blood.

Decreased vasopres sin release or decreased renal sensitivity to AVP leads to diabetes insipidus, a condition featuring hypernatremia (increased blood sodium concentration), polyuria (excess urine production), and polydipsia (thirst).

High levels of AVP secretion (syndrome of inappropriate antidiuretic hormone, SIADH) and resultant hyponatremia (low blood sodium levels) occurs in brain diseases and conditions of the lungs (Small cell lung carcinoma). In the perioperative period, the effects of surgical stress and some commonly used medications (e.g., opiates, syntocinon, antiemetics) lead to a similar state of excess vasopressin secretion. This may cause mild hyponatremia for several days.

Vasopressin agonists are used therapeutically in various conditions, and its long-acting synthetic analogue desmopressin is used in conditions featuring low vasopressin secretion, as well as for control of bleeding (in some forms of von Willebrand disease) and in extreme cases of bedwetting by children. Terlipres sin and related analogues are used as vasoconstrictors in certain conditions. Vasopres sin infusion has been used as a second line of management in septic shock patients not responding to high dose of inotropes (e.g., dopamine or norepinephrine). A vasopressin receptor antagonist is an agent that interferes with action at the vasopressin receptors. They can be used in the treatment of hyponatremia.

In one embodiment, the disclosure provides methods to select for conditionally active biologic recombinant or synthetic protein variants of proteins involved in the vasopressin response to be reversibly deactivated at normal physiological osmotic pressure, but reactivated at aberrant osmotic pressure in the blood. In another embodiment, variants of proteins involved in the vasopressin response are activated under hyponatremic conditions, but inactivated at normal serum sodium concentrations. In one aspect, hyponatremic conditions are those where serum sodium <135 mEq/L.

Cancer-Angiostatin

Angiostatin is a naturally occurring protein in several animal species. It acts as an endogenous angiogenesis inhibitor (i.e., it blocks the growth of new blood vessels). Angiostatin is able to suppress tumor cell growth and metastasis through inhibition of endothelial cell proliferation and migration. Angiostatin is a 38 kD fragment of plasmin (which is itself a fragment of plasminogen). Angiostatin comprises the kringles 1 to 3 of plasminogen. Angiostatin is produced, for example, by autolytic cleavage of plasminogen, involving extracellular disulfide bond reduction by phosphoglycerate kinase. Angiostatin can also be cleaved from plasminogen by different matrix metalloproteinases (MMPs) including MMP2, MMP 12 and MMP9, and serine proteases (neutrophil elastase, prostate-specific antigen (PSA)). In vivo angiostatin inhibits tumor growth and keeps experimental metastasis in a dormant state. Angiostatin is elevated in animals with primary tumors and other inflammatory and degenerative diseases.

Angiostatin is known to bind many proteins including angiomotin and endothelial cell surface ATO synthase, but also integrins, annexin II, C-met receptor, NG2-proteoglycans, tissue-plasminogen activator, chondroitin sulfate glycoproteins, and CD26. One study shows that IL-12, a TH1 cytokine with potent antiangiogenic activity, is a mediator of angiostatin's activity. Albin"., *J. Translational Medicine*. Jan. 4, 2009, 7:5. Angiostatin binds and inhibits ATP synthase on the endothelial cell surface. ATP synthase also occurs on the surface of a variety of cancer cells. Tumor cell surface ATP synthase was found to be more active at low extracellular pH; a hallmark of tumor microenvironment. Angiostatin was found to affect tumor cell surface ATP synthase activity at acidic extracellular pH (pHe). At low extracellular pH, angiostatin was directly anti-tumorigenic. At low pH, angiostatin and anti-beta-subunit antibody induce intracellular acidification of A549 cancer cells, as well as a direct toxicity that is absent in tumor cells with low levels of extracellular ATP synthase. It was hypothesized that the mechanism of tumor cytotoxicity is dependent on intracellular pH deregulation due to inhibition of cell surface ATP synthase. Chi and Pizzo, "Angiostatin is directly cytotoxic to tumor cells at low extracellular pH: a mechanism dependent on cell surface-associated ATP synthase", *Cancer Res.,* 2006, 66(2): 875-82.

In one embodiment, the disclosure provides a method for identification of conditionally active angiostatin variant which is less active than wild-type angiostatin at normal physiological blood pH, but exhibits enhanced activity at low pH. Low pH is defined as being less than normal physiological pH. In one aspect, low pH is less than about pH 7.2. In a particular aspect, low pH is about pH 6.7.

In one aspect, the conditionally active angiostatin variant can be formulated and utilized as an anticancer agent.

Enhancement of Tissue Permeability—Hyaluronidase

Hyaluronidases are a family of enzymes that degrade hyaluronic acid. By catalyzing the degradation of hyaluronic acid, a major constituent of the interstitial barrier, hyaluronidase lowers the viscosity of hyaluronic acid, thereby increasing tissue permeability. It is used in medicine in conjunction with drugs to speed their dispersion and delivery. The most common application is in ophthalmic surgery, used in combination with local anesthetics. Animal derived hyaluronidase include Hydase™ (PrimaPharm Inc.; Akorn me), Vitrase (ISTA Pharmaceuticals) and Amphadase (Amphastar Pharmaceuticals). Human Recombinant Hyaluronidase is currently approved as an adjuvant to increase absorption of other drugs; hypodermocyclis (subcutaneous infusion of fluids); adjunct in subcutaneous urography to improve resorption of radioopaque agents. (Hylenex; Halozyme Therapeutics, Inc.; Baxter Healthcare Corp.) In one embodiment, hyaluronidase can serve as a wild-type protein (parent molecule) for preparation of a conditionally active biologic protein. Hyaluronidases may play a role in cancer metastasis and perhaps angiogenesis; therefore overexposure to these enzymes could be deleterious, in one aspect, a conditionally active biologic hyaluronidase protein would become irreversibly or reversibly inactivated at normal physiological temperature, but would be active at a level equal to or exceeding that of the wild-type hyaluronidase at certain temperature ranges below that of normal physiological temperature.

Autoimmune Diseases—Conditionally Active Biologic Response Modifiers

Rheumatoid arthritis is an autoimmune disease characterized by aberrant immune mechanisms that lead to joint inflammation and swelling with progressive destruction of the joints. RA can also affect the skin, connective tissue and organs in the body. Traditional treatment includes non-steroidal anti-inflammatory drugs (NSAIDS), COX-2 inhibitors, and disease-modifying anti-rheumatic drugs (DMARDS) such as methotrexate. None of the traditional treatment regimes is ideal, especially for long term use.

Biologic response modifiers, which target inflammatory mediators, offer a relatively new approach to the treatment of rheumatoid arthritis and other autoimmune diseases. Such biologic response modifiers include antibodies, or active portions thereof, against various inflammatory mediators such as IL-6, IL-6 receptor, TNF-alpha, IL-23 and IL-12.

Some of the first biologic response modifiers were medications targeting tumor necrosis factor alpha (TNF-a), a pro-inflammatory cytokine involved in the pathogenesis of RA. Several anti-TNF-alpha medications are currently marketed for the treatment of RA. For example, Enbrel® (etanercept, Amgen) is a TNF-alpha blocker. Etanercept is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. Etanercept is produced in a Chinese hamster ovary (CHO) mammalian cell expression system. It consists of 934 amino acids and an apparent molecular weight of about 150 kilodaltons. Enbrel® is used to treat rheumatoid arthritis, psoriatic arthritis, ankylosing spondylitis and plaque psoriasis. Serious side effects of Enbrel® include infections including tuberculosis, fungal infection, bacterial or viral infection due to opportunistic pathogens. Sepsis can also occur. Lymphoma, or other malignancies have also been reported.

Remicade® (infliximab) is a chimeric anti-TNF-alpha IgGkI monoclonal antibody composed of human constant and murine variable regions. Remicade is administered by intravenous injection and is used to treat rheumatoid arthritis, psoriasis, Crohn's disease, ulcerative colitis, and ankylosing spondylitis. Side effects of Remicade include serious infection or sepsis, and rarely certain T-cell lymphomas. Other side effects include hepatotoxicity, certain severe hematologic events, hypersensitivity reactions and certain severe neurological events.

Other biologic response modifiers include humanized anti-interleukin-6 (IL-6) receptor antibodies. IL-6 is a cytokine that contributes to inflammation, swelling and joint damage in RA. One humanized anti-IL-6 receptor antibody, Actemra (tocilizumab, Roche), is approved by the FDA and European Commission to treat adult patients with rheumatoid arthritis. Actemra is also approved in Japan for treatment of RA and juvenile idiopathic arthritis (sJIA). Phase III studies showed that treatment with Actemra as a monotherapy, or a combination with MTX or other DMARDs, reduced signs and symptoms of RA compared with other therapies. Actemra is a humanized anti-human IL-6 receptor monoclonal antibody that competitively blocks the binding of IL-6 to its receptor. Thus, it inhibits the proliferative effects of IL-6, which lead to synovial thickening and pannus formation in RA. Serious side effects of Actemra, include serious infections and hypersensitivity reactions including a few cases of anaphylaxis. Other side effects include upper respiratory tract infection, headache, nasopharyngitis, hypertension and increased ALT.

Another common autoimmune disease is psoriasis. An overactive immune system can lead to high levels of IL-12 and IL-23, two cytokine proteins that have been found in psoriatic skin plaques. IL-12 and IL-23 are involved in inflammatory and immune responses such as natural killer cell activation and CD4+ T-cell differentiation and activation.

One treatment for moderate or severe psoriasis involves subcutaneous injection of Stelara™ (ustekinumab, Centocor Ortho Biotech, Inc.) a humanized IgGIk monoclonal antibody against the p40 subunit of the IL-12 and IL-23 cytokines. Stelara has been shown to provide relief from certain symptoms associated with psoriatic plaques, such as plaque thickness, scaling and redness. The formulation for Stelara includes L-histidine and L-histidine monohydrochloride monohydrate, polysorbate 80, and sucrose in aqueous solution. Use of Stelara™ affects the immune system, and may increase chances of infection, including tuberculosis, and infections caused by bacteria, fungi or viruses; as well as increase the risk of certain types of cancer.

Side effects of the biologic response modifiers are significant and are caused in part by high levels following injection into patients renders patients susceptible to serious infection or death. This is a major side effect associated with this important class of drugs. One challenge is avoiding the high initial level of activity from the dose of antibody required to provide a long treatment effect following injection.

In one embodiment, the disclosure provides a method to prepare a conditionally active biologic response mediator, or fragment thereof, that avoids the high level of activity from the dose of antibody required to provide a long treatment effect following injection. The method of the disclosure can be used to design antibodies to inflammatory mediators such as IL-6, IL-6 receptor, TNF-alpha, IL-23 and IL-12 that are inactive at dosing conditions such as room temperature, but slowly refold (reversibly or irreversibly) at body temperature. These antibodies or fragments thereof would be inactive upon initial injection, but would refold or reactivate over a period of hours to days when exposed to blood following injection. This could allow higher dosing, and a longer half-life (or periods between dosing) with reduced side effects.

In one aspect, the disclosure provides a method for preparation of a conditionally active antibody to an inflammatory mediator, or fragment thereof, that is inactive at dosing conditions such as room temperature, but slowly refold (reversibly or irreversibly) at body temperature. The method comprises the following steps. Selecting an inflammatory mediator. Screening to identify an antibody to the inflammatory mediator via hybridoma. Humanizing the anti-inflammatory mediator antibody. Evolving the anti-inflammatory mediator antibody and screening differentially for binding at two or more conditions, for example, two or more temperature conditions such as at room temperature and at 37° C. or higher; selecting for mutations that exhibit at least one of: (a) a decrease in activity in the assay at the normal physiological condition compared to the wild-type protein, and (b) an increase in activity in the assay under the aberrant condition compared to the wild-type protein. The up-mutants identified in the heavy and light changes are then recombined within the heavy and light chains, as well as through combinatorial association of the heavy and light chains. Screening of these recombined heavy and light chains is repeated at the two conditions, for example, room temperature and at 37° C. or higher. In addition, the recombined antibodies or fragments can be screened for activity and stability under storage and physiological conditions.

Alternatively, the wild-type antibody to the inflammatory mediator is a known antibody or variant or active fragment thereof.

In one aspect, the first and second conditions are selected from conditions of pH, osmotic pressure, osmolality, oxidative stress and electrolyte concentration. In another aspect, the inflammatory mediator is selected from IL-6, IL-6 receptor, TNF-alpha, IL-23 and IL-12.

In another aspect, the disclosure provides a method for preparation of a conditionally active antibody to IL-6, or fragment thereof, that is inactive at dosing conditions such as room temperature, but slowly refold (reversibly or irreversibly) at body temperature. The method comprises the following steps. Screening a fully human library for an antibody to IL-6. Evolving the IL-6 antibody and screening differentially for molecules at room temperature and at 37° C. or higher; selecting for mutations that exhibit at least one of: (a) a decrease in activity in the assay at the normal physiological condition compared to the wild-type protein, and (b) an increase in activity in the assay under the aberrant condition compared to the wild-type protein. The up-mutants identified in the heavy and light changes are then recombined within the heavy and light chains, as well as through combinatorial association of the heavy and light chains. Screening of these recombined heavy and light chains is repeated at room temperature and the higher temperature. In addition, the recombined antibodies or fragments are tested for activity and stability under storage and physiological conditions.

The conditionally active anti-IL-6 antibodies thus identified and produced can be used in a method to treat an autoimmune disease, such as rheumatoid arthritis or psoriasis, by administration of an effective amount to a patient in need thereof, with a reduction in the severity of side effects compared to administration of a traditional biologic response modifier anti-IL-6 antibody. One advantage of this method is that it allows for smoothing or leveling of the drug quantity over the period of treatment relative to the current high level of biologic response modifier drug followed by half-life clearance over weeks or months.

One or more mutagenesis techniques are employed to evolve the DNA which encodes the wild-type protein to create a library of mutant DNA; the mutant DNA is expressed to create a library of mutant proteins; and the library is subjected to a screening assay under a normal physiological condition and under one or more aberrant conditions. Conditionally active biologic proteins are selected from those proteins which exhibit at least one of: (a) a decrease in activity in the assay at the normal physiological condition compared to the wild-type protein, and (b) an increase in activity in the assay under the aberrant condition compared to the wild-type protein. Alternatively, conditionally active biologic proteins are selected from those proteins which exhibit changes in activity, reversibly or irreversibly, in two or more different physiological conditions.

Conditionally Active Viral Particles

Viral particles have long been used as delivery vehicles for transporting proteins, nucleic acid molecules, chemical compounds or radioactive isotopes to a target cell or tissue. Viral particles that are commonly used as delivery vehicles include retroviruses, adenoviruses, lentivirus, herpes virus, and adeno-associated viruses. The viral particles recognize their target cells through a surface protein that serves as a recognition protein for specific binding to a cellular protein that serves as target protein of the target cells, often in a ligand-receptor binding system (Lentz, "The recognition event between virus and host cell receptor: a target for antiviral agents," *J. of Gen. Viral.*, vol. 71, pages 751-765, 1990, incorporated herein by reference). For example, the viral recognition protein may be a ligand for a receptor on the target cells. The specificity between a ligand and a receptor allows the viral particles to specifically recognize and deliver their content to a target cell.

Techniques for developing artificial viral particles from wild-type viruses are well known to a person skilled in the art. Known artificial viral particles as delivery vehicles include those based on retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus (e.g., Sindbis virus vectors, Semliki forest virus (ATCC VR-67; ATCC VR-1247), Ross River virus (ATCC VR-373; ATCC VR-1246), Venezuelan equine encephalitis virus (ATCC VR-923; ATCC VR-1250; ATCC VR 1249; ATCC VR-532)), and adeno-associated viruses (see, e.g., WO 94/12649, WO 93/03769; WO 93/19191; WO 94/28938; WO 95/11984 and WO 95/00655).

Generally, the artificial viral particles are constructed by inserting a foreign recognition protein into a virus particle, often replacing the native recognition protein by recombinant technology. The foreign recognition protein may be, for example, an antibody, a receptor, a ligand or a collagen binding domain. The present invention provides a conditionally active recognition protein that is inactive or less active for binding to a cell at a normal physiological condition, and that is active or more active for binding to a cell at an aberrant condition. The conditionally active recognition protein can thereby preferentially bind to target cells of diseased tissue and/or at a disease site based on the presence of an abnormal condition at that site and avoid or only minimally bind to the cells of normal tissue where a normal physiological condition exists. The conditionally active recognition protein may be expressed and displayed on the surface of a viral particle.

In some embodiments, the present invention provides a method of evolving a wild-type recognition protein and screening for a conditionally active recognition protein. The conditionally active recognition protein is less active in binding to a cell than the wild-type recognition protein under a normal physiological condition, and more active in binding to a cell than the wild-type recognition protein under an aberrant condition. Such a conditionally active recognition protein may be inserted into a viral particle by well-known recombinant technology to generate a conditionally active viral particle.

In another embodiment, the present invention provides a conditionally active viral particle comprising a conditionally active recognition protein, which allows the conditionally active viral particle to recognize and bind with the target cells of diseased tissue or at a disease site, but not the cells of normal tissue. Such a conditionally active viral particle can preferentially deliver therapeutics within the viral particle to the diseased tissue or disease site, while the conditionally active viral particle delivers less or does not deliver any of the therapeutic composition to the cells of normal tissue.

In some embodiments, the target cells at a disease site are inside a zone or microenvironment with an abnormal pH (e.g., pH 6.5) or an abnormal temperature, in comparison with the pH or temperature in other parts of the body that are healthy or not suffering from the particular disease or disease state. In this embodiment, the conditionally active recognition protein is less active than a wild-type recognition protein in binding with a target protein of a target cell at a normal physiological pH or temperature, and more active than a wild-type recognition protein in binding with the target protein of a target cell at an abnormal or aberrant pH or temperature. In this manner, the recognition protein will preferentially bind at a site where an abnormal pH or temperature is encountered thereby delivering a treatment to the site of a disease.

In one embodiment, the viral particle may comprise a conditionally active antibody of the present invention, and especially the variable region of an antibody (e.g., Fab, Fab', Fv). Such a conditionally active antibody can bind to the target protein (as antigen) of a target cell with lower affinity than a wild-type antibody under a normal physiological condition which may be encountered at a location with normal tissue, and a higher affinity than the wild-type antibody under an abnormal or aberrant condition which may be encountered at a disease site or at diseased tissue. The conditionally active antibody may be derived from the wild-type antibody according to the method of the present invention.

In an embodiment, the target protein on the target cell includes tyrosine kinase growth factor receptors such as those which are overexpressed on the cell surface in, for example, many tumors. Exemplary tyrosine kinase growth factors are VEGF receptors, FGF receptors, PDGF receptors, IGF receptors, EGF receptors, TGF-alpha receptors, TGF-beta receptors, HB-EGF receptors, ErbB2 receptors, ErbB3 receptors, and ErbB4 receptors.

Conditionally Active DNA/RNA Modifying Proteins

DNA/RNA modifying proteins have been discovered as a form of new genome-engineering tools, particularly one called CRISPR, which can allow researchers to perform microsurgery on genes, precisely and easily changing a DNA sequence at exact locations on a chromosome (genome editing, Mali et al., "Cas9 as a versatile tool for engineering biology," *Nature Methods*, vol. 10, pages 957-963, 2013). For example, sickle-cell anemia is caused by a single base mutation, which can potentially be corrected using DNA/RNA modifying proteins. The technology may precisely delete or edit bits of a chromosome, even by changing a single base pair (Makarova et al., "Evolution and classification of the CRISPR-Cas systems," *Nature Reviews Microbiology*, vol. 9, pages 467-477, 2011).

Genome editing with CRISPR has the ability to quickly and simultaneously make multiple genetic changes to a cell. Many human illnesses, including heart disease, diabetes, and neurological diseases, are affected by mutations in multiple genes. This CRISPR-based technology has the potential to reverse the disease causing mutations and cure these diseases or at least reduce the severity of these diseases. Genome editing relies on CRISPR associated (Cas) proteins (a family of enzymes) for cutting the genomic DNA. Typically, the Cas protein is guided by a small guide RNA to a targeted region in the genome, where the guide RNA matches the target region. Because the Cas protein has little or no sequence specificity, the guide RNA serves as a pointer for the Cas protein to achieve precise genome editing. In one embodiment, one Cas protein may be used with multiple guide RNAs to simultaneously correct multiple gene mutations.

There are many Cas proteins. Examples include Cas1, Cas2, Cas3', Cas3", Cas4, Cas5, Cas6, Cas6e, Cas6f, Cas7, Cas8a1, Cas8a2, Cas8b, Cas8c, Cas9, Cas10, Cas10d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 ((Makarova et al., "Evolution and classification of the CRISPR-Cas systems," *Nature Reviews Microbiology*, vol. 9, pages 467-477, 2011).

To conduct genome editing, the Cas protein has to enter the target cell. Cells in a subject may have a different intracellular pH inside of the cells. Some cells in diseased tissue have an abnormal intracellular pH. For example, some tumor cells tend to have an alkaline intracellular pH of about 7.12-7.65, while cells in normal tissue have a neutral intracellular pH ranging from 6.99-7.20. See Cardone et al., "The role of disturbed pH dynamics and the Na(+)/H(+) exchanger in metastasis," *Nat. Rev. Cancer*, vol. 5, pages 786-795, 2005. In chronic hypoxia, the cells in diseased tissue have an intracellular pH of about 7.2-7.5, also higher than the intracellular of normal tissue (Rios et al., "Chronic hypoxia elevates intracellular and activates Na+/H+ exchange in pulmonary arterial smooth muscle cells," *American Journal of Physiology—Lung Cellular and Molecular Physiology*, vol. 289, pages L867-L874, 2005). Further, in ischemia cells, the intracellular pH is typically in a range of 6.55-6.65, which is lower than the intracellular pH of normal tissue (Haqberg, "Intracellular pH during ischemia in skeletal muscle: relationship to membrane potential, extracellular pH, tissue lactic acid and ATP," *Pflugers Arch.*, vol. 404, pages 342-347, 1985). More examples of abnormal intracellular pH in diseased tissue are discussed in Han et al., "Fluorescent Indicators for Intracellular pH," *Chem Rev.*, vol. 110, pages 2709-2728, 2010.

The present invention provides a method for producing a conditionally active Cas protein from a wild-type Cas protein, where the conditionally active Cas protein has at least one of a decreased enzymatic activity relative to the activity of the wild-type Cas protein under a normal physiological condition inside a normal cell, and an increased enzymatic activity relative to the activity of the wild-type Cas protein under an aberrant condition inside a target cell such as one of the diseased cells discussed above. In some embodiments, the normal physiological condition is an intracellular pH that is about neutral, and the aberrant condition is a different intracellular pH that is typically above or below neutral. In an embodiment, the aberrant condition is an intracellular pH of from 7.2 to 7.65 or an intracellular pH of from 6.5-6.8.

In some embodiments, the conditionally active Cas protein may be delivered to a target cell using the conditionally active viral particle of the present invention. The conditionally active viral particle may comprise the conditionally active Cas protein and at least one guide RNA for directing the Cas protein to the location at which Cas protein will edit the genomic DNA.

Conditionally Active Chimeric Antigen Receptor

In some embodiments, the present disclosure is directed to a chimeric antigen receptor (CAR) for binding with a target antigen, comprising at least one antigen specific targeting region (ASTR), a transmembrane domain (TM); and an intracellular signaling domain (ISD). In some embodiments, the CAR may further comprise an extracellular spacer domain (ESD) and/or a co-stimulatory domain (CSD). See FIG. 1. These CARs can direct cytotoxic cells (that express the CARs) to a disease site for attacking diseased cells such as cancer cells. The cytotoxic cells may be used for targeting and destroying diseased tissue and/or pathogens. Using these cytotoxic cells to remove unwanted tissue (i.e. target tissue) such as tumors is a promising therapeutic approach. Other tissues that may be targeted for removal include glandular (e.g. prostate) hyperplasia, warts, and unwanted fatty tissue.

Cytotoxic cells expressing chimeric antigen receptors can significantly improve the specificity and sensitivity of the cytotoxic cells. For example, T cells expressing a CAR (CAR-T cells) are capable of using the CAR to direct the T cells to target tumor cells expressing a cell surface antigen that specifically binds to the CAR. Such CAR-T cells can deliver the cytotoxic agent more selectively to the tumor cells. CAR-T cells can directly recognize a target molecule and thus are typically not restricted by polymorphic presenting elements such as human leukocyte antigens (HLAs). The advantages of this CAR targeting strategy are threefold. First, since the function of the CAR-T cell is not dependent upon HLA status, the same CAR-based approach can be used in all patients with tumors that express the same target surface antigen. Second, corruption of antigen processing and presenting machinery is a common attribute of tumor cells and may facilitate immune escape. However, this affords no protection against CAR-T cells. Third, a range of macromolecules can be targeted using this system, including proteins, carbohydrates, and glycolipids.

The ASTR is an extracellular region of the CAR for binding to a specific target antigen including proteins, carbohydrates, and glycolipids. In some embodiments, the ASTR comprises an antibody, especially a single-chain antibody, or a fragment thereof. The ASTR may comprise a full length heavy chain, an Fab fragment, a single chain Fv (scFv) fragment, a divalent single chain antibody or a diabody, each of which are specific to the target antigen.

The ASTR may also comprise another protein functional domain to recognize and bind to the target antigen. Because the target antigen may have other biological functions, such as acting as a receptor or a ligand, the ASTR may alternatively comprise a functional domain for specifically binding with the antigen. Some examples of proteins with functional domains include linked cytokines (which leads to recognition of cells bearing the cytokine receptor), affibodies, ligand binding domains from naturally occurring receptors, and soluble protein/peptide ligands for a receptor, for example on a tumor cell. In fact, almost any molecule that is capable of binding to a given antigen with high affinity can be used in the ASTR, as will be appreciated by those skilled in the art.

In one embodiment, the CAR of the invention comprises at least two ASTRs which target at least two different antigens or two epitopes on the same antigen. In an embodiment, the CAR comprises three or more ASTRs which target at least three or more different antigens or epitopes. When a plurality of ASTRs is present in the CAR, the ASTRs may be arranged in tandem and may be separated by linker peptides (FIG. 1).

In one embodiment, the ASTR comprises a full-length IgG heavy chain that is specific for the target antigen and has the $V_H$, CH1, hinge, and the CH2 and CH3 (Fc) Ig domains, if the $V_H$ domain alone is sufficient to confer antigen-specificity ("single-domain antibodies"). If both, the $V_H$ and the $V_L$ domains are necessary to generate a fully active ASTR, the $V_H$-containing CAR and the full-length lambda light chain (IgL) are both introduced into the same cytotoxic cell to generate an active ASTR. In another embodiment, each ASTR of the CAR comprises at least two single chain antibody variable fragments (scFv), each specific for a different target antigen. scFvs, in which the C-terminus of one variable domain ($V_H$ or $V_L$) is tethered to the N-terminus of the other variable domain ($V_L$ or $V_H$, respectively) via a polypeptide linker. Such antibody fragments have been developed without significantly disrupting antigen binding or specificity of the binding (Chaudhary et al., "A recombinant single-chain immunotoxin composed of anti-Tac variable regions and a truncated diphtheria toxin," *Proc. Natl. Acad. Sci.*, vol. 87, page 9491, 1990; Bedzyk et al., "Immunological and structural characterization of a high affinity anti-fluorescein single-chain antibody," *J. Biol. Chem.*, vol. 265, page 18615, 1990). These scFvs lack the constant regions (Fc) present in the heavy and light chains of a native antibody. The scFvs, specific for at least two different antigens, are arranged in tandem. In an embodiment, an extracelluar spacer domain may be linked between the ASTR and the transmembrane domain.

In another embodiment, an scFv fragment may be fused to all or a portion of the constant domains of the heavy chain. In a further embodiment, an ASTR of the CAR comprises a divalent (or bivalent) single-chain variable fragment (di-scFvs, bi-scFvs). In CARs comprising di-scFVs, two scFvs each specific for an antigen are linked together to form a single peptide chain with two $V_H$ and two $V_L$ regions (Xiong et al., "Development of tumor targeting anti-MUC-1 multimer: effects of di-scFv unpaired cysteine location on PEGylation and tumor binding," *Protein Engineering Design and Selection*, vol. 19, pages 359-367, 2006; Kufer et al., "A revival of bispecific antibodies," *Trends in Biotechnology*, vol. 22, pages 238-244, 2004).

In yet another embodiment, an ASTR comprises a diabody. In a diabody, the scFvs are created with linker peptides that are too short for the two variable regions to fold together, driving the scFvs to dimerize. Still shorter linkers (one or two amino acids) lead to the formation of trimers, the so-called triabodies or tribodies. Tetrabodies may also be used in the ASTR.

When two or more ASTRs are present in a CAR, the ASTRs are connected to each other covalently on a single polypeptide chain, through an oligo- or polypeptide linker, an Fc hinge or a membrane hinge region.

The antigens targeted by the CAR are present on the surface or inside of cells in tissue that is targeted for removal, such as tumors, glandular (e.g. prostate) hyperplasia, warts, and unwanted fatty tissue. While the surface antigens are more efficiently recognized and bound by the ASTR of CARs, intracellular antigens may also be targeted by the CARs. In some embodiments, the target antigens are preferably specific for cancer, inflammatory disease, neuronal-disorders, diabetes, cardiovascular disease, or infectious diseases. Examples of target antigens include antigens expressed by various immune cells, carcinomas, sarcomas, lymphomas, leukemia, germ cell tumors, blastomas, and cells associated with various hematologic diseases, autoimmune diseases, and/or inflammatory diseases.

Antigens specific for cancer which may be targeted by the ASTR include one or more of 4-IBB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, LI-CAM, IL-13, IL-6, insulin-like growth factor I receptor, integrin $\alpha 5\beta 1$, integrin $\alpha v\beta 3$, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, ROR1, SCH 900105, SDC1, SLAMF7, TAG-72, tenascin C, TGF beta 2, TGF-$\beta$, TRAIL-R1, TRAIL-R2, tumor antigen CTAA16.88, VEGF-A, VEGFR-1, VEGFR2 or vimentin.

Antigens specific for inflammatory diseases which may be targeted by the ASTR include one or more of AOC3 (VAP-1), CAM-3001, CCL11 (eotaxin-1), CD125, CD147 (basigin), CD154 (CD40L), CD2, CD20, CD23 (IgE receptor), CD25 (a chain of IL-2 receptor), CD3, CD4, CD5, IFN-a, IFN-γ, IgE, IgE Fc region, IL-1, IL-12, IL-23, IL-13, IL-17, IL-17A, IL-22, IL-4, IL-5, IL-5, IL-6, IL-6 receptor, integrin a4, integrin α4β7, Lama glama, LFA-1 (CD11a), MEDI-528, myostatin, OX-40, rhuMAb β7, scleroscin, SOST, TGF beta 1, TNF-a or VEGF-A.

Antigens specific for neuronal disorders which may be targeted by the ASTR of the invention include one or more of beta amyloid or MABT5102A. Antigens specific for diabetes which may be targeted by the ASTR of the invention include one or more of L-Iβ or CD3. Antigens specific for cardiovascular diseases which may be targeted by the ASTR of the invention include one or more of C5, cardiac myosin, CD41 (integrin alpha-lib), fibrin II, beta chain, ITGB2 (CD 18) and sphingosine-1-phosphate.

Antigens specific for infectious diseases which may be targeted by the ASTR of the invention include one or more of anthrax toxin, CCR5, CD4, clumping factor A, cytomegalovirus, cytomegalovirus glycoprotein B, endotoxins, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-a.

Further examples of target antigens include surface proteins found on cancer cells in a specific or amplified fashion, e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas, or viral proteins, e.g. gp120 and gp41 envelope proteins of HIV, envelope proteins from the Hepatitis B and C viruses, glycoprotein B and other envelope glycoproteins of human cytomegalovirus, and the envelope proteins from oncoviruses such as Kaposi's sarcoma-associated Herpes virus. Other potential target antigens include CD4, where the ligand is the HIV gp120 envelope glycoprotein, and other viral receptors, for example ICAM, which is the receptor for the human rhinovirus, and the related receptor molecule for poliovirus.

The extracellular spacer domain of the CAR is a hydrophilic region which is located between the ASTR and the transmembrane domain. In some embodiments, this domain facilitates proper protein folding for the CAR. The extracellular spacer domain is an optional component of the CAR. The extracellular spacer domain may comprise a domain selected from Fc fragments of antibodies, hinge regions of antibodies, CH2 regions of antibodies, CH3 regions of antibodies, artificial spacer sequences or combinations thereof. Examples of extracellular spacer domains include the CD8a hinge, artificial spacers made of polypeptides which may be as small as, three glycines (Gly), as well as CH1 and CH3 domains of IgGs (such as human IgG4).

The transmembrane domain of the CAR is a region that is capable of spanning the plasma membrane of the cytotoxic cells. The transmembrane domain is selected from a transmembrane region of a transmembrane protein such as, for example, Type I transmembrane proteins, an artificial hydrophobic sequence or a combination thereof. Examples of the transmembrane domain include the transmembrane regions of the alpha, beta or zeta chain of the T cell receptor, CD28, CD3 epsilon, CD45, CD4, CD5, CD8, CD9, CD16, CD22, CD33, CD37, CD64, CD80, CD86, CD134, CD137, CD154. Synthetic transmembrane domains may comprise a triplet of phenylalanine, tryptophan and valine. Optionally, a short oligo- or polypeptide linker, preferably between 2 and 10 amino acids in length, may form the linkage between the transmembrane domain and the intracellular signaling domain of the CAR. A glycine-serine doublet provides a particularly suitable linker between the transmembrane domain and the intracellular signaling domain.

The CAR of the invention also comprises an intracellular signaling domain. The intracellular signaling domain transduces the effector function signal and directs the cytotoxic cell to perform its specialized function, i.e., harming and/or destroying the target cells. Examples of the intracellular signaling domain include the chain of the T cell receptor complex or any of its homologs, e.g., η chain, FcsRIy and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T cell transduction, such as CD2, CD5 and CD28. Specifically, the intracellular signaling domain may be human CD3 zeta chain, FcyRIII, FcsRI, cytoplasmic tails of Fc receptors, an immunoreceptor tyrosine-based activation motif (ITAM) bearing cytoplasmic receptors and combinations thereof.

In some embodiments, the intracellular signaling domain comprises a cytoplasmic signaling domain of TCR zeta, FcR gamma, FcR beta, CD3 gamma, CD3 delta, CD3 epsilon, CD5, CD22, CD79a, CD79b, or CD66d. It is particularly preferred that the intracellular signaling domain in the CAR comprises a cytoplasmic signaling domain of human CD3 zeta.

The CAR of the present invention may comprise a co-stimulatory domain, which has the function of enhancing cell proliferation, cell survival and development of memory cells for the cytotoxic cells that express the CAR. The CAR of the invention may comprise one or more co-stimulatory domains selected from co-stimulatory domains of proteins in the TNFR superfamily, CD28, CD137 (4-1BB), CD134 (OX40), Dap1O, CD27, CD2, CD7, CD5, ICAM-1, LFA-1 (CD11a/CD18), Lck, TNFR-I, PD-1, TNFR-II, Fas, CD30, CD40, ICOS LIGHT, NKG2C, B7-H3, or combinations thereof. If the CAR comprises more than one co-stimulatory domain, these domains may be arranged in tandem, optionally separated by a linker. The co-stimulatory domain is an intracellular domain that may locate between the transmembrane domain and the intracellular signaling domain in the CAR.

In some embodiments, two or more components of the CAR of the invention are separated by one or more linkers. For example, in a CAR comprising at least two ASTRs, the two ASTRs may be separated by a linker. Linkers are oligo- or polypeptide regions of from about 1 to 100 amino acids in length. In some embodiments, the linkers may be, for example, 5-12 amino acids in length, 5-15 amino acids in length or 5 to 20 amino acids in length. Linkers may be composed of flexible residues like glycine and serine so that the adjacent protein domains are free to move relative to one another. Longer linkers, for example those longer than 100 amino acids, may be used in connection with alternate embodiments of the invention, and may be selected to, for example, ensure that two adjacent domains do not sterically interfere with one another. Examples of linkers which may be used in the instant invention include but are not limited to 2A linkers (for example T2A), 2A-like linkers or functional equivalents thereof.

The present invention provides a conditionally active chimeric antigen receptor for binding with a target antigen, where the antigen specific targeting region is evolved from a wild-type protein or a domain thereof and has at least one of: (a) a decrease in activity in the assay at the normal physiological condition compared to the wild-type protein, and (b) an increase in activity in the assay under the aberrant condition compared to the wild-type protein. This means that the ASTR is a conditionally active protein, which ensures that the CAR containing the ASTR is conditionally active. The conditionally active CARs of the present invention have on or both of (1) their affinity to the target antigen reversibly or irreversibly reduced at the normal physiological condition, and (2) an increased affinity, in comparison with the same CAR without the conditionally active antigen specific targeting region at a disease site where an aberrant condition is present, such as a tumor microenvironment or synovial fluid. As a result of these properties, the conditionally active CARs can preferentially direct the cytotoxic cells to a disease site. Such conditionally active CARs can dramatically reduce side-effects and allow higher doses of therapeutics to be used to increase therapeutic efficacy. The conditionally active CARs are particularly valuable for development of novel therapeutics that are required for short or limited periods of time within a subject. Examples of beneficial applications include systemic treatments at high dosages, as well as localized treatments at high concentrations.

The conditionally active CARs of the present invention are typically generated by an expression vector comprising polynucleotide sequences that encode the different domains of the CAR. The ASTR of the present invention, which functions to recognize and bind with an antigen on a target cell, is conditionally active and it is less active or inactive at a normal physiological condition and more active at an aberrant condition for binding with the target antigen, in comparison with an ASTR of the corresponding wild-type protein or its biding domain (wild-type ASTR).

Once a conditionally active ASTR is identified by the present invention, the chimeric antigen receptor may be assembled by ligating the polynucleotide sequences encoding the individual domains to form a single polynucleotide sequence (the CAR gene, which encodes the conditionally active CAR). The individual domains include a conditionally active ASTR, a TM, and an ISD. In some embodiments, other domains may also be introduced in the CARs, including an ab ESD and a CSD (FIG. 1). If the conditionally active CAR is a bispecific CAR, the CAR gene may be, for example, in the following configuration in the N-terminal to C-terminal direction: N-terminal signal sequence-ASTR 1-linker-ASTR 2-extracellular spacer domain-transmembrane domain-co-stimulatory domain-intracellular signaling domain. In one embodiment, such a CAR gene may comprise two or more co-stimulatory domains.

Alternatively, the polynucleotide sequence encoding the conditionally active CAR may be in the following configuration in the N-terminal to C-terminal direction: N-terminal signal sequence-ASTR 1-linker-ASTR 2-transmembrane domain-co-stimulatory domain-intracellular signaling domain. In an embodiment, such a CAR may comprise two or more co-stimulatory domains. If a CAR comprises more than two ASTRs, the polynucleotide sequence encoding the CAR may be in the following configuration in the N-terminal to C-terminal direction: N-terminal signal sequence-ASTR 1-linker-ASTR 2-linker-(antigen-specific targeting region)$_n$-transmembrane domain-co-stimulatory domain-intracellular signaling domain. Such a CAR may further comprise an extracellular spacer domain. Each ASTR may be separated by a linker. In an embodiment, such a CAR may comprise two or more co-stimulatory domains.

The conditionally active CAR is introduced into the cytotoxic cells by an expression vector. Expression vectors comprising a polynucleotide sequence encoding a conditionally active CAR of the invention are also provided herein.

Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the CAR gene in the host cell. The adenovirus genome is a 36 kb, linear, double stranded DNA, where a foreign DNA sequence (such as CAR genes) may be inserted to substitute large pieces of adenoviral DNA in order to make the expression vector of the present invention (Grunhaus and Horwitz, "Adenoviruses as cloning vectors," *Seminars Virol.*, vol. 3, pages 237-252, 1992).

Another expression vector is based on an adeno associated virus (AAV), which takes advantage of the adenovirus coupled systems. This AAV expression vector has a high frequency of integration into the host genome. It can even infect non-dividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368, each incorporated herein by reference.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., one encoding the CAR) into the viral genome at certain locations to produce a virus that is replication defective. Though the retrovirus vectors are able to infect a broad variety of cell types, integration and stable expression of the CAR gene requires division of the host cells.

Lentivirus vectors are derived from lentiviruses, which are complex retroviruses that, in addition to the common retroviral genes gag, pol, and env, contain other genes with a regulatory or structural function (U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentivirus vectors have been generated by multiply attenuating the HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression of the CAR gene (U.S. Pat. No. 5,994,136, incorporated herein by reference).

Expression vectors comprising the conditionally active CAR gene can be introduced into a host cell by any means known to person skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and screened by virtue of a marker present in the vectors. Various markers that may be used include hprt, neomycin resistance, thymidine kinase, hygromycin resistance, etc. As used herein, the terms "cell," "cell line," and "cell culture" may be used interchangeably. In some embodiments, the host cell is a T cell, NK cell and NKT cell.

In another aspect, the present invention also provides genetically engineered cytotoxic cells which comprise and stably express the conditionally active CAR of the invention. In one embodiment, the genetically engineered cells include T-lymphocytes (T cells), naive T cells ($T_N$), memory T cells (for example, central memory T cells ($TC_M$), effector memory cells ($T_{EM}$)), natural killer cells, and macrophages capable of giving rise to therapeutically relevant progeny. In another embodiment, the genetically engineered cells are autologous cells. Examples of suitable T cells include $CD4^+/CD8^-$, $CD4^-/CD8^+$, $CD4^-/CD8^-$ or $CD4^+/CD8^+$ T cells. The T cells may be a mixed population of $CD4^+/CD8^-$ and $CD4^-/CD8^+$ cells or a population of a single clone. $CD4^+$ T cells of the invention may also produce IL-2, IFN-gamma, TNF-alpha and other T cell effector cytokines when co-cultured in vitro with cells expressing the target antigens (for example $CD20^+$ and/or $CD19^+$ tumor cells). $CD8^+$ T cells of the invention may lyse cells expressing the target antigen. In some embodiments, T cells may be any one or more of $CD45RA^+$ $CD62L^+$ naive cells, CD45RO CD62I7 central memory cells, $CD62L"$ effector memory cells or a combination thereof (Berger et al., "Adoptive transfer of virus-specific and tumor-specific T cell immunity," *Curr. Opin. Immunol.*, vol. 21, pages 224-232, 2009).

Genetically engineered cytotoxic cells may be produced by stably transfecting cells with an expression vector comprising the CAR gene of the invention. Additional methods to genetically engineer cells using the expression vector include chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells demonstrating the presence of a single integrated un-rearranged vector and expressing the conditionally active CAR may be expanded ex vivo.

Physical methods for introducing an expression vector into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

In various embodiments, the present invention provides pharmaceutical compositions comprising a pharmaceutically acceptable excipient and a therapeutically effective amount of the conditionally active CAR of the invention. The conditionally active CAR in the composition may be any one or more of a polynucleotide encoding the CAR, a protein comprising the conditionally active CAR or genetically modified cells expressing the CAR protein. The conditionally active CAR protein may be in the form of a pharmaceutically acceptable salt. Pharmaceutically acceptable salts refers to salts which can be used as salts of a therapeutic protein in the pharmaceutical industry, including for example, salts of sodium, potassium, calcium and the like, and amine salts of procaine, dibenzylamine, ethylenediamine, ethanolamine, methylglucamine, taurine, and the like, as well as acid addition salts such as hydrochlorides, and basic amino acids and the like.

The types of cancers to be treated with the genetically engineered cytotoxic cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. The cancers may be non-solid tumors (such as hematological tumors) or solid tumors. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In some embodiments, the present invention provides a method comprising retrieving cytotoxic cells from a subject, genetically engineering the cytotoxic cells by introducing a CAR gene of the present invention into the cytotoxic cells, and administering the genetically engineered cytotoxic cells to the subject. In some embodiments, the cytotoxic cells are selected from T cells, naive T cells, memory T cells, effector T cells, natural killer cells, and macrophages. In one embodiment, the cytotoxic cells are T cells.

In one embodiment, the T cells are obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from blood collected from a subject using any number of techniques known to the skilled artisan, such as Ficoll™ separation.

In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or another saline solution with or without buffer. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. To enrich $CD4^+$ cells by negative selection, a monoclonal antibody cocktail typically includes antibodies to CD 14, CD20, CD11b, CD 16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$.

For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled person would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

The obtained cytotoxic cells are then genetically engineered as described herein. A polynucleotide encoding the conditionally active CAR, typically located in an expression vector, is introduced into the cytotoxic cells such that the cytotoxic cells will express, preferably stably, the CAR. The polynucleotide encoding the CAR is typically integrated into the cytotoxic cell host genome. In some embodiments, the polynucleotide introduction need not result in integration but rather only transient maintenance of the introduced polynucleotide may be sufficient. In this way, one could have a short term effect, where cytotoxic cells could be introduced into the host and then turned on after a predetermined time, for example, after the cells have been able to migrate to a particular site for treatment.

Depending upon the nature of the cytotoxic cells and the diseases to be treated, the genetically engineered cytotoxic cells may be introduced into the subject, e.g. a mammal, in a wide variety of ways. The genetically engineered cytotoxic cells may be introduced at the site of the tumor. In one embodiment, the genetically engineered cytotoxic cells navigate to the cancer or are modified to navigate to the cancer. The number of genetically engineered cytotoxic cells that are employed will depend upon a number of factors such as the circumstances, the purpose for the introduction, the lifetime of the cells, the protocol to be used. For example, the number of administrations, the ability of the cells to multiply, and the stability of the recombinant construct. The genetically engineered cytotoxic cells may be applied as a dispersion, generally being injected at or near the site of interest. The cells may be in a physiologically-acceptable medium.

It should be appreciated that the treatment method is subject to many variables, such as the cellular response to the conditionally active CAR, the efficiency of expression of the conditionally active CAR by the cytotoxic cells and, as appropriate, the level of secretion, the activity of the expressed conditionally active CAR, the particular need of the subject, which may vary with time and circumstances, the rate of loss of the cellular activity as a result of loss of genetically engineered cytotoxic cells or the expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

Generation of Evolved Molecules from a Parent Molecule

The Conditionally active biologic proteins can be generated through a process of mutagenesis of the wild-type protein and screening for individual mutations for a reduction in activity at the wild-type condition with activity at non wild-type conditions remaining the same or better than the activity at the wild-type condition.

Any chemical synthetic or recombinant mutagenic method may be used to generate the population of mutant polypeptides. The practice of the present invention may employ, unless otherwise indicated, conventional techniques of cell biology, cell culture, molecular biology, transgenic biology, microbiology, recombinant DNA, and immunology. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Cabs eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The disclosure provides for a method for generating a nucleic acid variant encoding a polypeptide having enzyme activity, wherein the variant has an altered biological activity from that which naturally occurs, the method comprising (a) modifying the nucleic acid by (i) substituting one or more nucleotides for a different nucleotide, wherein the nucleotide comprises a natural or non-natural nucleotide; (ii) deleting one or more nucleotides, (iii) adding one or more nucleotides, or (iv) any combination thereof. In one aspect, the non-natural nucleotide comprises inosine. In another aspect, the method further comprises assaying the polypeptides encoded by the modified nucleic acids for altered enzyme activity, thereby identifying the modified nucleic acid(s) encoding a polypeptide having altered enzyme activity. In one aspect, the modifications of step (a) are made by PCR, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis, ligase chain reaction, in vitro mutagenesis, ligase chain reaction, oligonucleotide synthesis, any DNA-generating technique and any combination thereof. In another aspect, the method further comprises at least one repetition of the modification step (a).

The disclosure further provides a method for making a polynucleotide from two or more nucleic acids, the method comprising: (a) identifying regions of identity and regions of diversity between two or more nucleic acids, wherein at least one of the nucleic acids comprises a nucleic acid of the disclosure; (b) providing a set of oligonucleotides which correspond in sequence to at least two of the two or more nucleic acids; and, (c) extending the oligonucleotides with a polymerase, thereby making the polynucleotide.

Any technique of mutagenesis can be employed in various embodiments of the disclosure. Stochastic or random mutagenesis is exemplified by a situation in which a parent molecule is mutated (modified or changed) to yield a set of progeny molecules having mutation(s) that are not predetermined. Thus, in an in vitro stochastic mutagenesis reaction, for example, there is not a particular predetermined product whose production is intended; rather there is an uncertainty—hence randomness—regarding the exact nature of the mutations achieved, and thus also regarding the products generated. Stochastic mutagenesis is manifested in processes such as error-prone PCR and stochastic shuffling, where the mutation(s) achieved are random or not predetermined. The variant forms can be generated by error-prone transcription, such as an error-prone PCR or use of a polymerase which lacks proof-reading activity (see, Liao (1990) Gene 88: 107-111), of the first variant form, or, by replication of the first form in a mutator strain (mutator host cells are discussed in further detail below, and are generally well known). A mutator strain can include any mutants in any organism impaired in the functions of mismatch repair. These include mutant gene products of mutS, mutT, mutH, mutL, ovrD, dcm, vsr, umuC, umuD, sbcB, recJ, etc. The impairment is achieved by genetic mutation, allelic replacement, selective inhibition by an added reagent such as a small compound or an expressed antisense RNA, or other techniques. Impairment can be of the genes noted, or of homologous genes in any organism.

Current mutagenesis methods in widespread use for creating alternative proteins from a starting molecule are oligonucleotide-directed mutagenesis technologies, error-prone polymerase chain reactions (error-prone PCR) and cassette mutagenesis, in which the specific region to be optimized is replaced with a synthetically mutagenized oligonucleotide. In these cases, a number of mutant sites are generated around certain sites in the original sequence.

In oligonucleotide-directed mutagenesis, a short sequence is replaced with a synthetically mutagenized oligonucleotide. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into E. coli and propagated as a pool or library of hybrid plasmids.

Error-prone PCR uses low-fidelity polymerization conditions to introduce a low level of point mutations randomly over a long sequence. In a mixture of fragments of unknown sequence, error-prone PCR can be used to mutagenize the mixture.

In cassette mutagenesis, a sequence block of a single template is typically replaced by a (partially) randomized sequence. Reidhaar-Olson J F and Sauer R T: Combinatorial cassette mutagenesis as a probe of the informational content of protein sequences. *Science* 241(4861):53-57, 1988.

Alternatively, any technique of non-stochastic or non-random mutagenesis can be employed in various embodiments of the disclosure. Non-stochastic mutagenesis is exemplified by a situation in which a parent molecule is mutated (modified or changed) to yield a progeny molecule having one or more predetermined mutations. It is appreciated that the presence of background products in some quantity is a reality in many reactions where molecular processing occurs, and the presence of these background products does not detract from the non-stochastic nature of a mutagenesis process having a predetermined product. Site-saturation mutagenesis and synthetic ligation reassembly, are examples of mutagenesis techniques where the exact chemical structure(s) of the intended product(s) are predetermined.

One method of site-saturation mutagenesis is disclosed in U.S. patent application publication 2009/0130718, which is incorporated herein by reference. This method provides a set of degenerate primers corresponding to codons of a template polynucleotide, and performs polymerase elongation to produce progeny polynucleotides, which contain sequences corresponding to the degenerate primers. The progeny polynucleotides can be expressed and screened for directed evolution. Specifically, this is a method for producing a set of progeny polynucleotides, comprising the steps of (a) providing copies of a template polynucleotide, each comprising a plurality of codons that encode a template polypeptide sequence; and (b) for each codon of the template polynucleotide, performing the steps of (1) providing a set of degenerate primers, where each primer comprises a degenerate codon corresponding to the codon of the template polynucleotide and at least one adjacent sequence that is homologous to a sequence adjacent to the codon of the template polynucleotide; (2) providing conditions allowing the primers to anneal to the copies of the template polynucleotides; and (3) performing a polymerase elongation reaction from the primers along the template; thereby producing progeny polynucleotides, each of which contains a sequence corresponding to the degenerate codon of the annealed primer; thereby producing a set of progeny polynucleotides.

Site-saturation mutagenesis relates to the directed evolution of nucleic acids and screening of clones containing the evolved nucleic acids for resultant activity(ies) of interest, such nucleic acid activity(ies) &/or specified protein, particularly enzyme, activity(ies) of interest.

Mutagenized molecules provided by this technique may have chimeric molecules and molecules with point mutations, including biological molecules that contain a carbohydrate, a lipid, a nucleic acid, &/or a protein component, and specific but non-limiting examples of these include antibiotics, antibodies, enzymes, and steroidal and non-steroidal hormones.

Site saturation mutagenesis relates generally to a method of: 1) preparing a progeny generation of molecule(s) (including a molecule that is comprised of a polynucleotide sequence, a molecule that is comprised of a polypeptide sequence, and a molecule that is comprised in part of a polynucleotide sequence and in part of a polypeptide sequence), that is mutagenized to achieve at least one point mutation, addition, deletion, &/or chimerization, from one or more ancestral or parental generation template(s); 2) screening the progeny generation molecule(s)—preferably using a high throughput method—for at least one property of interest (such as an improvement in an enzyme activity or an increase in stability or a novel chemotherapeutic effect); 3) optionally obtaining &/or cataloguing structural &/or and functional information regarding the parental &/or progeny generation molecules; and 4) optionally repeating any of steps 1) to 3)).

In site saturation mutagenesis, there is generated (e.g. from a parent polynucleotide template)—in what is termed "codon site-saturation mutagenesis"—a progeny generation of polynucleotides, each having at least one set of up to three contiguous point mutations (i.e. different bases comprising a new codon), such that every codon (or every family of degenerate codons encoding the same amino acid) is represented at each codon position. Corresponding to—and encoded by—this progeny generation of polynucleotides, there is also generated a set of progeny polypeptides, each having at least one single amino acid point mutation. In a preferred aspect, there is generated—in what is termed "amino acid site-saturation mutagenesis"-one such mutant polypeptide for each of the 19 naturally encoded polypeptide-forming alpha-amino acid substitutions at each and every amino acid position along the polypeptide. This yields—for each and every amino acid position along the parental polypeptide—a total of 20 distinct progeny polypeptides including the original amino acid, or potentially more than 21 distinct progeny polypeptides if additional amino acids are used either instead of or in addition to the 20 naturally encoded amino acids.

Other mutagenesis techniques can also be employed which involve recombination and more specifically a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

In another aspect, mutagenesis techniques exploit the natural property of cells to recombine molecules and/or to mediate reductive processes that reduce the complexity of sequences and extent of repeated or consecutive sequences possessing regions of homology.

Various mutagenesis techniques can be used alone or in combination to provide a method for generating hybrid polynucleotides encoding biologically active hybrid polypeptides with enhanced activities. In accomplishing these and other objects, there has been provided, in accordance with one aspect of the disclosure, a method for introducing polynucleotides into a suitable host cell and growing the host cell under conditions that produce a hybrid polynucleotide.

Chimeric genes have been made by joining 2 polynucleotide fragments using compatible sticky ends generated by restriction enzyme(s), where each fragment is derived from a separate progenitor (or parental) molecule. Another example is the mutagenesis of a single codon position (i.e. to achieve a codon substitution, addition, or deletion) in a parental polynucleotide to generate a single progeny polynucleotide encoding for a single site-mutagenized polypeptide.

Further, in vivo site specific recombination systems have been utilized to generate hybrids of genes, as well as random methods of in vivo recombination, and recombination between homologous but truncated genes on a plasmid. Mutagenesis has also been reported by overlapping extension and PCR.

Non-random methods have been used to achieve larger numbers of point mutations and/or chimerizations, for example comprehensive or exhaustive approaches have been used to generate all the molecular species within a particular grouping of mutations, for attributing functionality to specific structural groups in a template molecule (e.g. a specific single amino acid position or a sequence comprised of two or more amino acids positions), and for categorizing and comparing specific grouping of mutations.

Any of these or other methods of evolving can be employed in the present disclosure to generate a new population of molecules (library) from one or more parent molecules.

In some embodiments, the polynucleotides encoding the wild-type protein, as well as its mutants can be amplified by several known methods. One of the best known amplification methods is the polymerase chain reaction (referred to as PCR) which is described in detail in U.S. Pat. Nos. 4,683,195, 4,683,202 and 4,800,159, and "PCR Protocols: A guide to methods and applications," edited by Michael A. Innis et al., Academic Press, 1990, each of which is incorporated herein by reference in its entirety. Another method for amplification is the ligase chain reaction ("LCR"), disclosed in EP0320308 A2, incorporated herein by reference in its entirety. In LCR, two complementary probe pairs are prepared, and in the presence of the sequence to be amplified, each pair will bind to opposite complementary strands of the sequence such that they abut. In the presence of a ligase, the two probe pairs will link to form a single unit. By temperature cycling, as in PCR, bound ligated units dissociate from the sequence and then serve as "target sequences" for ligation of excess probe pairs. U.S. Pat. No. 4,883,750 describes a method similar to LCR for binding probe pairs to a sequence.

Qbeta Replicase, described in WO/1987/006270, may also be used as an amplification method. In this method, a replicative sequence of RNA which has a region complementary to that of the sequence to be amplified is added to a sample in the presence of an RNA polymerase. The polymerase will copy the replicative sequence which can then be detected.

An isothermal amplification method, in which restriction endonucleases and ligases are used to achieve the amplification of a sequence that contain nucleotide 5'-[alpha-thio]-triphosphates in one strand of a restriction site may also be useful in the amplification of nucleic acids (Walker et al., Proc. Nat'l Acad. Sci. USA, vol. 89, pages 392-396, 1992).

Strand Displacement Amplification (SDA) is another method of carrying out isothermal amplification of a polynucleotide sequence which involves multiple rounds of strand displacement and synthesis, i.e., nick translation. A similar method, called Repair Chain Reaction (RCR) involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having a 3' and 5' sequences of non-specific DNA and middle sequence of specific RNA is hybridized to DNA which is present in a sample. Upon hybridization, the reaction is treated with RNaseH, and the products of the probe identified as distinctive products which are released after digestion. The original sequence is annealed to another cycling probe and the reaction is repeated.

Other amplification methods are described in GB Patent Application No. 2 202 328, and in WO1989/009284, each of which is incorporated herein by reference in its entirety, may be used in accordance with the present invention. In the former application, "modified" primers are used in a PCR like, template (sequence to be amplified) and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., Proc. Natl. Acad. Sci. USA, vol. 86, pages 1173-1177, 1989). In NASBA, the polynucleotide can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double-stranded by addition of second target specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate target specific sequences.

Davey et al., EP0329822 A2 (incorporated herein by reference) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Kienow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Methods based on ligation of two (or more) oligonucleotides in the presence of nucleic acid having the sequence of the resulting "di-oligonucleotide," thereby amplifying the di-oligonucleotide, also may be used in the amplification step (Wu et al., *Genomics*, vol. 4, page 560, 1989).

Once formed, the constructs may, or may not be size fractionated on an agarose gel according to published protocols, inserted into a cloning vector, and transfected into an appropriate host cell.

Expression of Evolved Molecules

Once a library of mutant molecules is generated, DNA can be expressed using routine molecular biology techniques. Thus, protein expression can be directed using various known methods.

For example, briefly, a wild type gene can be evolved using any variety of random or non-random methods such as those indicated herein. Mutant DNA molecules are then digested and ligated into vector DNA, such as plasmid DNA using standard molecular biology techniques. Vector DNA containing individual mutants is transformed into bacteria or other cells using standard protocols. This can be done in an individual well of a multi-well tray, such as a 96-well tray for high throughput expression and screening. The process is repeated for each mutant molecule.

Polynucleotides selected and isolated as described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (e.g. Ecker and Davis, 1986, Inhibition of gene expression in plant cells by expression of antisense RNA, *Proc Natl Acad Sci USA*, 83:5372-5376).

As representative examples of expression vectors which may be used, there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, aspergillus* and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present disclosure.

The DNA sequence in the expression vector is operatively linked to an appropriate expression control sequence(s) (promoter) to direct RNA synthesis. Particular named bacterial promoters include lad, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The expression vectors will typically include an expression control sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the introduced coding sequences to produce the mutant proteins.

As stated previously, the DNA sequences encoding the mutant proteins will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

Therefore, in another aspect of the disclosure, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

In one aspect, the host organism or cell comprises a gram negative bacterium, a gram positive bacterium or a eukaryotic organism. In another aspect of the disclosure, the gram negative bacterium comprises *Escherichia coli*, or *Pseudomonas fluorescens*. In another aspect of the disclosure, the gram positive bacterium comprise *Streptomyces diversa, Lactobacillus gasseri, Lactococcus lactis, Lactococcus cremoris*, or *Bacillus subtilis*. In another aspect of the disclosure, the eukaryotic organism comprises *Saccharomyces cerevisiae, Schizosaccharomyces pombe, Pichia pastoris, Kluyveromyces lactis, Hansenula plymorpha*, or *Aspergillus niger*. As representative examples of appropriate hosts, there may be mentioned: bacterial cells, such as *E. coli, Streptomyces, Salmonella typhimurium*; fungal cells, such as yeast; insect cells such as *Drosophila* S2 and Spodoptera Sf9; animal cells such as CHO, COS or Bowes melanoma; adenoviruses; and plant cells. The selection of an appropriate host is deemed to be within the scope of those skilled in the art from the teachings herein.

In addition to eukaryotic microorganisms such as yeast, mammalian tissue cell cultures may also be used to express the mutant polypeptides of the present invention (see, Winnacker, "From Genes to Clones," VCH Publishers, N.Y., N.Y. (1987), which is incorporated herein by reference). Eukaryotic cells are preferred, because a number of suitable host cell lines capable of secreting intact immunoglobulins have been developed in the art, and include the CHO cell lines, various COS cell lines, HeLa cells, myeloma cell lines, B-cells or hybridomas. Expression vectors for these cells can include expression control sequences, such as an origin of replication, a promoter, an enhancer (Queen et al., Immunol. Rev., vol. 89, page 49, 1986), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the expression vector. Enhancers are cis-acting sequences of between 10 to 300 bp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The expression vectors containing the DNA segments of interest can be transferred into host cells by well-known methods, depending on the type of cell production hosts. For example, calcium chloride transfection is commonly utilized for prokaryotic host cells, whereas calcium phosphate treatment, lipofection, or electroporation may be used for eukaryotic host cells. Other methods used to transform mammalian cell production hosts include the use of polybrene, protoplast fusion, liposomes, electroporation, and microinjection (see, generally, Sambrook et al., supra).

In one embodiment, the eukaryotic cell production host is a mammalian system selected from CHO, HEK293, IM9, DS-1, THP-1, Hep G2, COS, NIH 3T3, C33a, A549, A375, SK-MEL-28, DU 145, PC-3, HCT 116, Mia PACA-2, ACHN, Jurkat, MM1, Ovcar 3, HT 1080, Panc-1, U266, 769P, BT-474, Caco-2, HCC 1954, MDA-MB-468, LnCAP, NRK-49F, and SP2/0 cell lines; and mouse splenocytes and rabbit PBMC. In one aspect, the mammalian system is selected from a CHO or HEK293 cell line. In one specific aspect, the mammalian system is a CHO-S cell line. In another specific aspect, the mammalian system is a HEK293 cell line. In another embodiment, the eukaryotic cell production host is a yeast cell system. In one aspect, the eukaryotic system is selected from S. cerevisiae yeast cells or picchia yeast cells.

In another embodiment, mammalian system may be created commercially by a contract research or custom manufacturing organization. For example, for recombinant antibodies or other proteins, Lonza (Lonza Group Ltd, Basel, Switzerland) can create vectors to express these products using the GS Gene Expression System™ technology with either CHOK1SV or NS0 cell production hosts.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The cells are then propagated and "reductive reassortment" is effected. The rate of the reductive reassortment process may be stimulated by the introduction of DNA damage if desired, in vivo reassortment is focused on "inter-molecular" processes collectively referred to as "recombination" which in bacteria, is generally viewed as a "RecA-dependent" phenomenon. The disclosure can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process. The end result is a reassortment of the molecules into all possible combinations.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

Protein expression can be induced by a variety of known methods, and many genetic systems have been published for induction of protein expression. For example, with appropriate systems, the addition of an inducing agent will induce protein expression. Cells are then pelleted by centrifugation and the supernatant removed. Periplasmic protein can be enriched by incubating the cells with DNAse, RNAse, and lysozyme. After centrifugation, the supernatant, containing the new protein, is transferred to a new multi-well tray and stored prior to assay.

The mutant proteins of the present invention are expressed in a eukaryotic cell production host (from the mutant DNAs), such as a mammalian cell production host or a yeast cell production host, that will also be used for downstream production of the conditionally active biologic protein selected from screening the mutant proteins. The conditionally active biologic proteins identified in this manner can be used for expression in the same host as was used in the prior expression step of the process.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The clones which are identified as having the desired activity may then be sequenced to identify the polynucleotide sequence encoding an enzyme having the enhanced activity.

The polypeptides, i.e. conditionally active biologic proteins, that are identified from such libraries can be used for therapeutic, diagnostic, research and related purposes, and/or can be subjected to one or more additional cycles of shuffling and/or selection. The disclosure provides for a fragment of the conditionally active biologic protein which is at least 10 amino acids in length, and wherein the fragment has activity.

The disclosure provides for a codon-optimized polypeptide or a fragment thereof, having enzyme activity, wherein the codon usage is optimized for a particular organism or cell. Narum et al., "Codon optimization of gene fragments encoding *Plasmodium falciparum* merzoite proteins enhances DNA vaccine protein expression and immunogenicity in mice". *Infect. Immun.* 2001 December, 69(12): 7250-3 describes codon-optimization in the mouse system. Outchkourov et al., "Optimization of the expression of Equistatin in *Pichia pastoris*, protein expression and purification", *Protein Expr. Purif.* 2002 February; 24(1): 18-24 describes codon-optimization in the yeast system. Feng et al., "High level expression and mutagenesis of recombinant human phosphatidylcholine transfer protein using a synthetic gene: evidence for a C-terminal membrane binding domain" *Biochemistry* 2000 Dec. 19, 39(50): 15399-409 describes codon-optimization in *E. coli*. Humphreys et al., "High-level periplasmic expression in *Escherichia coli* using a eukaryotic signal peptide: importance of codon usage at the 5' end of the coding sequence", *Protein Expr. Purif.*, vol. 20, pages, 252-264, 2000, describes how codon usage affects secretion in *E. coli*.

The evolution of a conditionally active biologic protein can be aided by the availability of a convenient high throughput screening or selection process.

As discussed above, expression optimization for the conditionally active biologic protein can be achieved by optimization of vectors used (vector components, such as promoters, splice sites, 5' and 3' termini and flanking sequences), gene modification of host cells to reduce gene deletions and rearrangements, evolution of host cell gene activities by in vivo or in vitro methods of evolving relevant genes, optimization of host glycosylating enzymes by evolution of relevant genes, and/or by chromosome-wide host cell mutagenesis and selection strategies to select for cells with enhanced expression capabilities. Host cells are further described herein.

Cell surface display expression and screening technology (for example, as defined above) can be employed to screen mutant proteins for conditionally active biologic proteins.

In one aspect, codon mutagenesis is performed in the constant region of an antibody for optimization of eukaryotic cell expression. A codon optimized Fc variant with improved expression properties which retains the capacity to mediate effector functions improves the production of therapeutic antibodies. In this aspect, for example, a constant region of an antibody molecule can be evolved for screening in different expression hosts. For example, mammalian cell lines can be expression screened utilizing CHO, HEK293 and COS-7.

Screening of Mutants to Identify Reversible or Non-Reversible Mutants

Identifying desirable molecules is most directly accomplished by measuring protein activity at the permissive condition and the wild type condition. The mutants with the largest ratio of activity (permissive/wild type) can then be selected and permutations of the point mutations are generated by combining the individual mutations using standard methods. The combined permutation protein library is then screened for those proteins displaying the largest differential activity between the permissive and wild type condition.

Activity of supernatants can be screened using a variety of methods, for example using high throughput activity assays, such as fluorescence assays, to identify protein mutants that are sensitive at whatever characteristic one desires (temperature, pH, etc). For example, to screen for temporally sensitive mutants, the enzymatic or antibody activity of each individual mutant is determined at lower temperatures (such as 25 degrees Celsius), and at temperatures which the original protein functions (such as 37 degrees Celsius), using commercially available substrates. Reactions can initially be performed in a multi well assay format, such as a 96-well assay, and confirmed using a different format, such as a 14 ml tube format.

The disclosure further provides a screening assay for identifying a enzyme, the assay comprising: (a) providing a plurality of nucleic acids or polypeptides; (b) obtaining polypeptide candidates to be tested for enzyme activity from the plurality; (c) testing the candidates for enzyme activity; and (d) identifying those polypeptide candidates which exhibit elevated enzyme activity under aberrant or non-physiological conditions, and decreased enzyme activity compared to the wild-type enzyme protein under normal physiological conditions of, e.g., temperature, pH, oxidative stress, osmolality, electrolyte concentration or osmotic pressure.

In one aspect, the method further comprises modifying at least one of the nucleic acids or polypeptides prior to testing the candidates for conditional biologic activity, in another aspect, the testing of step (c) further comprises testing for improved expression of the polypeptide in a host cell or host organism, in a further aspect, the testing of step (c) further comprises testing for enzyme activity within a pH range from about pH 3 to about pH 12. In a further aspect, the testing of step (c) further comprises testing for enzyme activity within a pH range from about pH 5 to about pH 10. In a further aspect, the testing of step (c) further comprises testing for enzyme activity within a pH range from about pH 6 to about pH 8. In a further aspect, the testing of step (c) further comprises testing for enzyme activity at pH 6.7 and pH 7.5. In another aspect, the testing of step (c) further comprises testing for enzyme activity within a temperature range from about 4 degrees C. to about 55 degrees C. In another aspect, the testing of step (c) further comprises testing for enzyme activity within a temperature range from about 15 degrees C. to about 47 degrees C. In another aspect, the testing of step (c) further comprises testing for enzyme activity within a temperature range from about 20 degrees C. to about 40 degrees C. In another aspect, the testing of step (c) further comprises testing for enzyme activity at the temperatures of 25 degrees C. and 37 degrees C. In another aspect, the testing of step (c) further comprises testing for enzyme activity under normal osmotic pressure, and aberrant (positive or negative) osmotic pressure, In another aspect, the testing of step (c) further comprises testing for enzyme activity under normal electrolyte concentration, and aberrant (positive or negative) electrolyte concentration. The electrolyte concentration to be tested is selected from one of calcium, sodium, potassium, magnesium, chloride, bicarbonate and phosphate concentration, in another aspect, the testing of step (c) further comprises testing for enzyme activity which results in a stabilized reaction product.

In another aspect, the disclosure provides for a purified antibody that specifically binds to the polypeptide of the disclosure or a fragment thereof, having enzyme activity, In one aspect, the disclosure provides for a fragment of the antibody that specifically binds to a polypeptide having enzyme activity.

The normal physiological condition and the aberrant condition for the screening assays may be any condition selected from temperature, pH, osmotic pressure, osmolality, oxidation, and electrolyte concentration, as well as combinations of two or more such conditions. For example, the normal physiological condition for temperature may be a normal human body temperature of 37.0° C., while the aberrant condition for temperature may be a temperature different from the temperature of 37.0° C. The normal physiological condition and the aberrant condition may also be a normal physiological pH and an aberrant pH The assays under both the normal physiologic condition and the aberrant condition may be performed using a media, such as a liquid media that may contain, for example, a buffer. A common screening buffer is the Krebs buffer. However, other buffers known to skilled persons to be suitable for assays may be used. Many of these buffers attempt to mimic the composition of a bodily fluid, such as serum or lymphatic fluid. The buffer used in the method of the invention may contain at least one component selected from on or more of an inorganic compound, an ion and an organic molecule commonly found in a bodily fluid of mammals or humans. Examples of such components include at least nutrients and metabolites, as well as any other components that may be found in bodily fluids. In these embodiments, the concentration of the component in the buffer may be the same or substantially the same as the concentration of the same component that is typically found in a naturally-occurring bodily fluid of a mammal, preferably a human. This may be referred to as a normal physiological concentration of the component in the bodily fluid.

In one embodiment, the assay under the normal physiologic condition is performed in a composition at a normal physiological pH such as, for example a pH of 7.4. This assay is carried out in the presence of at least one component selected from the inorganic compounds, ions, and organic molecules that are commonly found in a bodily fluid of mammals or humans. The assay under the aberrant condition is performed at an aberrant pH that is different from the normal physiological pH, such as pH 6, in the presence of the same components such as a buffer. Thus, in this embodiment the fluid in which both assays is conducted includes the same component(s) at the same concentrations which should preferably within or proximate to a range of normal physiological concentrations.

For example, the assay under the normal physiological condition may be performed in a buffered fluid at a normal physiological temperature, such as 37° C., in the presence of at least one component selected from the inorganic compounds, ions, and organic molecules set forth above. The assay under the aberrant condition is performed in a buffered fluid at a different, aberrant temperature, such as 36° C. in the presence of the same component(s). Again, the fluid in which both assays are conducted includes the same component(s) at the same concentrations which should preferably within a range of normal physiological concentrations. The presence of the one or more component(s) in the fluid used for the assay at normal physiological concentration(s) may improve the selection process for selecting the conditionally active biologic protein.

The inorganic compounds or ions may be selected from one or more of boric acid, calcium chloride, calcium nitrate, di-ammonium phosphate, magnesium sulfate, mono-ammonium phosphate, mono-potassium phosphate, potassium chloride, potassium sulfate, copper sulfate, iron sulfate, manganese sulfate, zinc sulfate, magnesium sulfate, calcium nitrate, chelates of calcium, copper, iron, manganese and zinc, ammonium molybdate, ammonium sulphate, calcium carbonate, magnesium phosphate, potassium bicarbonate, sodium bicarbonate, potassium nitrate, hydrochloric acid, carbon dioxide, sulfuric acid, phosphoric acid, carbonic acid, uric acid, hydrogen chloride, urea, phosphorus ions, sulfuric ions, chloride ions, magnesium ions, sodium ions, potassium ions, ammonium ions, iron ions, zinc ions and copper ions.

Examples of normal physiological concentrations of some of the inorganic compounds include: uric acid in a concentration range of 2-7.0 mg/dL, calcium ion in a concentration range of 8.2-11.6 mg/dL, chloride ion in a concentration range of 355-381 mg/dL, iron ion in a concentration range of 0.028-0.210 mg/dL, potassium ion in a concentration range of 12.1-25.4 mg/dL, sodium ion in a concentration range of 300-330 mg/dL and carbonic acid in a concentration range of 15-30 mM.

The organic compounds may be selected from, for example, amino acids such as Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Pyrrolysine, Proline, Selenocysteine, Serine, Tyrosine and mixtures thereof.

Examples of a normal physiological concentration of some of the amino acids include: Alanine at 3.97±0.70 mg/dL, Arginine at 2.34±0.62 mg/dL, Glutamic acid at 3.41±1.39 mg/dL, Glutamine at 5.78±1.55 mg/dL, Glycine at 1.77±0.26 mg/dL, Histidine at 1.42±0.18 mg/dL, Isoleucine at 1.60±0.31 mg/dL, Leucine at 1.91±0.34 mg/dL, Lysine at 2.95±0.42 mg/dL, Methionine at 0.85±0.46 mg/dL, Phenylalanine at 1.38±0.32 mg/dL, Threonine at 2.02±6.45 mg/dL, Tryptophane at 1.08±0.21 mg/dL, Tyrosine at 1.48±0.37 mg/dL and Valine at 2.83±0.34 mg/dL.

The organic compounds may be non-protein, nitrogen-containing compounds such as creatine, creatinine, guanidino acetic acid, uric acid, allantoin, adenosine, urea, ammonia and choline. Examples of normal physiological concentrations of some of these compounds include: creatine at 1.07±0.76 mg/dL, creatinine at from 0.9 to 1.65 mg/dL, guanidino acetic acid at 0.26±0.24 mg/dL, uric acid at 4.0±2.9 mg/dL, allantoin at from 0.3 to 0.6 mg/dL, adenosine at 1.09±0.385 mg/dL, urea 27.1±4.5 mg/dL and choline at from 0.3 to 1.5 mg/dL.

The organic compounds may be organic acids such as citric acid, α-ketoglutaric acid, succinic acid, malic acid, fumaric acid, acetoacetic acid, β-hydroxybutyric acid, lactic acid, pyruvic acid, α-ketonic acid, acetic acid, and volatile fatty acids. Examples of normal physiological concentrations of some of these organic acids include: citric acid at 2.5±1.9 mg/dL, α-ketoglutaric acid at 0.8 mg/dL, succinic acid at 0.5 mg/dL, malic acid at 0.46±0.24 mg/dL, acetoacetic acid at from 0.8 to 2.8 mg/dL, β-hydroxybutyric acid at 0.5±0.3 mg/dL, lactic acid at from 8 to 17 mg/dL, pyruvic acid at 1.0±0.77 mg/dL, a-ketonic acids at from 0.6 to 2.1 mg/dL, volatile fatty acids at 1.8 mg/dL.

The organic compounds may be sugars (carbohydrates) such as glucose, pentose, hexose, xylose, ribose, mannose and galactose, as well as disaccharides including lactose, GlcNAcβ1-3Gal, Galα1-4Gal, Manα1-2Man, GalNAcβ1-3Gal and O-, N-, C-, or S-glycosides. Examples of normal physiological concentrations of some of these sugars include: glucose at 83±4 mg/dL, polysaccharides at 102±73 mg/dL (as hexose), glucosamine at 77±63 mg/dL, hexuronates at from 0.4 to 1.4 mg/dL (as glucuronic acid) and pentose at 2.55±0.37 mg/dL.

The organic compounds may be fats or their derivatives such as cholesterol lecithin, cephalin, sphingomyelin and bile acid. Examples of normal physiological concentrations of some of these compounds include: free cholesterol at from 40 to 70 mg/dL, lecithin at from 100 to 200 mg/dL, cephalin at from 0 to 30 mg/dL, sphingomyelin at from 10 to 30 mg/dL and bile acids at from 02. To 0.3 mg/dL. (as cholic acid).

The organic compounds may be proteins such as fibrinogen, antihaemophilic globulin, immune γ-globulin, immune euglobulins, isoagglutinins, β-pseudoglobulin, bovine serum albumin, glycoproteins, lipoproteins and albumin. For example, the normal physiological concentration of albumin is 3.35 mg/dL.

The organic compounds may be vitamins such as Vitamin A, Carotene, Vitamin E, Ascorbic acid, Thiamine, Inositol, Folic acid, Biotin, Pantothenic acid, Riboflavin. Examples of normal physiological concentrations of some of these vitamins include: Vitamin A at from 0.019 to 0.036 mg/dL, Vitamin E at from 0.90 to 1.59 mg/dL, Inositol at from 0.42 to 0.76 mg/dL, Folic acid at from 0.00162 to 0.00195 mg/dL, and biotin from 0.00095 to 0.00166 mg/dL Antibodies and Antibody-Based Screening Methods The disclosure provides isolated or recombinant antibodies that specifically bind to an enzyme of the disclosure. These antibodies can be used to isolate, identify or quantify the enzymes of the disclosure or related polypeptides. These antibodies can be used to isolate other polypeptides within the scope the disclosure or other related enzymes. The antibodies can be designed to bind to an active site of an enzyme. Thus, the disclosure provides methods of inhibiting enzymes using the antibodies of the disclosure.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the disclosure. Alternatively, the methods of the disclosure can be used to modify the structure of an antibody produced by a cell to be modified, e.g., an antibody's affinity can be increased or decreased. Furthermore, the ability to make or modify antibodies can be a phenotype engineered into a cell by the methods of the disclosure.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N Y (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) "Continuous cultures of fused cells secreting antibody of predefined specificity", Nature 256: 495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) "Designing and optimizing library selection strategies for generating high-affinity antibodies", Trends Biotechnol. 15:62-70; and Katz (1997) "Structural and mechanistic determinants of affinity and specificity of ligands discovered or engineered by phage display", Annu. Rev. Biophys. Biomol. Struct. 26:27-45.

Polypeptides or peptides can be used to generate antibodies which bind specifically to the polypeptides, e.g., the enzymes, of the disclosure. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the disclosure.

In immunoaffinity procedures, the antibody is attached to a solid support, such as a bead or other column matrix. The protein preparation is placed in contact with the antibody under conditions in which the antibody specifically binds to one of the polypeptides of the disclosure. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the disclosure can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the disclosure. Alternatively, transgenic mice may be used to express humanized antibodies to these polypeptides or fragments thereof. Antibodies generated against the polypeptides of the disclosure may be used in screening for similar polypeptides (e.g., enzymes) from other organisms and samples. In such techniques, polypeptides from the organism are contacted with the antibody and those polypeptides which specifically bind the antibody are detected. Any of the procedures described above may be used to detect antibody binding.

Screening Methodologies and "On-Line" Monitoring Devices

In practicing the methods of the disclosure, a variety of apparatus and methodologies can be used to in conjunction with the polypeptides and nucleic acids of the disclosure, e.g., to screen polypeptides for enzyme activity, to screen compounds as potential modulators, e.g., activators or inhibitors, of an enzyme activity, for antibodies that bind to a polypeptide of the disclosure, for nucleic acids that hybridize to a nucleic acid of the disclosure, to screen for cells expressing a polypeptide of the disclosure and the like.

Arrays, or "Biochips"

Nucleic acids or polypeptides of the disclosure can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the disclosure. For example, in one aspect of the disclosure, a monitored parameter is transcript expression of an enzyme gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the disclosure. Polypeptide arrays" can also be used to simultaneously quantify a plurality of proteins. The present disclosure can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the disclosure, any known array and/or method of making and using arrays can be incorporated in whole or in part, or variations thereof, as described, for example, in U.S. Pat. Nos. 6,277,628; 6,277, 489; 6,261,776; 6,258,606; 6,054,270; 6,048,695; 6,045, 996; 6,022,963; 6,013,440; 5,965,452; 5,959,098; 5,856, 174; 5,830,645; 5,770,456; 5,632,957; 5,556,752; 5,143, 854; 5,807,522; 5,800,992; 5,744,305; 5,700,637; 5,556, 752; 5,434,049; see also, e.g., WO 99/51773; WO 99/09217; WO 97/46313; WO 96/17958; see also, e.g., Johnston (1998) "Gene chips: Array of hope for understanding gene regulation", Curr. Biol. 8:R171-R174; Schummer (1997) "Inexpensive Handheld Device for the Construction of High-Density Nucleic Acid Arrays", Biotechniques 23:1087-1092; Kern (1997) "Direct hybridization of large-insert genomic clones on high-density gridded cDNA filter arrays", Biotechniques 23:120-124; Solinas-Toldo (1997) "Matrix-Based Comparative Genomic Hybridization: Biochips to Screen for Genomic Imbalances", Genes, Chromosomes & Cancer 20:399-407; Bowtell (1999) "Options Available—From Start to Finish~for Obtaining Expression Data by Microarray", Nature Genetics Supp. 21:25-32. See also published U.S. patent applications Nos. 20010018642; 20010019827; 20010016322; 20010014449; 20010014448; 20010012537; 20010008765.

Capillary Arrays

Capillary arrays, such as the GIGAMATRIX™ Diversa Corporation, San Diego, Calif., can be used in the methods of the disclosure. Nucleic acids or polypeptides of the disclosure can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the disclosure. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample. A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube. The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together. Pharmaceutical Compositions.

In certain embodiments, the present invention is aimed at producing conditionally active biologic proteins with a large activity ratio of the activity at the aberrant condition to the activity at the normal physiological condition (e.g., a larger selectivity between the aberrant and normal physiologic conditions). The ratio, or selectivity, of the activity at the aberrant condition to the activity at the normal physiological condition may be at least about 2:1, or at least about 3:1, or at least about 4:1 or at least about 5:1, or at least about 6:1, or at least about 7:1, or at least about 8:1, or at least about 9:1, or at least about 10:1 or at least about 11:1, or at least about 12:1, or at least about 13:1, or at least about 14:1, or at least about 15:1, or at least about 16:1, or at least about 17:1, or at least about 18:1, or at least about 19:1, or at least about 20:1, or at least about 30:1, or at least about 40:1, or at least about 50:1, or at least about 60:1 or at least about 70:1, or at least about 80:1, or at least about 90:1, or at least about 100:1.

In one embodiment, conditionally active biologic protein is an antibody, which may have a ratio of the activity at the aberrant condition to the activity at the normal physiological condition of at least about 5:1, or at least about 6:1, or at least about 7:1, or at least about 8:1, or at least about 9:1, or at least about 10:1. In one embodiment, the conditionally active biologic protein is used to target a tumor site and the conditionally active biologic protein has a particular activity at the tumor site and is significantly less active or inactive for the same activity at a non-tumor site (normal physiological condition).

In one embodiment, the conditionally active biologic protein is an antibody that is intended to be conjugated with another agent such as those disclosed elsewhere herein. The conditionally active antibody may have a higher ratio of the activity at the aberrant condition to the activity at the normal physiological condition than a wild-type antibody from which it is derived. For example, the conditionally active antibody that is to be conjugated with another agent may have a ratio of the activity at the aberrant condition to the activity at the normal physiological condition of at least about 10:1, or at least about 11:1, or at least about 12:1, or at least about 13:1, or at least about 14:1, or at least about 15:1, or at least about 16:1, or at least about 17:1, or at least about 18:1, or at least about 19:1, or at least about 20:1. This may be particularly important when the conjugated agent is, for example, toxic or radioactive, since such a conjugated agent is desirably concentrated at the disease or treatment site.

Producing/Manufacturing the Conditionally Active Biologic Proteins

Once identified in the screening step, conditionally active biologic proteins of the disclosure can be synthesized, or be recombinantly generated. The conditionally active biologic proteins can be recombinantly expressed in vitro or in vivo. The conditionally active biologic proteins can be made and isolated using any method known in the art. The conditionally active biologic proteins can also be synthesized, in whole or in part, using chemical protein synthesis methods well known in the art. See e.g., Caruthers (1980) "New chemical methods for synthesizing polynucleotides", *Nucleic Acids Res.* Symp. Ser. 215-223; Horn (1980), "Synthesis of oligonucleotides on cellulose. Part II: design and synthetic strategy to the synthesis of 22 oligodeoxynucleotides coding for Gastric Inhibitory Polypeptide (GIP)[1]", *Nucleic Acids Res. Symp. Ser.* 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) "A strategy for a convergent synthesis of N-linked glycopeptides on a solid support", *Science* 269: 202; Merrifield (1997) "Concept and early development of solid-phase peptide synthesis", *Methods Enzymol.* 289:3-13) and automated synthesis may be achieved, e.g., using the ABI 43 IA Peptide Synthesizer (Perkin Elmer) in accordance with the instructions provided by the manufacturer.

Solid-phase chemical peptide synthesis methods can also be used to synthesize the polypeptide or fragments. Such methods have been known in the art since the early 1960's (Merrifield, R. B., "Solid-phase synthesis. I. The synthesis of a tetrapeptide", *J. Am. Chem. Soc,* 85:2149-2154, 1963) (See also Stewart, J. M. and Young, J. D., Solid Phase Peptide Synthesis, 2nd Ed., Pierce Chemical Co., Rockford, 111., pp. 11-12)) and have recently been employed in commercially available laboratory peptide design and synthesis kits (Cambridge Research Biochemicals). Such commercially available laboratory kits have generally utilized the teachings of H. M. Geysen et al., "Use of peptide synthesis to probe viral antigens for epitopes to a resolution of a single amino acid," *Proc. Natl. Acad. Sci., USA,* 81:3998 (1984) and provide for synthesizing peptides upon the tips of a multitude of "rods" or "pins" all of which are connected to a single plate.

When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431 A™ automated peptide synthesizer. Such equipment provides ready access to the peptides of the disclosure, either by direct synthesis or by synthesis of a series of fragments that can be coupled using other known techniques.

The conditionally active biologic proteins of the disclosure can also be glycosylated. The glycosylation can be added post-translationally either chemically or by cellular biosynthetic mechanisms, wherein the latter incorporates the use of known glycosylation motifs, which can be native to the sequence or can be added as a peptide or added in the nucleic acid coding sequence. The glycosylation can be O-linked or N-linked.

The conditionally active biologic proteins of the disclosure, as defined above, include all "mimetic" and "peptidomimetic" forms. The terms "mimetic" and "peptidomimetic" refer to a synthetic chemical compound which has substantially the same structural and/or functional characteristics of the polypeptides of the disclosure. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the disclosure which are conservative variants, routine experimentation will determine whether a mimetic is within the scope of the disclosure, i.e., that its structure and/or function is not substantially altered.

Polypeptide mimetic compositions of the disclosure can contain any combination of non-natural structural components. In an alternative aspect, mimetic compositions of the disclosure include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the disclosure can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be used as an alternative to the traditional amide bond ("peptide bond") linkages include, e.g., ketomethylene (e.g., —C(.dbd.O)—CH$_2$— for —C(.dbd.O)—NH—), aminomethylene (CH.sub.2-NH), ethylene, olefin (CH.dbd.CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, N. Y.).

A polypeptide of the disclosure can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines for their use are described below. Mimetics of aromatic amino acids can be generated by replacing by, e.g., D- or L-naphylalanine; D- or L-phenylglycine; D- or L-2 thieneylalanine; D- or L-1,-2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenylphenylalanine; D- or L-2-indole(alkyl) alanines; and, D- or L-alkylanines, where alkyl can be substituted or unsubstituted methyl, ethyl, propyl, hexyl, butyl, pentyl, isopropyl, iso-butyl, sec-buttyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylated amino acids, while maintaining a negative charge; (phosphono)alanine; sulfated threonine. Carboxyl side groups (e.g., aspartyl or glutamyl) can also be selectively modified by reaction with carbodiimides (R'~N—C—N—R') such as, e.g., 1-cyclohexyl-3(2-mo¢pholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivatives (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; and chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the disclosure can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, which also can be referred to as the R- or S-form.

The mimetic polypeptides of the present invention may be synthesized using any protein chemical synthesis techniques. In a typical in vitro protein synthesis process, a peptide is extended in length by one amino acid by forming a peptide bond between the peptide and an amino acid. The formation of the peptide bond is a ligation reaction, which can use a natural amino acid or a non-natural amino acid. Thus, non-natural amino acids can be introduced into the polypeptides of the present invention to make mimetics.

Protein chemical synthesis techniques are described in Nilsson et al., "Chemical Synthesis of Proteins," *Annu. Rev. Biophys. Biomol. Struct.*, vol. 34, page 91-118, 2005 (incorporated herein by reference). Solid-phase synthesis and semisynthetic methods have also allowed for the synthesis of a number of small proteins containing novel amino acids. For example, see the following publications: Crick, F. J. C., Barrett, L. Brenner, S. Watts-Tobin, R. "General nature of the genetic code for proteins," *Nature,* 1227-1232 (1961); Hofmann, K., Bohn, H. "Studies on polypeptides. XXXVI. The effect of pyrazole-imidazole replacements on the S-protein activating potency of an S-peptide fragment," *J. Am Chem,* 5914-5919 (1966); Kaiser, E. T. "Synthetic approaches to biologically active peptides and proteins including enyzmes," *Acc Chem Res,* 47-54 (1989); Nakatsuka, T., Sasaki, T., Kaiser, E. T. "Peptide segment coupling catalyzed by the semisynthetic enzyme thiosubtilisin," *J Am Chem Soc,* 3808-3810 (1987); Schnolzer, M., Kent, S B H. "Constructing proteins by dovetailing unprotected synthetic peptides: backbone-engineered HIV protease," *Science,* 221-225 (1992); Chaiken, I. M. "Semisynthetic peptides and proteins," *CRC Crit Rev Biochem,* 255-301 (1981); Offord, R. E. "Protein engineering by chemical means?" *Protein Eng.,* 151-157 (1987); and, Jackson, D. Y., Burnier, J., Quan, C., Stanley, M., Tom, J., Wells, J. A. "A Designed Peptide Ligase for Total Synthesis of Ribonuclease A with Unnatural Catalytic Residues," *Science,* 243 (1994).

The mimetic polypeptides of the present invention may also be produced by recombinant techniques, which produce a polypeptide by inserting a coding sequence of the polypeptide into an expression vector and utilizing the protein translation machinery of a eukaryotic cell production host. The protein translation machinery reads the codons of the coding sequence and uses tRNA to bring in the encoded amino acid to produce the polypeptide. There are several techniques can be used to alter the protein translation machinery to allow it to incorporate a non-natural amino acid into a recombinant polypeptide. A proven approach depends on the recognition of the non-natural amino acid by aminoacyl-tRNA synthetases, which, in general, require high selectivity to insure the fidelity of protein translation. These synthetases may be engineered to relax the substrate specificity such that non-natural amino acid may be linked to a tRNA, which then bring non-natural amino acid to the protein translation machinery to be incorporated into a polypeptide. For example, it was found that replacement of $Ala^{294}$ by Gly in *Escherichia coli* phenylalanyl-tRNA synthetase (PheRS) increases the size of the substrate binding pocket, and results in the acylation of $tRNA^{Phe}$ by p-Cl-phenylalanine (p-Cl-Phe). See, M. Ibba, P. Kast and H. Hennecke, *Biochemistry,* 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.,* 364:272 (1995); and, N. Sharma, R. Furter, P. Kast and D. A. Tirrell, *FEBS Lett.,* 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yana, K. Takaku, Y. Monden, M. Kitabatake, D. Soll and S. Nishimura, *J. Biol. Chem.,* 275:40324 (2000).

The first method functions by reassigning sense codon, which engineers at least one aminoacyl-tRNA synthetase. The enzyme normally adds a natural amino acid to a tRNA to be transported to the protein translation machinery for protein synthesis. However, an aminoacyl-tRNA synthetase for a particular tRNA may be altered such that it can have certain level of promiscuity to change a non-natural amino acid non-specifically to the tRNA to activate the tRNA. The activated tRNA can carry the non-natural amino acid to the protein translation machinery (ribosomes) and add the non-natural amino acid to a peptide where a codon of the coding sequence calls for that particular tRNA. In other words, the codon for that particular tRNA has been reassigned to a non-natural amino acid. The recombinant polypeptide comprises 19 natural amino acids and at least one non-natural amino acid, where one natural amino acid in the polypeptide has been replaced by at least one non-natural amino acid. The successful substitution of a natural amino acid with a non-natural amino acid relies on the use of auxotrophic expression hosts deficient in the biosynthesis of that natural amino acid. Employment of such hosts limits competition from the natural amino acid for the reassigned sense codon, and improves the incorporation efficiency and yield of target proteins. Codons for many amino acids (including Met, Pro, Tyr, Phe, Leu, Val etc.) have been reassigned, and more than 60 non-natural amino acids have been incorporated into proteins via this method. See Hendrickson et al., "Incorporation of nonnatural amino acids into proteins," *Annu. Rev. Biochem.,* vol. 73, pages 147-176, 2004; Voloshchuk et al., "Incorporation of unnatural amino acids for synthetic biology," *Mol. Biosyst.,* vol. 6, pages 65-80, 2010, both incorporated herein by reference.

The main limitation of this method is that the non-natural amino acid will replace the natural amino acid throughout the polypeptide sequence, which may restrict its application if such global substitution is undesired. One solution is to mutate undesired sites (not to be substituted) to other natural amino acids so that only the desired substitute site(s) are reserved for the non-natural amino acid. With this modification, the method can introduce a non-natural amino acid site-specifically at any desired site to produce mimetic polypeptides.

Another method for producing mimetic recombinant polypeptide is by using wobble codons. Wobble codons refer to codons that are decoded by tRNAs via non-classical Watson-Crick base-pairing. The non-classical (or wobble) pairing is enabled through modification at the tRNA's $1^{st}$ anticodon base (which pairs with the 3rd base to the codon triplet), as proposed in the "Wobble Hypothesis". For example, many organisms have only one tRNA to decode two codons for Phe: UUU and UUC. As a result, the GAA anticodon on the tRNA binds to the UUC codon via Watson-Crick base-pairing, and to the UUU codon via "wobble" base-pairing.

Because of the wobble pairing between codon and anti-codon, one tRNA may pair with several codons, and a given codon may pair with more than one tRNA. Taking advantage of this property, a wobble codon may be assigned to a non-natural amino acid to generate a recombinant protein that contains natural amino acids and at least one non-natural amino acid. For example, Phe is normally encoded by two codons UUC and UUU, with both codons recognized by a single tRNA. By expressing an orthogonal pair of aminoacyl-tRNA synthetase and tRNA, with specificity for a non-natural amino acid and containing the "AAA" anti-codon, efficient introduction of the non-natural amino acid at UUU codons can be achieved (Kwon et al., "Breaking the degeneracy of the genetic code," *J. Am. Chem. Soc.,* vol. 125, pages 7512-7513, 2003, incorporated herein by reference). With this method, Phe can be essentially quantitatively assigned to the UUC codon, and a non-natural amino acid to the UUU wobble codon. Furthermore, multiple copies of a non-natural amino acid can be introduced site specifically into a polypeptide.

The third method for generating recombinant mimetic polypeptide is by using biased codons. The preferred codons differ between organisms, and even between different tissues or cell types of the same organism. The cellular content of tRNA species is a determining factor on the rate and amount of protein synthesized. As a consequence, recombinant protein production in heterologous host cells is often codon-optimized to match the preferred host cell codon bias (See for example the codon usage database for different organisms and codon analysis of a given gene as provided by Professor Toshimichi Ikemura at Laboratory of Evolutionary Genetics, National Institute of Genetics, Japan).

The biased codon usage provides another method to introduce non-natural amino acid into recombinant polypeptides. For example, out of the six degenerate codons for Arg, AGG and AGA are rarely used in *E. coli*. Introduction of an orthogonal pair of aminoacyl-tRNA synthetase and tRNA that pairs with the AGG codon into an *E. coli* expression host may enable linking a non-natural amino acid to the tRNA. Therefore, the tRNA with a non-natural amino acid linked can bring the non-natural amino acid to the codon AGG, where normally Arg may be encoded. This method has been proven feasible with an in vitro cell-free based system, where chemically synthesized non-natural amino acid linked tRNA that pairs with AGG coson was incorporated at AGG codons (Hohsaka et al., *FEBS Letters*, vol. 344, pages 171-174, 1994). The method could be adapted to *E. coli* cell-based expression system if an aminoacyl-tRNA synthetase can be engineered to link a non-natural orthogonal to a tRNA.

Similarly, a bias codon may be assigned to a non-natural amino acid in mammalian cells that exhibit codon bias. For example, through study of human papillomavirus gene expression in different mammalian cells, Frazer and his colleagues have found that papillomavirus protein expression is determined by the codon usage and tRNA availability. Substantial differences in the tRNA pools were discovered between differentiated and undifferentiated keratinocytes (Zhao et al., "Gene codon composition determines differentiation-dependent expression of a viral capsid gene in keratinocytes in vitro and in vivo," *Mol. Cell Biol.*, vol. 25, pages 8643-8655, 2005), and the observed bias in their tRNA may be the reason that papillomavirus replicates exclusively in epithelial cells. For example, in CHO and Cos 1 cells, it seems that TCG is a bias and thus might be assigned to a non-natural amino acid.

As the codon bias phenomenon is widespread in different eukaryotic organisms, utilization of such codons for site-specific incorporation of non-natural amino acids could be applied in many eukaryotic cell production hosts. The limitation would be the engineering of the aminoacyl-tRNA synthetase to link a non-natural orthogonal to a tRNA that can pair with a biased codon in the production hosts.

A fourth method for producing mimetic polypeptide is by suppressing a stop codon. Generally, protein translation terminates at one of the three stop codons (encoded by UAG (amber), UAA (ochre) and UGA (opal)) by the action of protein release factors (RF). However, occasional read-through of a stop codon with an amino acid has been observed to happen naturally in a variety of species. The suppression is caused by either mutations in the tRNA anticodon or mismatches of the codon-anticodon (Beier & Grimm, "Misreading of termination codons in eukaryotes by natural nonsense suppressor tRNAs," *Nucleic Acids Res.*, vol. 29, pages 4767-4782, 2001). Utilization of stop codon suppression represents another way to produce proteins containing non-natural amino acids, and generally involves the introduction of an aminoacyl-tRNA synthetase that can link a non-natural amino acid to a tRNA that can pair with a stop codon. For example, the aminoacyl-tRNA synthetase and tRNA that pairs with the amber stop codon have been developed to introduce a non-natural amino acid site-specifically at amber codons, as it is the least frequently used stop codon in both eukaryotic (23% in humans) and prokaryotic genomes (7% in *E. coli*) (Liu et al., "Genetic incorporation of unnatural amino acids into proteins in mammalian cells," *Nat. Methods*, vol. 4, pages 239-244, 2007). Ochre and opal stop codons have been used for the introduction of non-natural amino acids as well (Köhrer et al., "Complete set of orthogonal $21^{st}$ aminoacyl-tRNA synthetase-amber, ochre and opal suppressor tRNA pairs: concomitant suppression of three different termination codons in an mRNA in mammalian cells," *Nucleic Acids Res.*, vol. 32, pages 6200-6211, 2004). So far, over 70 non-natural amino acids have been site-specifically incorporated into recombinant proteins by this method (Liu & Schultz, "Adding new chemistries to the genetic code," *Annu. Rev. Biochem.*, vol. 79, pages 413-444, 2010). Typically, over 95% non-natural amino acid incorporation efficiency (defined as occupancy rate of non-natural amino acid in the full-length product) at the desired site can be obtained, making it one of the most frequently used methods for non-natural amino acid incorporation.

The present invention also encompasses any other techniques known to a person skilled in the art for introducing non-natural amino acids into a recombinant polypeptide. One such technique involves using four-base-pair codons (Anderson et al., "An expanded genetic code with a functional quadruplet codon. *Proc. Natl. Acad. Sci. U.S.A.*, vol. 101, pages 7566-7571, 2004). More discussion about producing mimetic recombinant polypeptides may be found in U.S. Pat. No. 7,045,337 and WO2010132341A2, incorporated herein by reference.

As discussed above, expression optimization for the conditionally active biologic protein in the eukaryotic cell production host can also be achieved by optimization of the vectors used (vector components, such as promoters, splice sites, 5' and 3' termini and flanking sequences), gene modification of host cells to reduce gene deletions and rearrangements, evolution of host cell gene activities by in vivo or in vitro methods of evolving relevant genes, optimization of host glycosylating enzymes by evolution of relevant genes, and/or by chromosome wide host cell mutagenesis and selection strategies to select for cells with enhanced expression capabilities. Host cells are further described herein.

In one aspect, codon mutagenesis is performed in the constant region of an antibody for optimization of eukaryotic cell expression. A codon optimized Fc variant with improved expression properties which retains the capacity to mediate effector functions improves the production of therapeutic antibodies. In this aspect, for example, a constant region of an antibody molecule can be evolved for screening in different expression hosts, for example, mammalian cell line expression screening utilizing CHO, HEK293 and COS-7.

The disclosure also provides methods for modifying the polypeptides of the disclosure by either natural processes, such as post-translational processing (e.g., phosphorylation, acylation, etc), or by chemical modification techniques. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, PEGylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W. H. Freeman and Company, New York (1993); Posttranslational Covalent Modification of Proteins, B. C. Johnson, Ed., Academic Press, New York, pp. 1-12 (1983).

The synthetic polypeptide or fragment thereof can be recovered and purified by known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The disclosure provides a preparation or formulation which comprises at least one conditionally active biologic protein, wherein the preparation is liquid or dry. The protein formulation optionally includes a buffer, a cofactor, a second or additional protein, and, optionally, one or more excipients. In one aspect the formulation is utilized as a therapeutic conditionally active biologic protein which is active under aberrant or non-physiological conditions, but less active or inactive under normal physiological conditions of, e.g., temperature, pH, osmotic pressure, oxidative stress and osmolality.

Standard purification techniques can be employed for either recombinant or synthetic conditionally active biologic proteins.

In some embodiments, the eukaryotic cell production host used for producing the conditionally active biologic protein is the same eukaryotic cell production host used for expressing the mutant DNAs generated from the evolving step. In one embodiment, the eukaryotic cell production host is a mammalian system selected from one of the group consisting of CHO, HEK293, IM9, DS-1, THP-1, Hep G2, COS, NIH 3T3, C33a, A549, A375, SK-MEL-28, DU 145, PC-3, HCT 116, Mia PACA-2, ACHN, Jurkat, MM1, Ovcar 3, HT 1080, Panc-1, U266, 769P, BT-474, Caco-2, HCC 1954, MDA-MB-468, LnCAP, NRK-49F, and SP2/0 cell lines; and mouse splenocytes and rabbit PBMC.

In one embodiment, a variety of mammalian cell production hosts can be used in the manufacture of candidates, including Fibroblast cells (3T3, mouse; BHK21, Syrian hamster) Epithelial cells (MDCK, dog; Hela, human; PtK1, rat kangaroo) Plasma cells ((SP2/0 and NS0, mouse) Kidney cells (293, human; COS, monkey) Ovary cells (CHO, Chinese hamster) and Embryonic cells (R1 and E14.1, mouse; H1 and H9, human; PER C.6, human).

In certain aspects, the recombinant conditionally active biologic antibodies are produced in CHO, NS0 and SP2/0 cell lines. In a specific aspect, the mammalian production host is a CHO-S cell line. Expression vector systems most frequently used are glutamine synthetase expression systems and others based on Dihydrofolate reductase genes.

In another embodiment, the eukaryotic cell production host is a yeast cell system. In one aspect, the yeast cell system is selected from S. cerevisiae or picchia cells.

In the method of the present invention, production hosts used for screening evolved molecules are the same as hosts used for downstream manufacturing of selected molecules. In another aspect of the present invention, the genetic system used for discovery and evolution of proteins is exactly the same as the genetic system used for manufacturing the protein for commercial applications.

Engineering Conditionally Active Biologic Proteins

The conditionally active biologic proteins of the present invention may be engineered by one or more protein engineering techniques described herein. Non-limiting examples of protein engineering techniques include antibody conjugation, engineering multispecific antibodies, and engineering the Fc region of the antibodies.

Engineering Conjugated Conditionally Active Antibodies

The conditionally active antibodies provided by the present invention may be conjugated to a molecule. Because the conditionally active antibody preferentially acts in brain, synovial fluid, a tumor microenvironment, or a stem cell niche, the conditionally active antibody may be conjugated to a molecule (therapeutic or diagnostic agent), which will be transported to the brain, synovial fluid or tumor microenvironment with the conditionally active antibody. In some embodiments, the molecule has toxicity, which may be reduced by being conjugated to the conditionally active antibody in order to preferentially act on the disease site.

The conjugation of the conditionally active antibody to a molecule (therapeutic or diagnostic) can be covalent or non-covalent. Covalent conjugation can either be direct or via a linker. In certain embodiments, direct conjugation is achieved by construction of a protein fusion (i.e., by genetic fusion of the two genes encoding the conditionally active antibody and, for example, a drug for treatment of a neurological disorder and expression as a single protein). In certain embodiments, direct conjugation is by formation of a covalent bond between a reactive group on one of the two portions of the conditionally active antibody and a corresponding group or acceptor on the neurological drug/imaging agent. In certain embodiments, direct conjugation is by modification (i.e., genetic modification) of one of the two molecules to be conjugated to include a reactive group (as non-limiting examples, a sulfhydryl group or a carboxyl group) that forms a covalent attachment to the other molecule to be conjugated under appropriate conditions. As one non-limiting example, a molecule (i.e., an amino acid) with a desired reactive group (i.e., a cysteine residue) may be introduced into, e.g., the conditionally active antibody and a disulfide bond formed with the neurological drug. Methods for covalent conjugation of nucleic acids to proteins are also known in the art (i.e., photocrosslinking, see, e.g., Zatsepin et al. Russ. Chem. Rev., 74: 77-95 (2005)) Non-covalent conjugation can be by any non-covalent attachment means, including hydrophobic bonds, ionic bonds, electrostatic interactions, and the like, as will be readily understood by one of ordinary skill in the art. Conjugation may also be performed using a variety of linkers. For example, a conditionally active antibody and a neurological drug may be conjugated using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptide linkers, comprised of from one to twenty amino acids joined by peptide bonds, may also be used. In certain such embodiments, the amino acids are selected from the twenty naturally-occurring amino acids. In certain other such embodiments, one or more of the amino acids are selected from glycine, alanine, proline, asparagine, glutamine and lysine. The linker may be a "cleavable linker" facilitating release of the neurological drug upon delivery to the brain. For example, an acid-labile linker, peptidase-sensitive linker, photolabile linker, dimethyl linker or disulfide-containing linker (Chari et al., Cancer Res., 52:127-131 (1992); U.S. Pat. No. 5,208,020) may be used. Some examples of cross-linker reagents for antibody conjugation include BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate)

The conjugated therapeutic agent may be toxic to the body, such as a radioactive particle, chemotherapy drug, or a cell toxin (i.e., cytotoxin). Using the conditionally active antibodies of the present invention to deliver the conjugated therapeutic agent to the disease site will significantly reduce the toxic effects of these therapeutic agents. The technology for conjugating radioactive particles to antibodies is known in the art. Ibritumomab tiuxetan (Zevalin®) and tositumomab (Bexxar®) are examples of radioactive particle conjugated monoclonal antibodies. Both are antibodies against the CD20 antigen conjugated with a different radioactive particle. Similarly, the technology for conjugating chemotherapy drugs to antibodies is also known in the art. There are two marketed antibodies that are conjugated with a chemotherapy drug: brentuximab vedotin (Adcetris®) and ado-trastuzumab emtansine (Kadcyla™). Brentuximab vedotin is made up of an antibody that targets the CD30 antigen (found on B cells and T cells), attached to a chemotherapy drug called MMAE. Ado-trastuzumab emtansine is made of an antibody that targets the HER2 protein attached to a chemotherapy drug called DM1. The technology for conjugating a cell toxin to an antibody is also known in the art. For example, denileukin diftitox (Ontak®, a cancer drug) consists of an immune system protein known as interleukin-2 (IL-2) attached to a toxin from the germ that causes diphtheria.

It is contemplated that any radioactive particles, chemotherapy drugs and cell toxins may be conjugated to the conditionally active antibody of the present invention in order to reduce the side effects of these agents.

In some embodiments, the radioactive particles are conjugated to the conditionally active antibodies for treatment of abnormal tissue. The radioactive particles may comprise particles impregnated with one or more radioactive isotopes, and typically have sufficient radioactivity for locoregional ablation of cells in the abnormal tissue. The particles may comprise glass, metal, resin, albumin, or polymer. Metal in the radioactive particles may be selected from iron, gadolinium, and calcium. Examples of the one or more radioactive isotopes in the radioactive particles are selected from the group consisting of Gallium-67 ($^{67}$Ga), Yttrium-90 ($^{90}$Y), Gallium-68 ($^{68}$Ga), Thallium-201 ($^{201}$Tl), Strontium-89 ($^{89}$Sr), Indium-III ($^{111}$In), Iodine-131 ($^{131}$I), Samarium-153 ($^{153}$Sm), Technetium-99m ($^{99m}$Tc), Rhenium-186 ($^{186}$Re), Rhenium-188 ($^{188}$Re), Copper-62 ($^{62}$Cu), and Copper-64 ($^{64}$Cu). Preferably the radioactive isotope(s) in the composition emit beta radiation, gamma radiation, and/or positrons.

In some embodiments, the chemotherapy drugs conjugated to the conditionally active antibodies are selected from the group consisting of anthracyclines, topoisomerase I and/or II inhibitors, spindle poison plant alkaloids, alkylating agents, anti-metabolites, purine or pyrimidine analogues, antifolates, ellipticine and harmine.

Anthracyclines (or anthracycline antibiotics) are derived from *Streptomyces* bacteria. These compounds are used to treat a wide range of cancers, including for example hepatocellular carcinoma, leukemias, lymphomas, breast, uterine, ovarian, and lung cancers. Anthracyclines include, but are not limited to doxorubicin, daunorubicin, epirubicin, idarubicin, valrubicin, pirarubicin, zorubicin, aclarubicin, detorubicin, carminomycin, morpholinodoxorubicin, morpholinodaunorubicin, methoxymorpholinyldoxorubicin, and their pharmaceutically acceptable salts thereof.

Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecin derivatives Camptothecin derivatives refer to camptothecin analogs such as irinotecan, topotecan, hexatecan, silatecan, lutortecan, karenitecin (BNP1350), gimatecan (ST1481), belotecan (CKD602), and their pharmaceutically acceptable salts. Examples of type II topoisomerase inhibitors include, but are not limited to, amsacrine, etoposide, etoposide phosphate and teniposide. These are semisynthetic derivatives of epipodophyllotoxins, alkaloids naturally occurring in the root of the American Mayapple (*Podophyllum peltatum*).

Spindle poison plant alkaloids are derived from plants and block cell division by preventing microtubule function, essential for cell division. These alkaloids include, but are not limited to, *vinca* alkaloids (like vinblastine, vincristine, vindesine, vinorelbine and vinpocetine) and taxanes. Taxanes include, but are not limited to, paclitaxel, docetaxel, larotaxel, cabazitaxel, ortataxel, tesetaxel, and their pharmaceutically acceptable salts.

Alkylating agents are so named because of their ability to add alkyl groups to many electronegative groups under conditions present in cells. They impair cell function by forming covalent bonds with the amino, carboxyl, sulfhydryl, and phosphate groups in biologically important molecules. Noteworthy, their cytotoxicity is thought to result from inhibition of DNA synthesis. Alkylating agents include, but are not limited to, mechlorethamine, cyclophosphamide, chlorambucil, ifosfamide and platinum compounds such as oxaliplatin, cisplatin or carboplatin.

An anti-metabolite is a chemical that inhibits the use of a metabolite, which is part of normal metabolism. Such substances are often similar in structure to the metabolite that they interfere with. The presence of anti-metabolites alters cell growth and cell division.

Purine or pyrimidine analogues prevent the incorporation of nucleotides into DNA, stopping DNA synthesis and thus cell divisions. They also affect RNA synthesis. Examples of purine analogues include azathioprine, mercaptopurine, thioguanine, fludarabine, pentostatin and cladribine. Examples of pyrimidine analogues include 5-fluorouracil (5FU), which inhibits thymidylate synthase, floxuridine (FUDR) and cytosine arabinoside (Cytarabine).

Antifolates are chemotherapy drugs which impair the function of folic acids. A well-known example is Methotrexate, which is a folic acid analogue that inhibits the enzyme dihydrofolate reductase (DHFR), and thus prevents the formation of tetrahydrofolate. Tetrahydrofolate is essential for purine and pyrimidine synthesis. This leads to inhibited production of DNA, RNA and proteins (as tetrahydrofolate is also involved in the synthesis of amino acids serine and methionine). Other antifolates include, but are not limited to, trimethoprim, raltitrexed, pyrimethamine and pemetrexed.

Other chemotherapy drugs may also be conjugated to the conditionally active antibodies, such as ellipticine and harmine. Ellipticine is a natural plant alkaloid product which was isolated from the evergreen tree of the Apocynaceae family. Ellipticine and its derivatives such as 9-hydroxyellipticinium, N2-methyl-9-hydroxyellipticinium, 2-(diethyiamino-2-ethyl)9-hydroxyellipticinium acetate, 2-(diisopropylamino-ethyl)9-hydroxy-ellipticinium acetate and 2-(beta piperidino-2-ethyl)9-hydroxyellipticinium are all effective chemotherapy drugs.

Harmine is a natural plant alkaloid product which was isolated from the Peganum harmala seeds. Harmine-based chemotherapy drugs include harmine, harmaline, harmol, harmalol and harman, and quinazoline derivatives: vasicine and vasicinone.

In some embodiments, the cell toxins conjugated to the conditionally active antibodies include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diptheria toxin, and snake venom (e.g., cobra venom).

In some embodiment, the conditionally active antibodies of the present invention may be conjugated to a diagnostic agent. A diagnostic agent used in the present invention can include any diagnostic agent known in the art, as provided, for example, in the following references: Armstrong et al, Diagnostic Imaging, 5$^{th}$ Ed., Blackwell Publishing (2004); Torchilin, V. P., Ed., Targeted Delivery of Imaging Agents, CRC Press (1995); Vallabhajosula, S., Molecular Imaging: Radiopharmaceuticals for PET and SPECT, Springer (2009). A diagnostic agent can be detected in a variety of ways, including using the agent to provide and/or enhance a detectable signal that includes, but is not limited to, gamma-emissions, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

In some embodiments, a diagnostic agent can include chelators that bind, e.g., to metal ions to be used for a variety of diagnostic imaging techniques. Exemplary chelators include but are not limited to ethylenediaminetetraacetic acid (EDTA), [4-(1,4,8,11-tetraazacyclotetradec-1-yl) methyl]benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra(methylene phosphonic acid) (DOTP), 1,4,8,11-tetraazacyclododecane-1,4,8,11-tetraacetic acid (TETA), 1,4,7,10-tetraazacyclododecane-1,4,7,10-tetraacetic acid (DOTA), and derivatives thereof.

A radioisotope can be incorporated into some of the diagnostic agents described herein and can include radionuclides that emit gamma rays, positrons, beta and alpha particles, and X-rays. Suitable radionuclides include but are not limited to Ac, As, At, $^n$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^3$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^m$In-DTPA, $^{99m}$Tc(CO)3-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, the liposomes can be radiolabeled, for example, by incorporation of lipids attached to chelates, such as DTPA-lipid, as provided in the following references: Phillips et al, Wiley Interdisciplinary Reviews: *Nanomedicine and Nanobiotechnology*, vol. 1, pages 69-83 (2008); Torchilin, V. P. & Weissig, V., Eds. Liposomes 2nd Ed.:Oxford Univ. Press (2003); Elbayoumi, T. A. & Torchilin, V. P., *Eur. J. Nucl. Med. Mol. Imaging*, 33: 1196-1205 (2006); Mougin-Degraef, M. et al, *Int'l J. Pharmaceutics*, 344: 110-117 (2007).

In other embodiments, the diagnostic agents may include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to, cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difiuoro-4-bora-3a,4a-diaza-s-indacene, and/or conjugates and/or derivatives of any of these. Other agents that can be used include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine (NIRD)-polyaspartic acid conjugates, isosulfan blue, indole disulfonates, benzoindole disulfonate, bis(ethylcarboxymethyl)indocyanine, bis (pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N, N',N'-tetrakis(carboxymethyl)amino]pyrazine, 3,6-[(N,N, N',N'-tetrakis(2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S- dioxide, indocarbocyaninetetrasulfonate, chloroindocarbocyanine, and 3,6-diaminopyrazine-2,5-dicarboxylic acid.

In yet other embodiments, the diagnostic agents may include contrast agents that are generally well known in the art, including, for example, superparamagnetic iron oxide (SPIO), complexes of gadolinium or manganese, and the like. (See, e.g., Armstrong et al, Diagnostic Imaging, 5$^{th}$ Ed., Blackwell Publishing (2004)). In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to Gadopentetic acid, Gadoteric acid, Gadodiamide, Gadolinium, Gadoteridol, Mangafodipir, Gadoversetamide, Ferric ammonium citrate, Gadobenic acid, Gadobutrol, or Gadoxetic acid. Superparamagnetic agents can include but are not limited to superparamagnetic iron oxide and Ferristene. In certain embodiments, the diagnostic agents can include x-ray contrast agents as provided, for example, in the following references: H. S Thomsen, R. N. Muller and R. F. Mattrey, Eds., Trends in Contrast Media, (Berlin: Springer-Verlag, 1999); P. Dawson, D. Cosgrove and R. Grainger, Eds., Textbook of Contrast Media (ISIS Medical Media 1999); Torchilin, V. P., Curr. Pharm. Biotech., vol. 1, pages 183-215 (2000); Bogdanov, A. A. et al, Adv. Drug Del. Rev., Vol. 37, pages 279-293 (1999); Sachse, A. et ah, Investigative Radiology, vol. 32, pages 44-50 (1997). Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexol, iopentol, ioversol, iobitridol, iodixanol, iotrolan and iosimenol.

In some embodiments, the conditionally active antibody may be conjugated to a protein, such as interleukins, cytokines, enzymes, growth factors, or other antibodies. Some examples of such proteins include, for example, tumor necrosis factor, α-interferon (EFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in WO 97/33899), AIM II (see WO 97/34911), Fas Ligand (Takahashi et al., J. Immunol., vol. 6, pages 1567-1574, 1994), and VEGI (WO 99/23105), a thrombotic agent or an anti-angiogenic agent (e.g., angiostatin or endostatin); or a biologic response modifier such as, for example, a lymphokine (e.g., interleukin-1 ("IL-I"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

In some embodiments, the conditionally active antibodies for crossing the BBB as provided by the present invention may be conjugated to a drug for treating a neurological disorder. The drug will be transported across the BBB with the antibodies and remain in the brain for treating the neurological disorder. The neurological disorder refers to a disease or disorder which affects the CNS and/or which has an etiology in the CNS. Exemplary CNS diseases or disorders include, but are not limited to, neuropathy, amyloidosis, cancer, an ocular disease or disorder, viral or microbial infection, inflammation, ischemia, neurodegenerative disease, seizure, behavioral disorders, and a lysosomal storage disease. For the purpose of this application, CNS will be understood to include the eye, which is normally sequestered from the rest of the body by the blood-retina barrier. Specific examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g. of the CNS and/or brain, including brain metastases resulting from cancer elsewhere in the body).

Drugs for treating the neurological disorder include, but are not limited to, antibodies, peptides, proteins, natural ligands of one or more CNS target(s), modified versions of natural ligands of one or more CNS target(s), aptamers, inhibitory nucleic acids (i.e., small inhibitory RNAs (siRNA), and short hairpin RNAs (shRNA)), ribozymes, and small molecules, or active fragments of any of the foregoing. Exemplary neurological disorder drugs include, but are not limited to: antibodies, aptamers, proteins, peptides, inhibitory nucleic acids and small molecules and active fragments of any of the foregoing that either are themselves or specifically recognize and/or act upon (i.e., inhibit, activate, or detect) a CNS antigen or target molecule such as, but not limited to, amyloid precursor protein or portions thereof, amyloid beta, beta-secretase, gamma-secretase, tau, alpha-synuclein, parkin, huntingtin, DR6, presenilin, ApoE, glioma or other CNS cancer markers, and neurotrophins. Non-limiting examples of neurological disorder drugs and disorders they may be used to treat include anti-BACE1 antibody for treating Alzheimer's, acute and chronic brain injury, stroke; anti-Abeta antibody for treating Alzheimer's disease; neurotrophin for treating stroke, acute brain injury, spinal cord injury; brain-derived neurotrophic factor (BDNF) and fibroblast growth factor 2 (FGF-2) for treating chronic brain injury (neurogenesis); anti-Epidermal Growth Factor Receptor (EGFR)-antibody for treating brain cancer; Glial cell-line derived neural factor (GDNF) for treating Parkinson's disease; brain-derived neurotrophic factor (BDNF) for treating Amyotrophic lateral sclerosis and depression; lysosomal enzyme for treating lysosomal storage disorders of the brain; Ciliary neurotrophic factor (CNTF) for treating Amyotrophic lateral sclerosis; Neuregulin-1 for treating Schizophrenia; and anti-HER2 antibody (e.g. trastuzumab) for treating brain metastasis from HER2-positive cancer.

In some embodiments, the conjugation of the conditionally active antibodies may be on the Fc region of these antibodies. The conjugating molecules, compounds or drugs described above may be conjugated to the Fc region, as described in U.S. Pat. No. 8,362,210 (incorporated herein by reference). For example, the Fc region may be conjugated to a cytokine or a toxin to be delivered to the site where the conditionally active antibody displays preferential activity. Methods for conjugating polypeptides to the Fc region of antibodies are known in the art. See, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., *Proc. Natl. Acad. Sci. USA*, vol. 88, pages 10535-10539, 1991; Traunecker et al., *Nature*, vol. 331, pages 84-86, 1988; Zheng et al., *J. Immunol.*, vol. 154, pages 5590-5600, 1995; and Vil et al., *Proc. Natl. Acad. Sci. USA*, vol. 89, pages 11337-11341, 1992, which are incorporated herein by reference in their entireties.

Engineering Multispecific Conditionally Active Antibodies

A multispecific antibody is an antibody with polyepitopic specificity. Multispecific antibodies include, but are not limited to, an antibody comprising a heavy chain variable domain ($V_H$) and a light chain variable domain (VL), where the $V_H V_L$ unit has polyepitopic specificity, antibodies having two or more $V_L$ and $V_H$ domains where each $V_H V_L$ unit binds to a different epitope, antibodies having two or more single variable domains with each single variable domain binding to a different epitope, and antibodies comprising one or more antibody fragments as well as antibodies comprising antibody fragments that have been linked covalently or non-covalently.

To construct multispecific antibodies, including bispecific antibodies, antibody fragments having at least one free sulfhydryl group are obtained. The antibody fragments may be obtained from full-length conditionally active antibodies. The conditionally active antibodies may be digested enzymatically to produce antibody fragments. Exemplary enzymatic digestion methods include, but are not limited to, pepsin, papain and Lys-C. Exemplary antibody fragments include, but are not limited to, Fab, Fab', F(ab')2, Fv, diabodies (Db); tandem diabodies (taDb), linear antibodies (see U.S. Pat. No. 5,641,870; Zapata et al., *Protein Eng.*, vol. 8, pages 1057-1062 (1995)); one-armed antibodies, single variable domain antibodies, minibodies (Olafsen et al (2004) *Protein Eng. Design & Sel.*, vol. 17, pages 315-323), single-chain antibody molecules, fragments produced by a Fab expression library, anti-idiotypic (anti-Id) antibodies, complementary determining regions (CDRs), and epitope-binding fragments. Antibody fragments may also be produced using DNA recombinant technology. The DNA encoding the antibody fragments may be cloned into plasmid expression vectors or phagemid vectors and expressed directly in *E. Coli*. Antibody enzymatic digestion methods, DNA cloning and recombinant protein expression methods are well known to those skilled in the art.

Antibody fragments may be purified using conventional techniques and may be subjected to reduction to generate a free thiol group. Antibody fragments having a free thiol group may be reacted with a crosslinker, for example, bis-maleimide. Such crosslinked antibody fragments are purified and then reacted with a second antibody fragment having a free thiol group. The final product in which two antibody fragments are crosslinked is purified. In certain embodiments, each antibody fragment is a Fab and the final product, in which the two Fabs are linked through bis-maleimide, is referred to herein as bismaleimido-(thio-Fab) 2, or bis-Fab. Such multispecific antibodies and antibody analogs, including bis-Fabs, can be exploited to quickly synthesize a large number of antibody fragment combinations, or structural variants of native antibodies or particular antibody fragment combinations.

Multispecific antibodies can be synthesized with modified crosslinkers such that additional functional moieties may be attached to the multispecific antibodies. Modified crosslinkers allow for attachment of any sulfhydryl-reactive moiety. In one embodiment, N-succinimidyl-S-acetylthioacetate (SATA) is attached to bis-maleimide to form bis-maleimido-acetylthioacetate (BMata). After deprotection of the masked thiol group, any functional group having a sulfhydryl-reactive (or thiol-reactive) moiety may be attached to the multispecific antibodies.

Exemplary thiol-reactive reagents include a multifunctional linker reagent, a capture, i.e. an affinity, label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). Such multispecific antibodies or antibody analogs having modified crosslinkers may be further reacted with a drug moiety reagent or other label. Reaction of a multispecific antibody or antibody analog with a drug-linker intermediate provides a multispecific antibody drug conjugate or antibody analog drug conjugate, respectively.

Many other techniques for making multispecific antibodies may also be used in the present invention. References (incorporated herein by reference) describing these techniques include: (1) Milstein and Cuello, *Nature*, vol. 305, page 537 (1983)), WO 93/08829, and Traunecker et al., *EMBO J.*, vol. 10, page 3655 (1991) on recombinant co-expression of two immunoglobulin heavy chain-light chain pairs having different specificities; (2) U.S. Pat. No. 5,731,168 on "knob-in-hole" engineering; (3) WO 2009/089004A1 on engineering electrostatic steering effects for making antibody Fc-heterodimeric molecules; (4) U.S. Pat. No. 4,676,980, and Brennan et al., *Science*, vol. 229, page 81 (1985) on cross-linking two or more antibodies or fragments; (5) Kostelny et al., *J. Immunol.*, vol. 148, pages 1547-1553 (1992) on using leucine zippers to produce bi-specific antibodies; (6) Hollinger et al., *Proc. Natl. Acad. Sci. USA*, vol. 90, pages 6444-6448 (1993) on using "diabody" technology for making bispecific antibody fragments; (7) Gruber et al., *J. Immunol.*, vol. 152, page 5368 (1994) on using single-chain Fv (sFv) dimers; (8) Tutt et al. *J. Immunol.* 147: 60 (1991) on preparing trispecific antibodies; and (9) US 2006/0025576A1 and Wu et al. *Nature Biotechnology*, vol. 25, pages 1290-1297 (2007) on engineered antibodies with three or more functional antigen binding sites, including "Octopus antibodies" or "dual-variable domain immunoglobulins" (DVDs).

Multispecific antibodies of the present invention may also be generated as described in WO/2011/109726, incorporated herein by reference in its entirety.

In one embodiment, the conditionally active antibody for crossing the BBB is engineered to make a multispecific antibody (e.g. a bispecific antibody). This multispecific antibody comprises a first antigen binding site which binds a BBB-R and a second antigen binding site which binds a brain antigen. At least the first antigen binding site for BBB-R is conditionally active. A brain antigen is an antigen expressed in the brain, which can be targeted with an antibody or small molecule. Examples of such antigens include, without limitation: beta-secretase 1 (BACE1), amyloid beta (Abeta), epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In one embodiment, the antigen is BACE1.

In some embodiments, the multispecific antibodies may target antigens that engage cancer-treating cells, such as NK cells and other cells mentioned herein, to activate the cancer-treating cells by acting as immune effector cells. One example of this is a CAR that targets the CD16A antigen to engage NK cells to fight CD30-expressing malignancies. The bispecific, tetravalent AFM13 antibody is an example of an antibody that can deliver this effect. Further details of this type of embodiment can be found, for example, in Rothe, A., et al., "A phase 1 study of the bispecific anti-CD30/CD16A antibody construct AFM13 in patients with relapsed or refractory Hodgkin lymphoma," *Blood*, vol. 125, no. 26, pp. 4024-4031, 2015.

Multispecific antibodies have a high selectivity for preferentially targeting tissues containing all or most of the targets (antigens) that a multispecific antibody can bind to. For example, a bispecific antibody may provide selectivity for target cells by displaying greater preference to target cells that express both of the antigens recognized by the bispecific antibody, in comparison with non-target cells that may express only one of the antigens. Therefore, due to the dynamism of the system, more bispecific antibodies are bound to the target cells than non-target cells at equilibrium.

Engineering the Conditionally Active Antibodies for Crossing BBB

The BBB has endogenous transport systems that are mediated by a BBB receptor (BBB-R), which is a specific receptor that allows transport of macromolecules across the BBB. For example, an antibody that can bind to a BBB-R may be transported across BBB using the endogenous transport systems. Such an antibody may serve as a vehicle for transport of drugs or other agents across BBB by using the endogenous BBB receptor mediated transport system that traverses the BBB. Such antibodies need not have high affinity to a BBB-R. Antibodies that are not conditionally active antibodies with low affinities for BBB-R have been described as crossing the BBB more efficiently than a high affinity antibody, as described in US 2012/0171120 (incorporated herein by reference).

Another method for engineering antibodies to enter the brain is to engineer antibodies to be delivered to the brain via the central nervous system lymphatic vessels. Thus, the antibodies can be engineered to bind to or mimic immune cells such as T-cells, or synovial or cerebrospinal fluids that travel to the central nervous system via lymphatic vessels. Details of the lymphatic vessels of the central nervous system are described in, for example, Louveau, A., et al., "Structural and functional features of central nervous system lymphatic vessels," *Nature* 523, pp. 337-341, 16 Jul. 2015 and the articles citing this article that are publicly available as of the date of filing of this application, all of which are hereby incorporated by reference in their entirety herein for the purpose of providing details of the central nervous system lymphatic system and the fluids and cells that travel in this system.

Unlike traditional antibodies, conditionally active antibodies are not required to have low affinity for BBB-R to cross the BBB and remain inside the brain. Conditionally active antibodies can have high affinity for the BBB-R on the blood side of the BBB, and little or no affinity on the brain side of the BBB. Drugs, such as drug conjugates, may be coupled to a conditionally active antibody to be transported with the antibody across the BBB into the brain.

A BBB-R is a transmembrane receptor protein expressed on brain endothelial cells which is capable of transporting molecules across the blood-brain barrier. Examples of BBB-R include transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). An exemplary BBB-R herein is a transferrin receptor (TfR). The TfR is a transmembrane glycoprotein (with a molecular weight of about 180,000) composed of two disulphide-bonded sub-units (each of apparent molecular weight of about 90,000) involved in iron uptake in vertebrates.

In some embodiments, the present invention provides a conditionally active antibody generated from a parent or wild-type antibody against a BBB-R. The conditionally active antibody binds the BBB-R on the blood side of the BBB, and has a lower affinity to the BBB-R than the parent or wild-type antibody on the brain side of the BBB. In some other embodiments, the conditionally active antibody has affinity to the BBB-R than the wild type or parent antibody on the blood side of the BBB, and has no affinity to the BBB-R on the brain side of the BBB.

Blood plasma is a body fluid that is very different from brain extracellular fluid (ECF). As discussed by Somjen ("Ions in the Brain: Normal Function, Seizures, and Stroke," Oxford University Press, 2004, pages 16 and 33) and Redzic ("Molecular biology of the blood-brain and the blood-cerebrospinal fluid barriers: similarities and differences," *Fluids and Barriers of the CNS*, vol. 8:3, 2011), the brain extracellular fluid has significantly less $K^+$, more $Mg^{2+}$ and $H^+$ than blood plasma. The differences in ion concentrations between blood plasma and brain ECF lead to significant differences in osmotic pressure and osmolality between the two fluids. Table 1 shows the concentrations of common ions in millimoles for both blood plasma and brain ECF.

TABLE 1

Common ions in plasma (arterial plasma) and brain extracellular fluid (CSF)

| | ARTERIAL PLASMA | | CSF | |
| --- | --- | --- | --- | --- |
| | HUMAN | RAT | HUMAN | RAT |
| $Na^+$ | 150 | 148 | 147 | 152 |
| $K^+$ | 4.6 | 5.3 | 2.9 | 3.4 |
| Ca, total | 2.4 | 3.1 | 1.14 | 1.1 |
| $Ca^{2+}$, free pCa | 1.4 | 1.5 | 1.0 | 1.0 |
| Mg, total | 0.86 | 0.8 | 1.15 | 1.3 |
| $Mg^{2+}$, free | 0.47 | 0.44 | 0.7 | 0.88 |
| $H^+$ | 0.000039 | 0.000032 | 0.000047 | 0.00005 |
| pH | 7.41 | 7.5 | 7.3 | 7.3 |
| $Cl^-$ | 99 | | 119 | |
| $HCO_3^-$ | 26.8 | 31 | 23.3 | 28 |

Brain ECF also contains significantly more lactate than blood plasma and significantly less glucose than blood plasma (Abi-Saab et al., "Striking Differences in Glucose and Lactate Levels Between Brain Extracellular Fluid and Plasma in Conscious Human Subjects: Effects of Hyperglycemia and Hypoglycemia," Journal of Cerebral Blood Flow & Metabolism, vol. 22, pages 271-279, 2002).

Thus, there are several physiological conditions that are different between the two sides of the BBB, such as pH, concentrations of various substances (such as lactose, glucose, K+, Mg2+), osmotic pressure and osmolality. For the physiological condition of pH, human blood plasma has a higher pH than human brain ECF. For the physiological condition of K+ concentration, brain ECF has a lower K+ concentration than human blood plasma. For the physiological condition of Mg2+ concentration, the human brain ECF has significantly more Mg2+ than human blood plasma. For the physiological condition of osmotic pressure, the human brain ECF has an osmotic pressure that is different from that of human blood plasma. In some embodiments, the physiological conditions of brain ECF may be the composition, pH, osmotic pressure and osmolality of brain ECF of patients with a particular neurological disorder, which may be different from the physiological condition of the brain ECF of the general population.

The present invention thus provides a method for evolving a DNA that encodes a template antibody against a BBB-R to create a mutant DNA library. The mutant DNA library is then expressed to obtain mutant antibodies. The mutant antibodies are screened for a conditionally active antibody that has binds to the BBB-R under at least one blood plasma physiological condition and has a low or no affinity to the BBB-R under at least one brain physiological condition in the brain ECF compared to the template antibody. Thus, the selected mutant antibody has a low or high affinity to the BBB-R at the blood plasma side and a low or no affinity to the BBB-R at the brain ECF side. This selected mutant antibody is useful as a conditionally active antibody for transport across the BBB.

Such a conditionally active antibody is advantageous for crossing the BBB and remaining in the brain ECF. The low affinity to the BBB-R at the brain side lowers the rate (or removes) the conditionally active antibody is transported back across the BBB out of the brain and back into the blood relative to the template antibody.

In some other embodiments, the present invention provides a method for evolving a DNA that encodes a template antibody against a BBB-R to create a mutant DNA library. The mutant DNA library is then expressed to obtain mutant antibodies. The mutant antibodies are screened for a conditionally active antibody that binds to the BBB-R under at least one blood plasma physiological condition and little or no affinity to the BBB-R under at least one brain physiological condition. Thus, the selected mutant antibody has affinity to the BBB-R at the plasma side and little or no affinity to the BBB-R at the brain ECF side. This selected mutant antibody is a conditionally active antibody.

Such a conditionally active antibody is advantageous in crossing the BBB and remaining in the brain ECF. After binding to the BBB-R at the blood plasma side, the conditionally active antibody is transported across the BBB, and the little to no affinity to the BBB-R at the brain ECF side means that the conditionally active antibody is unlikely to be transported out of the brain.

The affinity of the conditionally active antibody to a BBB-R may be measured by its half maximal inhibitory concentration (IC50), which is a measure of how much of the antibody is needed to inhibit the binding of a known BBB-R ligand to the BBB-R by 50%. A common approach is to perform a competitive binding assay, such as competitive ELISA assay. An exemplary competitive ELISA assay to measure IC50 on TfR (a BBB-R) is one in which increasing concentrations of anti-TfR antibody compete against biotinylated $TfR^A$ for binding to TfR. The anti-TfR antibody competitive ELISA may be performed in Maxisorp plates (Neptune, N.J.) coated with 2.5 μg/ml of purified murine TfR extracellular domain in PBS at 4° C. overnight. Plates are washed with PBS/0.05% Tween 20 and blocked using Superblock blocking buffer in PBS (Thermo Scientific, Hudson, N.H.). A titration of each individual anti-TfR antibody (1:3 serial dilution) is combined with biotinylated anti-$TfR^A$ (0.5 nM final concentration) and added to the plate for 1 hour at room temperature. Plates are washed with PBS/0.05% Tween 20, and HRP-streptavidin (Southern Biotech, Birmingham) is added to the plate and incubated for 1 hour at room temperature. Plates are washed with PBS/0.05% Tween 20, and biotinylated anti-$TfR^A$ bound to the plate is detected using TMB substrate (BioFX Laboratories, Owings Mills).

A high IC50 indicates that more of the conditionally active antibody is required to inhibit binding of the known ligand of a BBB-R, and thus that the antibody's affinity for that BBB-R is relatively low. Conversely, a low IC50 indicates that less of the conditionally active antibody is required to inhibit binding of the known ligand, and thus that the antibody's affinity for that BBB-R is relatively high.

In some embodiments, the IC50 of the conditionally active antibodies from a BBB-R in the blood plasma may be from about 1 nM to about 100 μM, or from about 5 nM to about 100 μM, or from about 50 nM to about 100 μM, or from about 100 nM to about 100 μM, or from about 5 nM to about 10 μM, or from about 30 nM to about 1 μM, or from about 50 nM to about 1 μM.

Engineering Conditionally Active Biologic Proteins for Synovial Fluid

Joint diseases are a major cause of disability and early retirement in the industrialized countries. Joint diseases often lead to damage at a joint which is difficult to repair. Synovial fluid is a body fluid that is found in the synovial cavity of the joints (e.g., knee, hip, shoulder) of a human or animal body between the cartilage and synovium of facing articulating surfaces. Synovial fluid provides nourishment to the cartilage and also serves as a lubricant for the joints. The cells of the cartilage and synovium secrete fluid that serve as a lubricant between the articulating surfaces. Human synovial fluid comprises approximately 85% water. It is derived from the dialysate of blood plasma, which itself is made up of water, dissolved proteins, glucose, clotting factors, mineral ions, hormones, etc. Proteins such as albumin and globulins are present in synovial fluid and are believed to play an important role in the lubricating the joint area. Some other proteins are also found in human synovial fluid, including the glycoproteins such as alpha-1-acid glycoprotein (AGP), alpha-1-antitrypsin (A1AT) and lubricin.

Synovial fluid has a composition that is very different from other parts of the body. Thus, synovial fluid has physiological conditions that are different from other parts of the body, such as the blood plasma. For example, synovial fluid has less than about 10 mg/dL of glucose whereas the mean normal glucose level in human blood plasma is about 100 mg/dL, fluctuating within a range between 70 and 100 mg/dL throughout the day. In addition, the total protein level in the synovial fluid is about one third of the blood plasma protein level since large molecules such as proteins do not easily pass through the synovial membrane into the synovial fluid. It has also been found that the pH of human synovial fluid is higher than the pH in human plasma (Jebens et al., "On the viscosity and pH of synovial fluid and the pH of blood," The Journal of Bone and Joint Surgery, vol. 41 B, pages 388-400, 1959; Farr et al., "Significance of the hydrogen ion concentration in synovial fluid in Rheumatoid Arthritis," Clinical and Experimental Rheumatology, vol. 3, pages 99-104, 1985).

Thus, the synovial fluid has several physiological conditions that are different from those of the other parts of body, such as the physiological conditions in the blood plasma. The synovial fluid has a pH that is higher than other parts of the body, especially the blood plasma. The synovial fluid has a lower concentration of glucose than other parts of the body, such as blood plasma. The synovial fluid also has a lower concentration of protein than other parts of the body, such as blood plasma.

Several antibodies have been used to treat joint disease by introducing the antibodies into the synovial fluid. For example, the synovial fluid in an injured joint is known to contain many factors which have an influence on the progression of osteoarthritis (see, for example, Fernandes, et al., "The Role of Cytokines in Osteoarthritis Pathophysiology", *Biorheology*, vol. 39, pages 237-246, 2002). Cytokines, such as Interleukin-1 (IL-I) and Tumor Necrosis Factor-α (TNF-α), which are produced by activated synoviocytes, are known to upregulate matrix metalloproteinase (MMP) gene expression. Upregulation of MMP leads to degradation of the matrix and non-matrix proteins in the joints. Antibodies that neutralize cytokines may stop the progression of osteoarthritis.

Using antibodies as drug is a promising strategy for the treatment of joint diseases. For example, antibodies (such as antibody against aggrecan or aggrecanase) have been developed to treat osteoarthritis, which has by far the greatest prevalence among joint diseases (WO1993/022429A1). An antibody against acetylated high-mobility group box 1 (HMGB1) has been developed for diagnosis or treatment of joint diseases that are inflammatory, autoimmune, neurodegenerative or malignant diseases/disorders, such as arthritis. This antibody may be used to detect the acetylated form of HMGB1 in synovial fluid (WO 2011/157905A1). Another antibody (CD20 antibody) has also been developed to treat damage to connective tissue and cartilage of the joints.

However, the antigens of these antibodies are often expressed in other parts of the body carrying important physiological functions. Antibodies against these antigens, though efficacious in treating joint diseases, may also significantly interfere with the normal physiological functions of these antigens in other parts of the body. Therefore, severe side effects may be experienced by patients. It is thus desirable to develop therapeutics, such as antibodies against cytokines or other antigens that can preferentially bind to their antigens (proteins or other macromolecules) at higher affinity in the synovial fluid, while not binding or only weakly binding to the same antigens in other parts of the body in order to reduce side effects.

Such conditionally active biologic proteins may be conditionally active antibodies. In some embodiments, the present invention also provides conditionally active biologic proteins that are proteins other than antibodies. For example, a conditionally active immune regulator may be developed by the present invention for preferentially regulating the immune response in the synovial fluid, which may less or no effect on the immune response at other parts of the body.

The conditionally active biologic proteins may be conditionally active suppressors of cytokine signaling (SOCS). Many of these SOCS are involved in inhibiting the JAK-STAT signaling pathway. The conditionally active suppressors of cytokine signaling can preferentially suppress the cytokine signaling in the synovial fluid, while not or to a lesser extent suppressing the cytokine signaling in other parts of the body.

In some embodiments, the present invention provides a conditionally active biologic protein derived from a wild-type biologic protein. The conditionally active biologic protein has a lower activity under at least one physiological condition in certain parts of the body such as in blood plasma than the wild-type biologic protein, and has a higher activity than the wild-type biologic protein under at least one physiological condition in the synovial fluid. Such conditionally active biologic proteins can preferentially function in the synovial fluid, but not or to a lesser extent act upon other parts of the body. Consequently, such conditionally active biologic proteins may have reduced side effects.

In some embodiments, the conditionally active biologic proteins are antibodies against an antigen in or exposed to synovial fluid. Such antigens may be any proteins involved in immune response/inflammation in a joint disease, though the antigen is often a cytokine. The conditionally active antibody has a lower affinity to the antigen than the wild-type antibody for the same antigen under at least one physiological condition in other parts of the body (such as blood plasma), while has higher affinity for the antigen than the wild-type antibody under at least one physiological condition of synovial fluid. Such conditionally active antibodies can bind weakly or not at all to the antigen in other parts of the body, but bind, for example bind strongly and tightly or bind stronger to the antigen in synovial fluid.

Engineering Conditionally Active Biologic Proteins for Tumors

Cancer cells in a solid tumor are able to form a tumor microenvironment in their surroundings to support the growth and metastasis of the cancer cells. A tumor microenvironment is the cellular environment in which the tumor exists, including surrounding blood vessels, immune cells, fibroblasts, other cells, soluble factors, signaling molecules, an extracellular matrix, and mechanical cues that can promote neoplastic transformation, support tumor growth and invasion, protect the tumor from host immunity, foster therapeutic resistance, and provide niches for dormant metastases to thrive. The tumor and its surrounding microenvironment are closely related and interact constantly. Tumors can influence their microenvironment by releasing extracellular signals, promoting tumor angiogenesis and inducing peripheral immune tolerance, while the immune cells in the microenvironment can affect the growth and evolution of cancerous cells. See Swarts et al. "Tumor Microenvironment Complexity: Emerging Roles in Cancer Therapy," Cancer Res, vol., 72, pages 2473-2480, 2012.

The tumor microenvironment is often hypoxic. As the tumor mass increases, the interior of the tumor grows farther away from existing blood supply, which leads to difficulties in fully supplying oxygen to the tumor microenvironment. The partial oxygen pressure in the tumor environment is below 5 mm Hg in more than 50% of locally advanced solid tumors, in comparison with a partial oxygen pressure at about 40 mm Hg in blood plasma. In contrast, other parts of the body are not hypoxic. The hypoxic environment leads to genetic instability, which is associated with cancer progression, via downregulating nucleotide excision repair and mismatch repair pathways. Hypoxia also causes the upregulation of hypoxia-inducible factor 1 alpha (HIF1-α), which induces angiogenesis, and is associated with poorer prognosis and the activation of genes associated with metastasis. See Weber et al., "The tumor microenvironment," *Surgical Oncology*, vol. 21, pages 172-177, 2012 and Blagosklonny, "Antiangiogenic therapy and tumor progression," *Cancer Cell*, vol. 5, pages 13-17, 2004.

In addition, tumor cells tend to rely on energy generated from lactic acid fermentation, which does not require oxygen. So tumor cells are less likely to use normal aerobic respiration that does require oxygen. A consequence of using lactic acid fermentation is that the tumor microenvironment is acidic (pH 6.5-6.9), in contrast to other parts of the body which are typically either neutral or slightly basic. For example, human blood plasma has a pH of about 7.4. See Estrella et al., "Acidity Generated by the Tumor Microenvironment Drives Local Invasion," *Cancer Research*, vol. 73, pages 1524-1535, 2013. The nutrient availability in the tumor microenvironment is also low due to the relatively high nutrient demand of the proliferating cancer cells, in comparison with cells located in other parts of the body.

Further, the tumor microenvironment also contains many distinct cell types not commonly found in other parts of the body. These cell types include endothelial cells and their precursors, pericytes, smooth muscle cells, Wbroblasts, carcinoma-associated Wbroblasts, myoWbroblasts, neutrophils, eosinophils, basophils, mast cells, T and B lymphocytes, natural killer cells and antigen presenting cells (APC) such as macrophages and dendritic cells (Lorusso et al., "The tumor microenvironment and its contribution to tumor evolution toward metastasis," *Histochem Cell Biol*, vol. 130, pages 1091-1103, 2008).

Accordingly, the tumor microenvironment has at least several physiological conditions that are different from those of other parts of body, such as the physiological conditions in blood plasma. The tumor microenvironment has a pH (acidic) that is lower than other parts of the body, especially the blood plasma (pH 7.4). The tumor microenvironment has a lower concentration of oxygen than other parts of the body, such as blood plasma. Also, the tumor microenvironment has a lower nutrient availability than other parts of the body, especially the blood plasma. The tumor microenvironment also has some distinct cell types that are not commonly found in other parts of the body, especially the blood plasma.

Some cancer drugs include antibodies that can penetrate into the tumor microenvironment and act upon the cancer cells therein. Antibody-based therapy for cancer is well established and has become one of the most successful and important strategies for treating patients with haematological malignancies and solid tumors. There is a broad array of cell surface antigens that are expressed by human cancer cells that are overexpressed, mutated or selectively expressed in cancer cells compared with normal tissues. These cell surface antigens are excellent targets for antibody cancer therapy.

Cancer cell surface antigens that may be targeted by antibodies fall into several different categories. Haematopoietic differentiation antigens are glycoproteins that are usually associated with clusters of differentiation (CD) groupings and include CD20, CD30, CD33 and CD52. Cell surface differentiation antigens are a diverse group of glycoproteins and carbohydrates that are found on the surface of both normal and tumor cells. Antigens that are involved in growth and differentiation signaling are often growth factors and growth factor receptors. Growth factors that are targets for antibodies in cancer patients include CEA2, epidermal growth factor receptor (EGFR; also known as ERBB1)12, ERBB2 (also known as HER2)13, ERBB3 (REF. 18), MET (also known as HGFR)19, insulin-like growth factor 1 receptor (IGF1R)20, ephrin receptor A3 (EPHA3)21, tumor necrosis factor (TNF)-related apoptosis-inducing ligand receptor 1 (TRAILR1; also known as TNFRSF10A), TRAILR2 (also known as TNFRSF10B) and receptor activator of nuclear factor-κB ligand (RANKL; also known as TNFSF11)22. Antigens involved in angiogenesis are usually proteins or growth factors that support the formation of new microvasculature, including vascular endothelial growth factor (VEGF), VEGF receptor (VEGFR), integrin $\alpha V\beta 3$ and integrin $\alpha 5\beta 1$ (REF. 10). Tumor stroma and the extracellular matrix are indispensable support structures for a tumor. Stromal and extracellular matrix antigens that are therapeutic targets include fibroblast activation protein (FAP) and tenascin. See Scott et al., "Antibody therapy of cancer," *Nature Reviews Cancer*, vol. 12, pages 278-287, 2012.

In addition to antibodies, other biologic proteins have also shown promise in treating cancers. Examples include tumor suppressors such as Retinoblastoma protein (pRb), p53, pVHL, APC, CD95, ST5, YPEL3, ST7, and ST14. Some proteins that induce apoptosis in cancer cells may also be introduced into tumors for shrinking the size of tumors. There are at least two mechanisms that can induce apoptosis in tumors: the tumor necrosis factor-induced mechanism and the Fas-Fas ligand-mediated mechanism. At least some of the proteins involved in either of the two apoptotic mechanisms may be introduced to tumors for treatment.

Cancer stem cells are cancer cells that have the ability to give rise to all cell types found in a particular cancer sample, and are therefore tumor-forming. They may generate tumors through the stem cell processes of self-renewal and differentiation into multiple cell types. It is believed that cancer stem cells persist in tumors as a distinct population and cause relapse and metastasis by giving rise to new tumors. Development of specific therapies targeted at cancer stem cells may improve the survival and quality of life of cancer patients, especially for sufferers of metastatic disease.

These drugs for treating tumors often interfere with normal physiological functions in other parts of the body besides tumors. For example, proteins inducing apoptosis in tumors may also induce apoptosis in some other parts of the body thus causing side effects. In embodiments where an antibody is used to treat tumors, the antigen of the antibody may also be expressed in other parts of the body where they perform normal physiological functions. For example, monoclonal antibody bevacizumab (targeting vascular endothelial growth factor) to stop tumor blood vessel growth. This antibody can also prevent blood vessel growth or repair in other parts of the body, thus causing bleeding, poor wound healing, blood clots, and kidney damage. Development of a conditionally active biologic protein that concentrates on targeting mainly or solely tumors is highly desirable for more effective tumor therapies.

In some embodiments, the present invention provides a conditionally active biologic protein generated from a wild-type biologic protein that may be a candidate for tumor treatment. The conditionally active biologic protein has lower activity under at least one physiological condition in parts of the body other than the tumor microenvironment such as blood plasma than the wild-type biologic protein, while it has higher activity under at least one physiological condition in the tumor microenvironment than the wild-type biologic protein. Such conditionally active biologic proteins can preferentially act upon cancer cells in the tumor microenvironment for treating tumors, and thus will be less likely to cause side effects. In the embodiment where the biologic protein is an antibody against an antigen on the surface of the tumor cells where the antigen is exposed to the tumor microenvironment, the conditionally active antibody has lower affinity to the antigen than the wild-type antibody in other parts of the body, e.g. a non-tumor microenvironment, while it has higher affinity to the antigen than the wild-type antibody in the tumor microenvironment. Such conditionally active antibodies can bind weakly or not at all to the antigen in other parts of the body, but have greater binding, or bind strongly and tightly, to the antigen in the tumor microenvironment.

In some embodiments, the conditionally active antibody is an antibody against an immune checkpoint protein, resulting in inhibition of the immune checkpoints. Such conditionally active antibodies have at least one of (1) an increased binding affinity to the immune checkpoint protein in a tumor microenvironment in comparison to the wild-type antibody from which the conditionally active antibody is derived, and, (2) a decreased binding affinity to the immune checkpoint protein in a non-tumor microenvironment in comparison to the wild-type antibody from which the conditionally active antibody is derived.

The immune checkpoints function as endogenous inhibitory pathways for the immune system to maintain self-tolerance and modulate the duration and extent of immune response to antigenic stimulation, i.e., foreign molecules, cells and tissues See Pardoll, Nature Reviews Cancer, vol. 12, pages 252-264, 2012. Inhibition of immune checkpoints by suppressing one or more checkpoint proteins can cause super-activation of the immune system, especially T-cells, thus inducing the immune system to attack tumors. Checkpoint proteins suitable for the present invention include CTLA4 and its ligands CD80 and CD86, PD1 and its ligands PDL1 and PDL2, T cell immunoglobulin and mucin protein-3 (TIM3) and its ligand GAL9, B and T lymphocyte attenuator (BTLA) and its ligand HVEM (herpesvirus entry mediator), receptors such as killer cell immunoglobulin-like receptor (KIR), lymphocyte activation gene-3 (LAG3) and adenosine A2a receptor (A2aR), as well as ligands B7-H3 and B7-H4. Additional suitable immune checkpoint proteins are described in Pardoll, Nature Reviews Cancer, vol. 12, pages 252-264, 2012 and Nirschl & Drake, Clin Cancer Res, vol. 19, pages 4917-4924, 2013, the disclosures of which are hereby incorporated herein by reference.

CTLA-4 and PD1 are two of the best known immune checkpoint proteins. CTLA-4 can down-regulate pathways of T-cell activation (Fong et al., Cancer Res. 69(2):609-615, 2009; and Weber, Cancer Immunol. Immunother, 58:823-830, 2009). Blockading CTLA-4 has been shown to augment T-cell activation and proliferation. Inhibitors of CTLA-4 include anti-CTLA-4 antibodies. Anti-CTLA-4 antibodies bind to CTLA-4 and block the interaction of CTLA-4 with its ligands CD80 or CD86 thereby blocking the down-regulation of the immune responses elicited by the interaction of CTLA-4 with its ligand.

The checkpoint protein PD1 is known to suppress the activity of T cells in peripheral tissues at the time of an inflammatory response to infection and to limit autoimmunity. An in vitro PD1 blockade can enhance T-cell proliferation and cytokine production in response to stimulation by specific antigen targets or by allogeneic cells in mixed lymphocyte reactions. A strong correlation between PD1 expression and reduced immune response was shown to be caused by the inhibitory function of PD1, i.e., by inducing immune checkpoints (Pardoll, Nature Reviews Cancer, 12: 252-264, 2012). A PD1 blockade can be accomplished by a variety of mechanisms including antibodies that bind PD1 or its ligands, PDL1 or PDL2.

Past research has discovered antibodies against several checkpoint proteins (CTLA4, PD1, PD-L1). These antibodies are effective in treating tumors by inhibiting the immune checkpoints thereby super-activating the immune system, especially the T-cells, for attacking tumors (Pardoll, Nature Reviews Cancer, vol. 12, pages 252-264, 2012). However, the super-activated T-cells may also attack host cells and/or tissues, resulting in collateral damage to a patient's body. Thus, therapy based on use of these known antibodies for inhibition of immune checkpoints is difficult to manage and the risk to the patient is a serious concern. For example, an FDA approved antibody against CTLA-4 carries a black box warning due to its high toxicity.

The present invention addresses the problem of collateral damage by super-activated T-cells by providing conditionally active antibodies against immune checkpoint proteins. These conditionally active antibodies preferentially activate the immune checkpoints in a tumor-microenvironment. At the same time, the immune checkpoints in the non-tumor-microenvironment(s), e.g. normal body tissue, are not inhibited or are less inhibited by the conditionally active antibodies such that in the non-tumor microenvironment the potential for collateral damage to the body is reduced. This goal is achieved by engineering the conditionally active antibod to be more active in the tumor microenvironment than in the non-tumor microenvironment.

In some embodiments, the conditionally active antibody against an immune checkpoint protein may have a ratio of binding activity to an immune checkpoint protein in the tumor-microenvironment to the binding activity to the same immune checkpoint protein in a non-tumor microenvironment of at least about 1.1, or at least about 1.2, or at least about 1.4, or at least about 1.6, or at least about 1.8, or at least about 2, or at least about 2.5, or at least about 3, or at least about 5, or at least about 7, or at least about 8, or at least about 9, or at least about 10, or at least about 15, or at least about 20. A typical assay for measuring the binding activity of an antibody is an ELISA assay.

Highly immunogenic tumors, such as malignant melanoma, are most vulnerable to a super-activated immune system achieved by immune system manipulation. Thus the conditionally active antibodies against immune checkpoint proteins may be especially effective for treating such highly immunogenic tumors. However, other types of tumors are also vulnerable to a super-activated immune system.

In some embodiments, the conditionally active antibodies against the immune checkpoint proteins may be used in combination therapy. For example, combination therapy may include a conditionally active antibody against a tumor cell surface molecule (tumor specific antigen) and a conditionally active antibody against an immune checkpoint protein. In one embodiment, both the binding activity of the conditionally active antibody to the tumor cell surface molecule and the binding activity of the conditionally active antibody to the immune checkpoint protein may reside in a single protein, i.e., a bispecific conditionally active antibody as disclosed herein. In some further embodiments, combination therapy may include a conditionally active antibody against a tumor cell surface molecule (tumor specific antigen) and two or more conditionally active antibodies against two or more edifferent immune checkpoint proteins. In one embodiment, all of these binding activities may reside in a single protein, i.e., a multispecific antibody as disclosed herein.

Since the conditionally active antibodies are more active in a tumor microenvironment in comparison with the activity of the wild-type antibody against the same tumor cell surface molecule or checkpoint protein from which the conditionally active antibody is derived, these combination therapies can provide both an enhanced efficacy and a significant reduction in toxicity. The reduced toxicity of these conditionally active antibodies, especially the antibodies against the immune checkpoint proteins, can allow safe use of potent antibodies, such as ADC antibodies as described herein, as well as a higher dose of the antibodies.

In some embodiments, the conditionally active antibodies against the checkpoint proteins may be in a prodrug form. For example, the conditionally active antibodies may be prodrugs that have no desired drug activity before being cleaved and turned into a drug form. The prodrugs may be cleaved preferentially in a tumor-microenvironment, either because the enzyme that catalyzes such cleavage exists preferentially in the tumor-microenvironment or because the conditionally active antibodies make the cleavage site more accessible in a tumor microenvironment, in comparison with the accessibility of the cleavage site in a non-tumor microenvironment.

Engineering Conditionally Active Biologic Proteins for Stem Cell Niches, Including Tumor Stem Cells Stem cells exist in an environment called stem cell niche in the body, which constitutes a basic unit of tissue physiology, integrating signals that mediate the response of stem cells to the needs of organisms. Yet the niche may also induce pathologies by imposing aberrant functions on stem cells or other targets. The interplay between stem cells and their niches creates the dynamic system necessary for sustaining tissues, and for the ultimate design of stem-cell therapeutics (Scadden, "The stem-cell niche as an entity of action," Nature, vol. 441, pages 1075-1079, 2006). Common stem cell niches in vertebrates include the germline stem cell niche, the hematopoietic stem cell niche, the hair follicle stem cell niche, the intestinal stem cell niche, and the cardiovascular stem cell niche.

The stem cell niche is a specialized environment that is different from other parts of the body (e.g. blood plasma) (Drummond-Barbosa, "Stem Cells, Their Niches and the Systemic Environment: An Aging Network," Genetics, vol. 180, pages 1787-1797, 2008; Fuchs, "Socializing with the Neighbors: Stem Cells and Their Niche," Cell, vol. 116, pages 769-778, 2004). The stem cell niche is hypoxic where oxidative DNA damage is reduced. Direct measurements of oxygen levels have revealed that bone marrow is, in general, quite hypoxic (~1%-2% O2), in comparison to blood plasma (Keith et al., "Hypoxia-Inducible Factors, Stem Cells, and Cancer," Cell, vol. 129, pages 465-472, 2007; Mohyeldin et al., "Oxygen in Stem Cell Biology: A Critical Component of the Stem Cell Niche," Cell Stem Cell, vol. 7, pages 150-161, 2010). In addition, the stem cell niches need to have several other factors to regulate stem cell characteristics within the niches: extracellular matrix components, growth factors, cytokines, and factors of the physiochemical nature of the environment including the pH, ionic strength (e.g. $Ca^{2+}$ concentration) and metabolites.

Accordingly, the stem cell niche has at least several physiological conditions that are different from those of the other parts of body, such as the physiological conditions in the blood plasma. The stem cell niche has a lower oxygen concentration (1-2%) than other parts of the body, especially the blood plasma. Other physiological conditions for the stem cell niche including pH and ionic strength, may also be different from other parts of the body.

Stem cell therapy is an interventional strategy that introduces new adult stem cells into damaged tissue in order to treat disease or injury. This strategy depends on the ability of stem cells to self-renew and give rise to subsequent offspring with variable degrees of differentiation capacities. Stem cell therapy offers significant potential for regeneration of tissues that can potentially replace diseased and damaged areas in the body, with minimal risk of rejection and side effects. Therefore, delivering a drug (biologic protein (e.g. antibody) or chemical compound) to the stem cell niche for influencing the renewal and differentiation of stem cells is an important part of stem cell therapy.

There are several examples on how the stem cell niches influence the renewal and/or differentiation of the stem cells in mammals. The first is in the skin, where the 0-1 integrin is known to be differentially expressed on primitive cells and to participate in constrained localization of a stem-cell population through interaction with matrix glycoprotein ligands. Second, in the nervous system, the absence of tenascin C alters neural stem-cell number and function in the subventricular zone. Tenascin C seems to modulate stem-cell sensitivity to fibroblast growth factor 2 (FGF2) and bone morphogenetic protein 4 (BMP4), resulting in increased stem-cell propensity. Third, another matrix protein, the Arg-Gly-Asp-containing sialoprotein, osteopontin (OPN), has now been demonstrated to contribute to haematopoietic stem cell regulation. OPN interacts with several receptors known to be on haematopoietic stem cells, CD44, and α4 and α5β1 integrins. OPN production can vary markedly, particularly with osteoblast activation. Animals deficient in OPN have an increased HS-cell number, because a lack of OPN leads to superphysiologic stem-cell expansion under stimulatory conditions. Therefore, OPN seems to serve as a constraint on haematopoietic stem cell numbers, limiting the number of stem cells under homeostatic conditions or with stimulation. See Scadden, "The stem-cell niche as an entity of action," Nature, vol. 441, pages 1075-1079, 2006.

Xie et al. "Autocrine signaling based selection of combinatorial antibodies that transdifferentiate human stem cells," *Proc Natl Acad Sci USA*, vol. 110, pages 8099-8104, 2013) discloses a method of using antibodies to influence stem cell differentiation. The antibodies are agonists for a granulocyte colony stimulating factor receptor. Unlike the natural granulocyte-colony stimulating factor that activates cells to differentiate along a predetermined pathway, the isolated agonist antibodies transdifferentiated human myeloid lineage CD34+ bone marrow cells into neural progenitors. Melidoni et al. ("Selecting antagonistic antibodies that control differentiation through inducible expression in embryonic stem cells," *Proc Natl Acad Sci USA*, vol. 110, pages 17802-17807, 2013) also discloses a method of using an antibody to interfere the interaction between FGF4 and its receptor FGFR1β, therefore block the autocrine FGF4-mediated embryonic stem cell differentiation.

Knowledge of the functions of ligands/receptors in stem cell differentiation has enabled the strategy of applying biologic proteins to interfere with these ligands/receptors for the purpose of regulating or even directing stem cell differentiation. The ability to control differentiation of genetically unmodified human stem cells through the administration of antibodies into the stem cell niche can provide new ex vivo or in vivo approaches to stem cell-based therapeutics. In some embodiments, the present invention provides a conditionally active biologic protein generated from a wild-type biologic protein that is capable of entering the stem cell niches, including cancer stem cells, to regulate stem cell or tumor development. The conditionally active biologic protein has lower activity than the wild-type biologic protein under at least one physiological condition in other parts of the body, while it has higher activity than the wild-type biologic protein under at least one physiological condition in the stem cell niche, for example the cancer stem cell environment. Such conditionally active biologic proteins will be less likely to cause side effects and preferentially act in the stem cell niche to regulate renewal and differentiation of stem cells. In some embodiments, the conditionally active biologic proteins are antibodies. Such conditionally active antibodies can bind weakly or not at all to their antigens in other parts of the body, but bind strongly and tightly to the antigens in the stem cell niche.

The conditionally active proteins for the synovial fluid, tumor microenvironment and stem cell niches of the present invention are generated by a method for evolving a DNA that encodes a wild-type biologic protein to create a mutant DNA library. The mutant DNA library is then expressed to obtain mutant proteins. The mutant proteins are screened for a conditionally active biologic protein that has a higher activity than the wild-type biologic protein under at least one physiological condition of a first part of the body selected from the group consisting of synovial fluid, tumor microenvironment, and stem cell niches, and has lower activity than the wild-type biologic protein under at least one physiological condition at a second part of the body that is different from the first part of the body. The second part of the body may be the blood plasma. Such selected mutant biologic proteins are conditionally active biologic proteins that have high activity in the first part of the body but low activity in the second part of the body.

Such conditionally active biologic proteins are advantageous in lowering side effects of the wild-type protein, since the conditionally active biologic protein has lower activity in the other parts of the body where the conditionally active biologic protein is not intended to act. For instance, if the conditionally active biologic protein is intended to be introduced into the tumor microenvironment, the fact that the conditionally active biologic protein has low activity in parts of the body other than the tumor microenvironment means such conditionally active biologic protein will be less likely to interfere with normal physiological functions in parts of the body other than the tumor microenvironment. At the same time, the conditionally active biologic protein has high activity in the tumor microenvironment, which gives the conditionally active biologic protein a higher efficacy in treating tumors.

Because of the reduced side effects, the conditionally active biologic protein will allow a significantly higher dose of the protein to be safely used, in comparison with the wild-type biologic protein. This is especially beneficial for an antibody against a cytokine or a growth factor, because antibodies against the cytokine or growth factor may interfere with normal physiological functions of the cytokine or growth factor in other parts of the body. By using a conditionally active biologic protein, with reduced side effects, higher doses may be used to achieve higher efficacy.

The conditionally active biologic proteins for acting in one of a synovial fluid, tumor microenvironment, or stem cell niche can also enable new drug targets to be used. Using traditional biologic proteins as therapeutics may cause unacceptable side effects. For example, inhibition of an epidermal growth factor receptor (EGFR) can very effectively suppress tumor growth. However, a drug inhibiting EGFR will also suppress growth at the skin and gastrointestinal (GI) tract. The side effects render EGFR unsuitable as a tumor drug target. Using a conditionally active antibody that binds to EGFR at high affinity in only the tumor microenvironment, but not or at very low affinity at any other parts of the body, will significantly reduce the side effects and at the same time suppress tumor growth. In this case, EGFR may become an effective new tumor drug target by using conditionally active antibodies.

In another example, suppressing cytokines is often beneficial in repairing joint damage. However, suppressing cytokines in other parts of the body also may suppress the immune response of the body, causing an immune deficiency. Thus, cytokines in synovial fluid are not ideal targets for developing traditional antibody drugs for treatment of joint damage. However, by using conditionally active antibodies that preferentially bind to cytokines in the synovial fluid, while not or only weakly to the same cytokines in other parts of the body, the side effect of immune deficiency can be dramatically reduced. Therefore, cytokines in synovial fluid may become suitable targets for repairing joint damage by using conditionally active antibodies.

Engineering Viral Particles with a Conditionally Active Biologic Protein

Viral particles have long been used as delivery vehicles for transporting proteins, nucleic acid molecules, chemical compounds or radioactive isotopes to a target cell or tissue. Viral particles that are commonly used as delivery vehicles include retroviruses, adenoviruses, lentivirus, herpes virus, and adeno-associated viruses. The viral particles recognize their target cells through a surface protein that serves as a recognition protein for specific binding to a cellular protein that serves as target protein of the target cells, often in a ligand-receptor binding system (Lentz, "The recognition event between virus and host cell receptor: a target for antiviral agents," *J. of Gen. Virol*., vol. 71, pages 751-765, 1990, incorporated herein by reference). For example, the viral recognition protein may be a ligand for a receptor on the target cells. The specificity between a ligand and a receptor allows the viral particles to specifically recognize and deliver their content to a target cell.

Techniques for developing artificial viral particles from wild-type viruses are well known to a person skilled in the art. Known artificial viral particles as delivery vehicles include these based on retroviruses (see, e.g., WO 90/07936; WO 94/03622; WO 93/25698; WO 93/25234; U.S. Pat. No. 5,219,740; WO 93/11230: WO 93/10218; U.S. Pat. No. 4,777,127; GB Patent No. 2,200,651; EP 0 345 242; and WO 91/02805), alphavirus (e.g., Sindbis virus vectors, Semliki forest virus (ATCC VR-67; ATCC VR-1247), Ross River virus (ATCC VR-373; ATCC VR-1246), Venezuelan equine encephalitis virus (ATCC VR-923; ATCC VR—1250; ATCC VR 124.9; ATCC VR-532)), and adeno-associated viruses (see, e.g., WO 94/12649, WO 93/03769; WO 93/19191; WO 94/28938: WO 95/11984 and WO 95/00655).

Generally, the artificial viral particles are constructed by inserting a foreign recognition protein into a virus particle, often replacing the native recognition protein by recombinant technology. The foreign recognition protein may be, for example, an antibody, a receptor, a ligand or a collagen binding domain. The present invention provides a conditionally active recognition protein that is inactive or less active for binding to a cell at a normal physiological condition, and that is active or more active for binding to a cell at an aberrant condition. The conditionally active recognition protein can thereby preferentially bind to target cells of diseased tissue and/or at a disease site based on the presence of an abnormal condition at that site and avoid or only minimally bind to the cells of normal tissue where a normal physiological condition exists. The conditionally active recognition protein may be expressed and displayed on the surface of a viral particle.

In some embodiments, the present invention provides a method of evolving a wild-type recognition protein and screening for a conditionally active recognition protein. The conditionally active recognition protein is less active in binding to a cell than the wild-type recognition protein under a normal physiological condition, and more active in binding to a cell than the wild-type recognition protein under an aberrant condition. Such a conditionally active recognition protein may be inserted into a viral particle by well-known recombinant technology to generate a conditionally active viral particle.

In another embodiment, the present invention provides a conditionally active viral particle comprising a conditionally active recognition protein, which allows the conditionally active viral particle to recognize and bind with the target cells of diseased tissue or at a disease site, but not the cells of normal tissue. Such a conditionally active viral particle can preferentially deliver therapeutics within the viral particle to the disease tissue or disease site, while the conditionally active viral particle delivers less or does not deliver the therapeutics to the cells of normal tissue.

In some embodiments, the target cells at a disease site are inside a zone or microenvironment with an abnormal pH (e.g., pH 6.5) or an abnormal temperature, in comparison with the pH or temperature in other parts of the body that are healthy or not suffering from the particular disease or disease state. In this embodiment, the conditionally active recognition protein is less active than a wild-type recognition protein in binding with a target protein of a target cell at a normal physiological pH or temperature, and more active than a wild-type recognition protein in binding with the target protein of a target cell at an abnormal pH or temperature. In this manner, the recognition protein will preferentially bind at a site where an abnormal pH or temperature is encountered thereby delivering a treatment to the site of a disease.

In one embodiment, the viral particle may comprise a conditionally active antibody of the present invention, and especially the variable region of an antibody (e.g., Fab, Fab', Fv). Such a conditionally active antibody can bind to the target protein (as antigen) of a target cell with lower affinity than a wild-type antibody under a normal physiological condition which may be encountered at a location with normal tissue, and a higher affinity than the wild-type antibody under aberrant condition which may be encountered at a disease site or diseased tissue. The conditionally active antibody may be derived from the wild-type antibody according to the method of the present invention.

In an embodiment, the target protein on the target cell includes tyrosine kinase growth factor receptors which are overexpressed on the cell surfaces in, for example, many tumors. Exemplary tyrosine kinase growth factors are VEGF receptors, FGF receptors, PDGF receptors. IGF receptors, EGF receptors. TGF—alpha receptors. TGF-beta receptors, HB-EGF receptors, ErbB2 receptors, ErbB3 receptors, and ErbB4 receptors.

Engineering Conditionally Active DNA/RNA Modifying Proteins

DNA/RNA modifying proteins have been discovered as a form of new genome-engineering tools, particularly one called CRISPR, which can allow researchers to perform microsurgery on genes, precisely and easily changing a DNA sequence at exact locations on a chromosome (genome editing, Mali et al., "Cas9 as a versatile tool for engineering biology," *Nature Methods*, vol. 10, pages 957-963, 2013). For example, sickle-cell anemia is caused by a single base mutation, which can potentially be corrected using DNA/RNA modifying proteins. The technology may precisely delete or edit bits of a chromosome, even by changing a single base pair (Makarova et al., "Evolution and classification of the CRISPR-Cas systems," *Nature Reviews Microbiology*, vol. 9, pages 467-477, 2011).

Genome editing with CRISPR has the ability to quickly and simultaneously make multiple genetic changes to a cell. Many human illnesses, including heart disease, diabetes, and neurological diseases, are affected by mutations in multiple genes. This CRISPR-based technology has the potential to reverse the disease causing mutations and cure these diseases or at least reduce the severity of these diseases. Genome editing relies on CRISPR associated (Cas) proteins (a family of enzymes) for cutting the genomic DNA. Typically, the Cas protein is guided by a small guide RNA to a targeted region in the genome, where the guide RNA matches the target region. Because the Cas protein has little or no sequence specificity, the guide RNA serves as a pointer for the Cas protein to achieve precise genome editing. In one embodiment, one Cas protein may be used with multiple guide RNAs to simultaneously correct multiple gene mutations.

There are many Cas proteins. Examples include Cas1, Cas2, Cas3', Cas3", Cas4, Cas5, Cas6, Cas6e, Cas6f, Cas7, Cas8a1, Cas8a2, Cas8b, Cas8c, Cas9, Cas10, Cas10d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 ((Makarova et al., "Evolution and classification of the CRISPR-Cas systems," *Nature Reviews Microbiology*, vol. 9, pages 467-477, 2011).

To conduct genome editing, the Cas protein has to enter the target cell. Cells in a subject may have a different intracellular pH inside of the cells. Some cells in diseased tissue have an abnormal intracellular pH. For example, some tumor cells tend to have an alkaline intracellular pH of about 7.12-7.65, while cells in normal tissue have a neutral intracellular pH ranging from 6.99-7.20. See Cardone et al., "The role of disturbed pH dynamics and the Na(+)/H(+) exchanger in metatasis," *Nat. Rev. Cancer*, vol. 5, pages 786-795, 2005. In chronic hypoxia, the cells in diseased tissue have an intracellular pH of about 7.2-7.5, also higher than the intracellular pH of normal tissue (Rios et al., "Chronic hypoxia elevates intracellular pH and activates Na+/H+ exchange in pulmonary arterial smooth muscle cells," *American Journal of Physiology—Lung Cellular and Molecular Physiology*, vol. 289, pages L867-L874, 2005). Further, in ischemia cells, the intracellular pH is typical in a range of 6.55-6.65, which is lower than the intracellular pH of normal tissue (Haqberg, "Intracellular pH during ischemia in skeletal muscle: relationship to membrane potential, extracellular pH, tissue lactic acid and ATP," *Pflugers Arch.*, vol. 404, pages 342-347, 1985). More examples of abnormal intracellular pH in diseased tissue are discussed in I-Ian et al., "Fluorescent Indicators for Intracellular pH," *Chem Rev.*, vol. 110, pages 2709-2728, 2010.

The present invention provides a method for producing a conditionally active Cas protein from a wild-type Cas protein, where the conditionally active Cas protein has at least one of (1) a decreased enzymatic activity relative to the activity of the wild-type Cas protein under a normal physiological condition inside a normal cell, and (2) an increased enzymatic activity relative to the activity of the wild-type Cas protein under an aberrant condition inside a target cell such as one of the diseased cells discussed above. In some embodiments, the normal physiological condition is an intracellular pH about neutral, and the aberrant condition is a different intracellular pH that is above or below neutral. In an embodiment, the aberrant condition is an intracellular pH of from 7.2 to 7.65 or an intracellular pH of from 6.5-6.8.

In some embodiments, the conditionally active Cas protein may be delivered to a target cell using the conditionally active viral particle of the present invention. The conditionally active viral particle comprises the conditionally active Cas protein and at least one guide RNA for directing the Cas protein to the location at which Cas protein will edit the genomic DNA.

Engineering the Fc Region of Conditionally Active Antibodies

The fragment crystallizable region (Fc region) is the tail region of an antibody that interacts with cell surface receptors called Fc receptors and some proteins of the complement system. Unlike the Fab region that is specific for each antigen, the Fc region of all antibodies in a class is the same for each species regardless which antigen the antibody binds.

The Fc receptors are members of the immunoglobulin gene superfamily of proteins. Fc receptors are found on a number of cells in the immune system including phagocytes like macrophages and monocytes, granulocytes like neutrophils and eosinophils, and lymphocytes of the innate immune system (natural killer cells) or adaptive immune system (e.g., B cells). After binding with an antibody, the Fc receptor activates these cells and allows these cells to identify and eliminate antigens (such as microbial pathogen) that are bound on the Fab region of the antibody. The Fc receptor mediated killing mechanisms include complement-dependent cytotoxicity (CDC), antibody-dependent cellular cytotoxicity (ADCC), and antibody-dependent cellular phagocytosis (ADCP).

In some embodiments, the Fc region is engineered to introduce mutations such as amino acid substitutions in the Fc region. Such substitution in the Fc region may increase the half-life of the mutated antibody in serum. For example, the half-life of an IgG antibody is correlated with its pH-dependent binding to the neonatal receptor FcRn, which is expressed on the surface of endothelial cells and protects the IgG in a pH-dependent manner from degradation. Several amino acid substitutions at the Fc region, such as T250Q/M428L and M252Y/S254T/T256E+H433K/N434F, have shown increased binding affinity of the antibody to FcRn and may be used to extend the half-life of the antibody.

Amino acid substitutions may also be introduced to the Fc region to alter effector functions. For example, human antibodies in the IgG class bind to Fcγ receptors (FcγRI, FcγRIIa, FcγRIIIa), the inhibitory FcγRIIb receptor, and the first component of the complement (C1q) with different affinities, yielding very different effector functions among different ones of these antibodies. Binding of IgG antibody to FcγRs or C1q depends on residues located in the hinge domain and the CH2 domain of the antibody. Amino acid substitutions in human antibodies IgG1 of IgG2 residues at positions 233-236 and antibody IgG4 residues at positions 327, 330 and 331 can greatly reduce ADCC and CDC. Furthermore, Alanine substitution at different positions in the Fc region, including K322, significantly reduced complement activation. Many more examples of engineering the Fc region are described in U.S. Pat. No. 8,362,210, which is incorporated by reference in its entirety.

In some embodiments, the Fc region of an antibody may be engineered to be capable of recognizing an antigen (US 2010/0256340, incorporated herein by reference). At least one, preferably two, extra Fab fragments may be linked onto the Fc region of an antibody. In some embodiments, the extra Fab fragments are conditionally active. For example, the antibody of the present invention designed for crossing blood-brain barrier (BBB) may contain such an extra Fab fragment with a low affinity for a BBB-R on the plasma side and no affinity to the BBB-R on the brain side. The antibody can also bind to multiple brain antigens, and thus has higher selectivity for preferentially acting on sites where these antigens are present.

The present disclosure provides at least one composition comprising (a) a conditionally active biologic protein; and (b) a suitable carrier or diluent. The present disclosure also provides at least one composition comprising (a) a conditionally active biologic protein encoding nucleic acid as described herein; and (b) a suitable carrier or diluent. The carrier or diluent can optionally be pharmaceutically acceptable, according to known carriers or diluents. The composition can optionally further comprise at least one further compound, protein or composition.

The conditionally active biologic protein may be in the form of a pharmaceutically acceptable salt. Pharmaceutically acceptable salts means which can be generally used as salts of an therapeutic protein in pharmaceutical industry, including for example, salts of sodium, potassium, calcium and the like, and amine salts of procaine, dibenzylamine, ethylenediamine, ethanolamine, methylglucamine, taurine, and the like, as well as acid addition salts such as hydrochlorides, and basic amino acids and the like.

The present disclosure further provides at least one conditionally active biologic protein method or composition, for administering a therapeutically effective amount to modulate or treat at least one parent molecule related condition in a cell, tissue, organ, animal or patient and/or, prior to, subsequent to, or during a related condition, as known in the art and/or as described herein. Thus, the disclosure provides a method for diagnosing or treating a condition associated with the wild-type protein in a cell, tissue, organ or animal, comprising contacting or administering a composition comprising an effective amount of at least one conditionally active biologic protein of the disclosure with, or to, the cell, tissue, organ or animal. The method can optionally further comprise using an effective amount of 0.001-50 mg/kilogram of a conditionally active biologic protein of the disclosure to the cells, tissue, organ or animal. The method can optionally further comprise using the contacting or the administrating by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further comprise administering, prior, concurrently, or after the conditionally active biologic protein contacting or administering at least one composition comprising an effective amount of at least one compound or protein selected from at least one of a detectable label or reporter, a TNF antagonist, an antirheumatic, a muscle relaxant, a narcotic, a non-steroid anti-inflammatory drug (NSAK)), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, or an antiproliferative agent.

The present disclosure further provides at least one conditionally active biologic protein method for diagnosing at least one wild-type protein related condition in a cell, tissue, organ, animal or patient and/or, prior to, subsequent to, or during a related condition, as known in the art and/or as described herein.

Pharmaceutically acceptable carriers are determined in part by the particular composition being administered, as well as by the particular method used to administer the composition. Accordingly, there is a wide variety of suitable formulations of pharmaceutical compositions of the present invention. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of conditionally active biologic protein in these formulations can vary widely, and will be selected primarily based on fluid volumes, viscosities, body weight and the like in accordance with the particular mode of administration selected and the patient's needs.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Pharmaceutical compositions and formulations of the invention for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropyhnethyl cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscannellose sodium, talc, magnesium stearate, stearic acid, and other excipients, colorants, fillers, binders, diluents, buffering agents, moistening agents, preservatives, flavoring agents, dyes, disintegrating agents, and pharmaceutically acceptable carriers.

The invention provides aqueous suspensions comprising a conditionally active biologic protein, in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolality.

Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the conditionally active biologic protein, when administered orally, must be protected from digestion. This is typically accomplished either by complexing the conditionally active biologic protein with a composition to render it resistant to acidic and enzymatic hydrolysis or by packaging the conditionally active biologic protein in an appropriately resistant carrier such as a liposome. Means of protecting proteins from digestion are well known in the art. The pharmaceutical compositions can be encapsulated, e.g., in liposomes, or in a formulation that provides for slow release of the active ingredient.

The packaged conditionally active biologic protein, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like. Suitable formulations for rectal administration include, for example, suppositories, which consist of the packaged nucleic acid with a suppository base. Suitable suppository bases include natural or synthetic triglycerides or paraffin hydrocarbons, in addition, it is also possible to use gelatin rectal capsules which consist of a combination of the packaged nucleic acid with a base, including, for example, liquid triglycerides, polyethylene glycols, and paraffin hydrocarbons.

Dermal or topical delivery compositions of the invention may include in addition to a conditionally active biologic protein, a pharmaceutically acceptable carrier in a cream, ointment, solution or hydrogel formulation, and other compounds so long as the added component does not deleteriously affect delivery of the therapeutic protein. Conventional pharmaceutically acceptable emulsifiers, surfactants, suspending agents, antioxidants, osmotic enhancers, extenders, diluents and preservatives may also be added. Water soluble polymers can also be used as carriers.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives, in the practice of this invention, compositions can be administered, for example, by intravenous infusion, orally, topically, intraperitoneally, intravesically or intrathecally. In one aspect, parenteral modes of administration are preferred methods of administration for compositions comprising a conditionally active biologic protein. The compositions may conveniently be administered in unit dosage form and may be prepared by any of the methods well-known in the pharmaceutical art, for example as described in Remington's Pharmaceutical Sciences, Mack Publishing Co. Easton Pa., 18$^{th}$ Ed., 1990. Formulations for intravenous administration may contain a pharmaceutically acceptable carrier such as sterile water or saline, polyalkylene glycols such as polyethylene glycol, oils of vegetable origin, hydrogenated naphthalenes and the like. Also see and adapt the description in U.S. Pat. No. 4,318,905.

The formulations of packaged compositions comprising a conditionally active biologic protein can be presented in unit-dose or multi-dose sealed containers, such as ampoules and vials. Injection solutions and suspensions can be prepared from sterile powders, granules, and tablets of the kind previously described.

The present disclosure also provides at least one conditionally active biologic protein composition, device and/or method of delivery for diagnosing of at least one wild-type protein related condition, according to the present disclosure.

Also provided is a composition comprising at least one conditionally active biologic protein and at least one pharmaceutically acceptable carrier or diluent. The composition can optionally further comprise an effective amount of at least one compound or protein selected from at least one of a detectable label or reporter, a cytotoxic or other anti-cancer agent, an anti-metabolite such as methotrexate, an antiproliferative agent, a cytokine, or a cytokine antagonist, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog.

Also provided is a medical device, comprising at least one conditionally active biologic protein of the disclosure, wherein the device is suitable to contacting or administering the at least one conditionally active biologic protein by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In a further aspect, the disclosure provides a kit comprising at least one conditionally active biologic protein or fragment of the disclosure in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof in an aqueous diluent. In one aspect, in the kit, the concentration of conditionally active biologic protein or specified portion or variant in the first container is reconstituted to a concentration of about 0.1 mg/ml to about 500 mg/ml with the contents of the second container, in another aspect, the second container further comprises an isotonicity agent. In another aspect, the second container further comprises a physiologically acceptable buffer. In one aspect, the disclosure provides a method of treating at least one wild-type protein mediated condition, comprising administering to a patient in need thereof a formulation provided in a kit and reconstituted prior to administration.

Also provided is an article of manufacture for human pharmaceutical or diagnostic use, comprising packaging material and a container that includes a solution or a lyophilized form of at least one conditionally active biologic protein of the present disclosure. The article of manufacture can optionally comprise having the container as a component of a parenteral, subcutaneous, intramuscular, intravenous, intrartricular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The conditionally active biologic proteins of the present invention may also be used for brain diseases or other central nervous system disorders, as there exists a direct link between the immune system and central nervous system (Louveau et al., "Structural and functional features of central nervous system lymphatic vessels," Nature, vol. 523, pp. 337-341, 2015, hereby incorporated in its entirety by reference herein). The direct link consists of functional lymphatic vessels lining the dural sinuses. Through this direct link, conditionally active biologic proteins (especially conditionally active antibodies) may be able to access the central nervous system and acts on targets therein.

The present disclosure further provides any disclosure described herein. The following examples are illustrative, but not limiting, of the methods of the present disclosure. Other suitable modifications and adaptations of the variety of conditions and parameters normally encountered in the field, and which are obvious to those skilled in the art, are within the scope of this disclosure

EXAMPLES

Example 1: General Description of a Multiwall Assay (for Example, 96-Well Assay) for Temperature Mutants Fluorescent substrate is added to each well of a multiwall plate, at both wild-type and new, lower reaction temperatures (for example, either 37° C. or 25° C. as mentioned above) for an appropriate time period. Fluorescence is detected by measuring fluorescence in a fluorescent plate reader at appropriate excitation and emission spectra (for example, 320 nm exitation/405 nm emission). Relative fluorescence units (RFU) are determined. Supernatant from wild type molecule and plasmid/vector transformed cells are used as positive and negative controls. Duplicate reactions are performed for each sample, reaction temperature, and positive and negative control.

Mutants that are active at the lower temperature (for example, the mutants active at 25° C.) and that have a decrease in activity at the wild type temperature (for example, a 10%, 20%, 30%, 40% or more decrease in activity at 37° C.), thus having a ratio of activities greater than or equal to about 1.1 or more (e.g., the ratio of the activities at 25° C. or 37° C. (25° C./37° C.) is greater than or equal to 1.1 or more), can be deemed to be putative primary temperature sensitive hits. These putative primary temperature sensitive hits can then be rescreened, using the same assay, to confirm any primary hits.

Example 2: General Description of a Different Assay Format for Confirmation of Activity (for Example, a 14-mL Assay) for Temperature Mutants Mutants that are identified as temperature sensitive primary hits are expressed in 14 ml culture tubes and their enzymatic activity is measured at wild type (for example, 37° C.) and the lower temperature (for example, 25° C.). Protein is expressed and purified as described above for the multiwall format, with the exception that the expression is performed in different format (14 ml tubes) rather than the multiwall (96-well plate) format.

Each mutant supernatant is transferred to a multiwall plate, for example a 96-well microplate. Fluorescent substrate is added to each tube at the indicated reaction temperatures (wild-type, lower temperature) for a required period of time. Wild-type molecules are used as a positive control and supernatant from cells transformed with only vector is used as a negative control. Fluorescence is detected by measuring fluorescence in a fluorescent plate reader at the appropriate emission spectra (for example, 320 nm exitation/405 ran emission). Relative fluorescence units (RFU) are determined. Duplicate reactions can are performed for each sample, reaction temperature, and positive and negative control.

Mutants that are active at the lower temperatures (for example, 25° C.) but that demonstrate at least a 30% or more decreased activity at wild type (for example, 37° C.), thus have a ratio of activity at lower temperature (for example, 25° C.) to wild type temperature (for example, 37° C.) equal to or greater than 1.5, are identified as temperature sensitive hits.

The activities of mutants at the lower temperature (for example 25° C.) are compared to the activity of the wild-type molecule at the wild-type temperature (for example 37° C.). If molecules are more active than the wild-type molecules at the lower temperature (for example 25° C.), as indicated by a residual activity >1, preferably 2 or greater than 2, and if the mutants demonstrate an overall decrease in activity when compared to the wild-type molecule at the wild-type temperature (37° C.), the phenotype of the mutants as temperature sensitive mutants can be confirmed.

Example 3: General Description of Further Evolution of Hits Discovered

If desired, a new, combinatorial variant library is generated from all or selected mutant hits previously identified. The new library can be designed to contain every possible combination of amino acid variants for each of the selected mutants, and rescreened as described for new hits.

Example 4: General Description of Reversibility of Enzymatic Activity Following Decrease in Temperature Temperature sensitive, evolved mutants can be further assayed to determine whether enzymatic activity at lower temperatures (for example, 25° C.) is reversible or irreversible by exposing the mutants to elevated temperatures followed by a return to the lower temperature (for example, 25° C.). The temperature sensitive mutants are expressed in any desired format, for example in 14 ml culture tubes, as briefly described. The mutants are tested for their activities under several conditions, including the wild-type temperature (for example, 37° C.) as well as other temperatures, and subsequently re-exposure to the requisite lower temperature of (25° C. for example). Mutants that are active at lower temperatures, show decreased activity when raised to higher or wild-type temperatures (i.e., the ratio of the activities at lower to higher temperatures is equal to or greater than 1, 1.5, or 2 or higher), and exhibit a baseline activity when lowered again to the lower temperature are scored as "Reversible Hits". Mutants that are active at the lower temperature, show decreased activity when raised to higher or wild-type temperatures (i.e., the ratio of the activities at the lower to higher temperatures is equal to or greater than 1, 1.5 or 2 or higher), and exhibit at least the same amount of decreased activity when lowered again to the lower temperature are scored as "Irreversible Hits".

Example 5: Materials and Methods to Screen for Conditionally Active Angiostatin Variants Materials and methods to screen for conditionally active angiostatin variants can be adapted from Chi and Pizzo, "Angiosatin is directly cytotoxic to tumor cells at low extracellular pH: a mechanism dependent on cell surface-associated ATP synthase", *Cancer Res.* 2006; 66(2):875-882, which is incorporated herein by reference.

Materials.

Wild-type angiostatin kringles 1 to 3, derived from human plasminogen, can be obtained from Calbiochem (Darmstadt, Germany) and reconstituted in sterile PBS. Polyclonal antibodies directed against the catalytic beta-subunit of ATP synthase can be generated and bovine Fl ATP synthase subunit can be purified as previously described (Moser et al., "Angiostatin binds ATP synthase on the surface of human endothelial cells", *Proc Natl Acad Sci USA* 1999; 96:2811-6; Moser et al. "Endothelial cell surface Fl-FO ATP synthase is active in ATP synthesis and is inhibited by angiostatin", *Proc Natl Acad Sci USA;* 2001; 98:6656-61). Cariporide can be solubilized in sterile water and sterile filtered.

Cell Culture.

A549 (human epithelial cell line derived from a lung carcinoma tissue), or an alternative cancer cell line (DU145, LNCaP, or PC-3 cells) can be obtained from, for example, the ATCC. Human umbilical vein endothelial cells (HUVEC) can be isolated from human umbilical veins as described. (Grant et al., "Matrigel induces thymosin h 4 gene in differentiating endothelial cells", *J Cell Sci* 1995; 108: 3685-94.). HUVEC cells can be used as a positive control as a cell line that express ATP synthase on the cell surface. Cells can be cultured in DMEM (Life Technologies, Carlsbad, Calif.) with 1% penicillin streptomycin and 10% serum replacement medium 3 (Sigma, St. Louis, Mo.) to minimize the presence of plasminogen. Low-pH (6.7) medium can be prepared by reducing bicarbonate to 10 mmol/L at 5% $CO_2$ and supplementing with 34 mmol/L NaCl to maintain osmolality or incubation of 22 mmol/L bicarbonate medium under 17% $CO_2$ conditions. The method of lowering pH used can be varied by experimental constraints and assay.

Flow Cytometry.

To assure ATP synthase is functional on the cell surface of the tumor cell line, flow cytometry experiments can be performed. For example, A549 Cell lines can be cultured in varying pH medium (10, 22, and 44 mmol/L bicarbonate DMEM), under hypoxia (0.5% 02, 5% $CO_2$, $N_2$ balanced) versus normoxia (21% $O_2$, 5% $CO_2$) for 0, 12, 24, 48, and 72 hours. Live cells can be blocked, incubated with anti-β-subunit antibody, washed, blocked, incubated with a secondary goat anti-rabbit antibody-FITC (Southern Biotech, Birmingham, Ala.), and again washed, with all steps performed at 4 degrees C. Propidium iodide (BD Biosciences, San Jose, Calif.) can be included with all samples to discriminate cells with compromised membranes. The mean fluorescent intensity of FITC in 10,000 cells can be quantified by FACSCalibur flow cytometer (Becton Dickinson, Franklin Lakes, N.J.) and cells with propidium iodide uptake can be excluded to eliminate detection of mitochondrial ATP synthase on CELLQuest software (BD Biosciences).

Cell Surface ATP Generation Assay.

A549 or 1-LN cells (60,000 per well) in 96-well plates can be refreshed with medium and treated with angiostatin, angiosatain variant, anti-beta-subunit antibody, rabbit IgG raised to bovine serum albumin (Organon Teknika, West Chester, Pa.), piceatannol (a known inhibitor of ATP synthase F1 used as a positive control, Sigma), or medium alone for 30 minutes at 37 degrees C., 5% $CO_2$. Cells can be then incubated with 0.05 mmol/L ADP for 20 seconds. Supernatants can be removed and assayed for ATP production by CellTiterGlo luminescence assay (Promega, Madison, Wis.) as described (23). Cell lysates can be similarly analyzed to confirm that intracellular pools of ATP did not vary under any conditions. Recordings can be made on the Luminoskan Ascent (Thermo Labsystems, Helsinki, Finland). Data are expressed in moles of ATP per cell based on standards determined for each independent experiment.

Cell Proliferation Assay.

The effect of angiostatin on cancer cell lines can be assessed with a 3-(4,5-dimethylthiazol-2-yl)-5-(3-carboxymethoxyphenyl)-2-(4-sulfophenyl)-2H-tetrazolium, inner salt (MTS) proliferation assay in serum-free medium. Relative cell numbers in each well of a 96-well microplate after incubation for 20 hours, 37 degrees C., and 5% $CO_2$ in the presence or absence of angiostatin can be determined using the AQueous One Cell Proliferation Assay (Promega) per protocol of the manufacturer. Medium pH can be regulated at 5% $CO_2$ through bicarbonate concentration.

Assessment of Cellular Cytotoxicity.

To quantify cell death and cell lysis, the activity of lactate dehydrogenase (LDH) released from the cytosol into supernatant can be measured with the Cytotoxicity Detection kit (Roche, Indianapolis, Ind.). Cancer cells (e.g. A549 cells) (5,000 per well) treated with angiostatin, angiostatin variant, anti-beta-subunit antibody, rabbit IgG, cariporide, and Triton X (a detergent used to permeabilize cells as a positive control) can be incubated at 37 degrees C. and 5% $CO_2$ or 17% $CO_2$ for 15 hours at neutral and low pH conditions, respectively. An index of cytotoxicity can be calculated by dividing the average absorbance from treated samples in quadruplicate by the average absorbance from untreated samples in quadruplicate corresponding to the same pH medium. Assessment of cellular necrosis and apoptosis. To determine the mode of angiostatin induced cell death a histone-DNA ELISA can be performed. The effects of angiostatin, angiostatin variants, anti-beta-subunit antibody, rabbit IgG, and cariporide on A549 cells (5,000 per well) can be determined using an ELISA apoptosis and necrosis assay (Roche) that is dependent on detection of extranuclear histone-DNA fragments. Apoptosis or necrosis can be determined from, respectively, the cell lysates or supernatants of quadruplicate samples after 15 hours of incubation at 37 degrees C., in the presence or absence of agents. The apoptotic or necrotic indices can be calculated by dividing the average absorbance from treated samples in quadruplicate by the average absorbance from untreated samples in quadruplicate corresponding to the same pH medium. Medium pH can be regulated by incubation at 5% $CO_2$ or 17% $CO_2$.

Intracellular pH (pHi) Measurement.

pHi can be measured by fluorescence in cells plated on 35-mm microwell dishes with glass coverslips (MatTek, Ashland, Mass.). Cells can be plated on growth factor-reduced, phenol-red free Matrigel (BD Biosciences). After overnight growth, medium can be changed and cells can be loaded with the pH-sensitive fluorescent dye cSNARF (Molecular Probes, Eugene, Oreg.) for 15 minutes followed by 20 minutes recovery in fresh medium. Cells can then be mounted on a microscope stage at 37 degrees C., 5% $CO_2$ for 1 hour-long collection of emission spectra from which pHi can be calculated as described from fields containing between 7 and 15 cells each (Wahl M L, Grant D S. "Effects of microenvironmental extracellular pH and extracellular matrix proteins on angiostatin's activity and on intracellular pH", *Gen Pharmacol* 2002; 35:277-85). At the start of spectra collection, medium can be removed from the dish and cells can be challenged with 1 mL of fresh medium in the presence or absence of pH inhibitors angiostatin, anti-beta-subunit, rabbit IgG, or cariporide, a sodium-proton exchange inhibitor. Medium pH can be regulated by bicarbonate concentration, as described above, with fixed % $CO_2$.

Example 6. Generation and Screening of an Fc Codon Variant Library for Optimal Antibody Expression The present example provides methods for generating a Fc codon variant library and screening methods for obtaining Fc variants optimized for improved expression in production host cells as compared to the parental form of Fc polypeptide.

Design and Construction of a Fc Codon Variant Library

For each codon in the target area (in this case the Fc part of the human IgG1 molecule) a pair of degenerate primers (forward and reverse) is designed that includes the target codon and 20 bases on each side. The $3^{rd}$ position of the target codon (wobble position) contains mixed bases (Table 2) that allow the generation of all silent mutations at the target position using the same codon (example A). A second set of degenerate primers is designed for the same codon position if the corresponding amino acid can be encoded by another codon (example B). Corresponding forward and reverse degenerate primers are mixed 1:1, annealed to the template and extended to full length products by strand displacement using a thermostable DNA polymerase. The template is digested with DpnI and full length extension products are transformed into *E. coli*. Up to 12 colonies per mutagenesis reaction are sequenced. Sequence confirmed mutants are arrayed in 96 well plates and glycerol stocked.

The glycerol stocks are used to miniprep plasmid DNA for transfection into mammalian cells and screening.

TABLE 2

Codes for degenerate bases in synthetic oligos

| Symbol | Mixed Base |
|---|---|
| R | A, G |
| Y | C, T |
| M | A, C |
| K | G, T |
| S | C, G |
| W | A, T |
| H | A, C, T |
| B | C, G, T |
| V | A, C, G |
| D | A, G, T |
| N | A, C, G, T |

Example A: target codon=CCC (proline)
→forward primer: CCD, reverse primer: HGG
Example B; target codon=TCG (serine)
→forward primer1: TCH, reverse primer1: DGA
→forward primer2: AGY, reverse primer2: RCT
20 bases flanking the target codon are not shown. Total primer length: 43 bases.

Expression and ELISA Based Screening of Fc Codon Variant Library

Clones from the Fc codon variant library were transfected into a mammalian cell line. Full length IgGs were produced and secreted into the medium. Supernatants of expressed Fc codon variants were screened for an IgG expression level higher than the parental clone using an ELISA assay. The ELISA data was normalized with a beta-galactosidase assay by measuring the transfection efficiency. Top hits identified in the primary screen were re-transfected and re-screened three times to confirm the increased expression level.

Example 7: Generation of scFv Conditionally Active Antibodies

Figure 2:
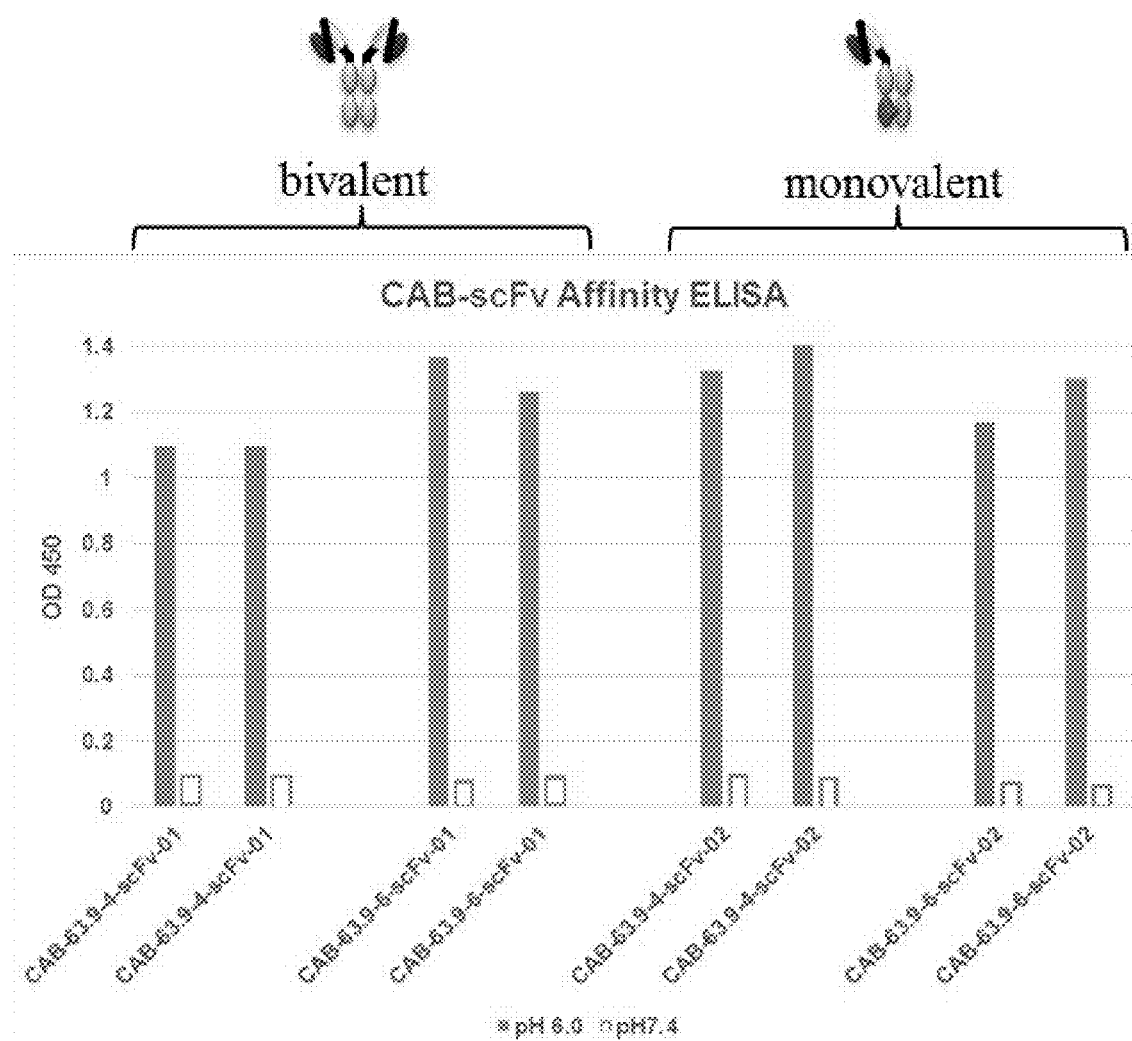
FIGS. 2 and 3 show that expressing the conditionally active antibodies of Example 7 as bivalent or monovalent antibodies does not significantly alter that selectivity of these antibodies under pH 6.0 and over pH 7.4.
Figure 3:
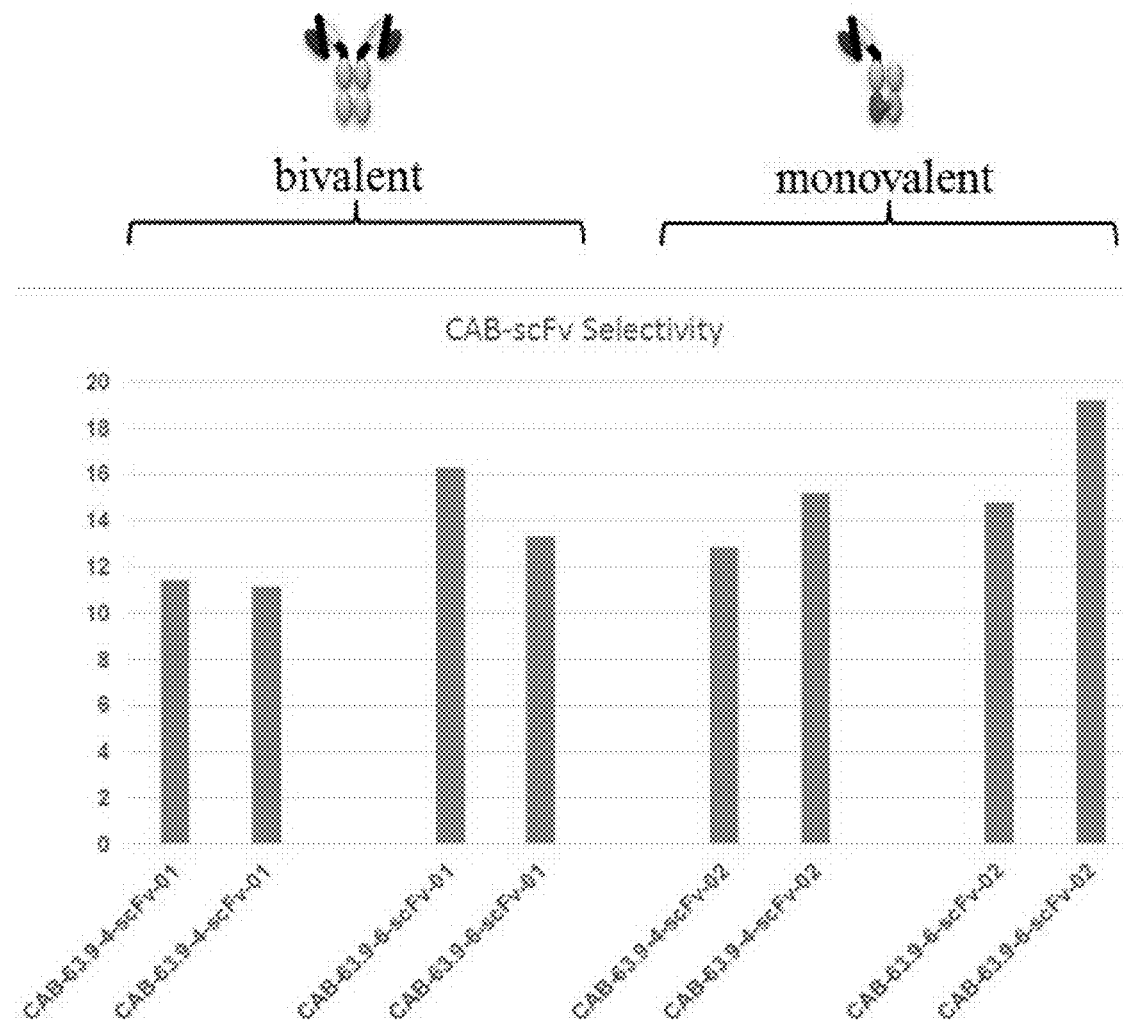

Two conditionally active antibodies (CAB-scFv-63.9-4 and CAB-scFv-63.9-6) for a drug target X were expressed as homodimers with wild type human IgG1 Fc (resulting in bivalent antibodies CAB-scFv-63.9-4-01 and CAB-scFv-63.9-6-01 in FIGS. 2-3), as well as heterodimers in the knob-in-hole system resulting in a monovalent scFv (resulting in monovalent antibodies scFv CAB-scFv-63.9-4-02 and CAB-scFv-63.9-6-02 in FIGS. 2-3).

The binding affinities of these antibodies to the drug target X at pH 6.0 and pH 7.4 were measured by the ELISA assay. As show in FIG. 2, the scFv antibodies showed affinities to drug target X at both pH 6.0 and pH 7.4, which were comparable to the full bivalent antibodies. Further, the selectivity of these scFv antibodies at pH 6.0 over pH 7.4 as shown in FIG. 3 was also comparable to the full bivalent antibodies. This example demonstrated that the conditionally active antibodies of the present invention have comparable affinity and selectivity either as scFv antibodies or full bivalent antibodies. Thus, the conditionally active antibodies of the present invention may be inserted as a single DNA chain in a DNA molecule that encodes CAR in the CAR-T platform of the present invention.

Example 8: Expression of Conditionally Active Antibodies

Conditionally active antibodies for the drug target X were generated by simultaneously screening for selectivity and affinity, as well as expression level at both pH 6.0 and pH 7.4, in accordance with one embodiment of the present invention. The screening was done in serum using a FLAG tag because there were human antibodies in the serum which might cause false positives for the screening. The screening buffer was a carbonate buffer (krebs buffer with ringer-standard buffer but different from PBS). The generated conditionally active antibodies were found to have a higher affinity to the drug target X at pH 6.0 but lower affinity to the same drug target X at pH 7.4, both in comparison with the wild-type antibody. Further, these conditionally active antibodies all have high expression levels as shown in Table 3 below, with column "Clone" showing the antibodies and the expression level "mg/ml" being shown in the second column.

The clones of these antibodies were sent to a service provider with a requested expression level ("amount ordered", expected expression levels). However, the actual expression levels of these antibodies ("amount delivered") were very high and exceeded the expected expression levels.

TABLE 3

Conditionally active antibodies with high expression levels

| Clone | mg/ml | amount ordered | amount delivered |
|---|---|---|---|
| BAP063.6-hum10F10-FLAG | 7 | 150 | 294 |
| BAP063.6-HC-H100Y-FLAG | 6.6 | 150 | 238 |
| BAP063.8-LC046HC04-FLAG | 7 | 200 | 332.5 |
| BAP063.8-LC062HC02-FLAG | 5.8 | 200 | 220.4 |
| BAP063.9-13-1-FLAG | 5.3 | 50 | 123 |
| BAP063.9-29-2-FLAG | 4.9 | 50 | 102 |
| BAP063.9-45-2-FLAG | 5.4 | 50 | 129 |
| BAP063.9-13-3-FLAG | 5.9 | 50 | 130 |
| BAP063.9-21-3-FLAG | 5.3 | 50 | 117 |
| BAP063.9-21-4-FLAG | 7 | 50 | 176 |
| BAP063.9-29-4-FLAG | 8.2 | 50 | 196 |
| BAP063.9-48-3-FLAG | 7 | 50 | 125 |
| BAP063.9-49-4-FLAG | 5.3 | 50 | 126 |
| BAP063.9-61-1-FLAG | 5.1 | 50 | 97 |
| BAP063.9-61-2-FLAG | 5 | 50 | 92 |

Figure 4:
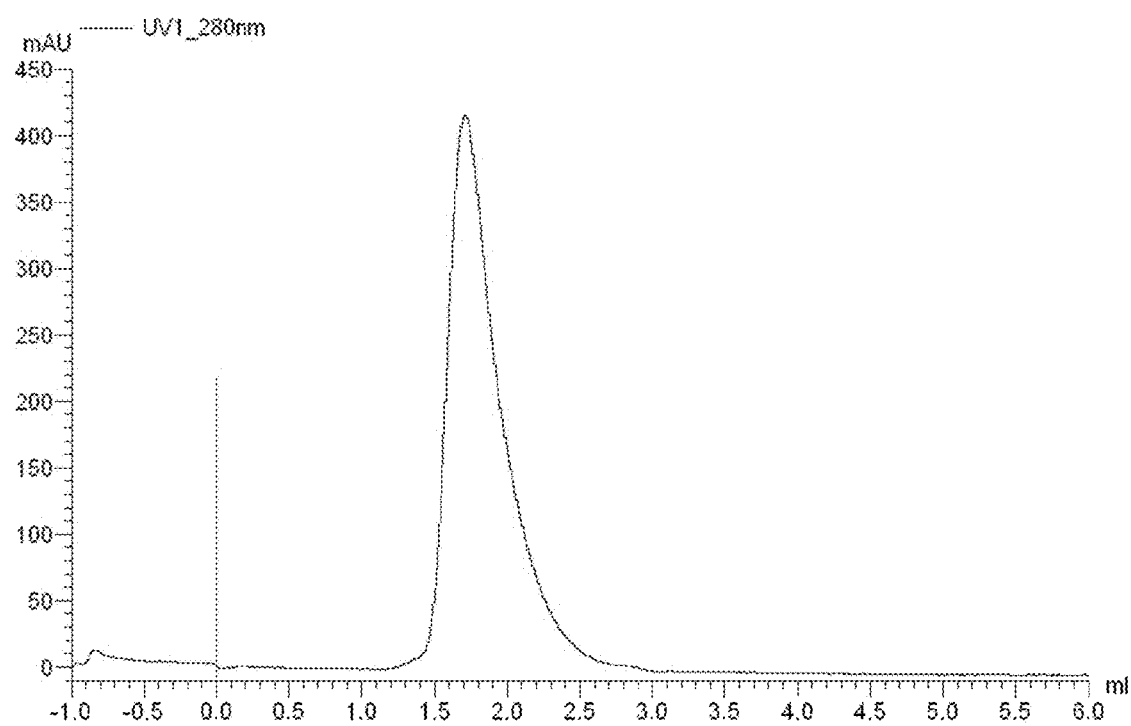
FIG. 4 is a profile of a size exclusive chromatograph indicating that the conditionally active antibodies of Example 8 do not aggregate.

The conditionally active antibodies did not show aggregation in a buffer as demonstrated in FIG. 4, using BAP063.9-13-1 antibody as an example. The BAP063.9-13-1 antibody was analyzed by size exclusion chromatography. In FIG. 4, only one peak was detected, demonstrating little or no aggregation of the antibody.

The conditionally active antibodies were also assayed using surface plasmon resonance (SPR) to measure their on and off rates to the drug target X. The SPR assay has been known to measure on and off rates for the conditionally active antibodies. The SPR assay was performed in the presence of bicarbonate. The in vivo on and off rate (in animals and humans) of the conditionally active antibodies is a very important feature for the conditionally active antibodies.

Figure 5:
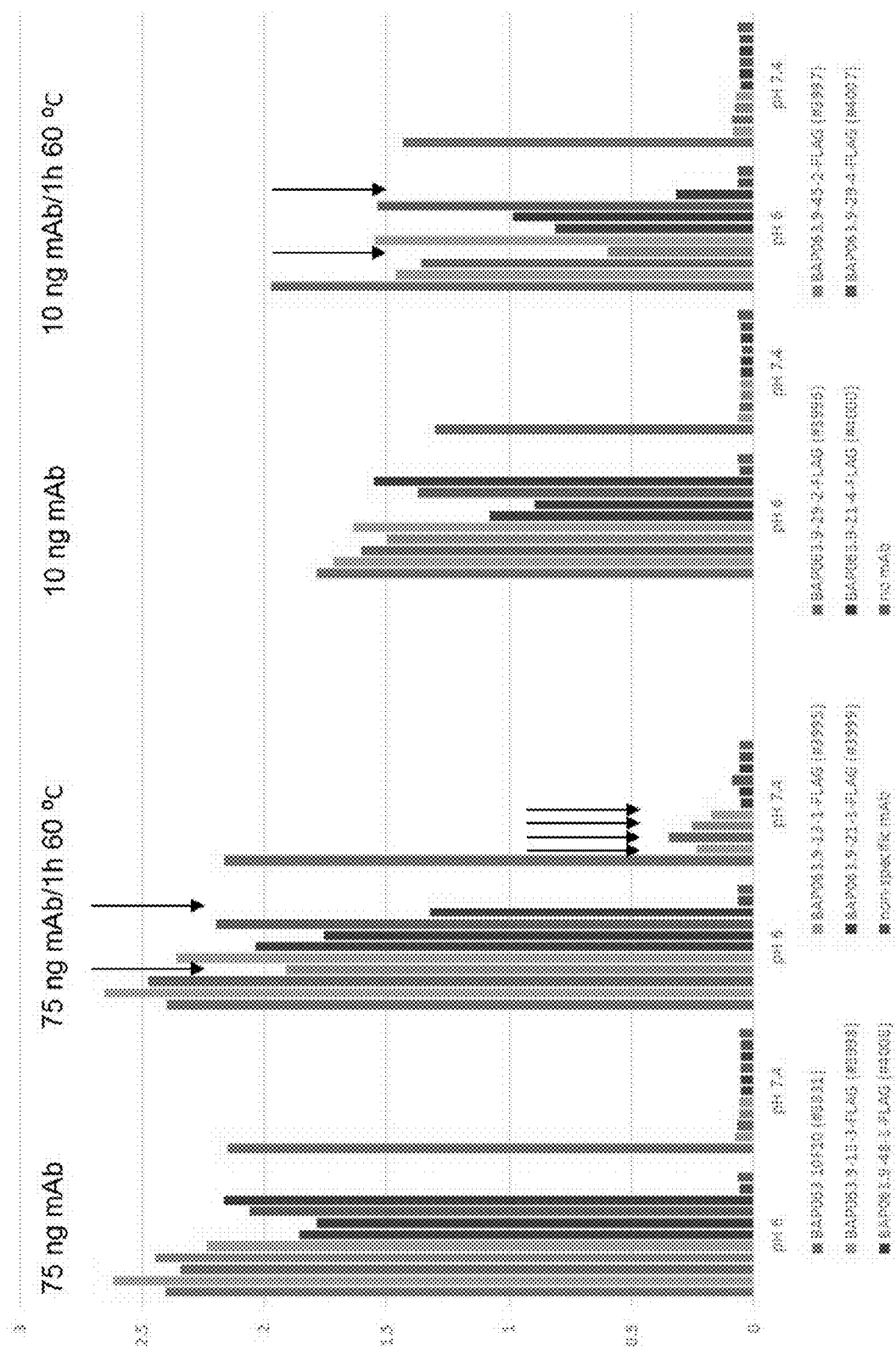
FIG. 5 shows on and off rates for the conditionally active antibodies of Example 8 as measured by a surface plasmon resonance (SPR) assay.
Figure 6A:
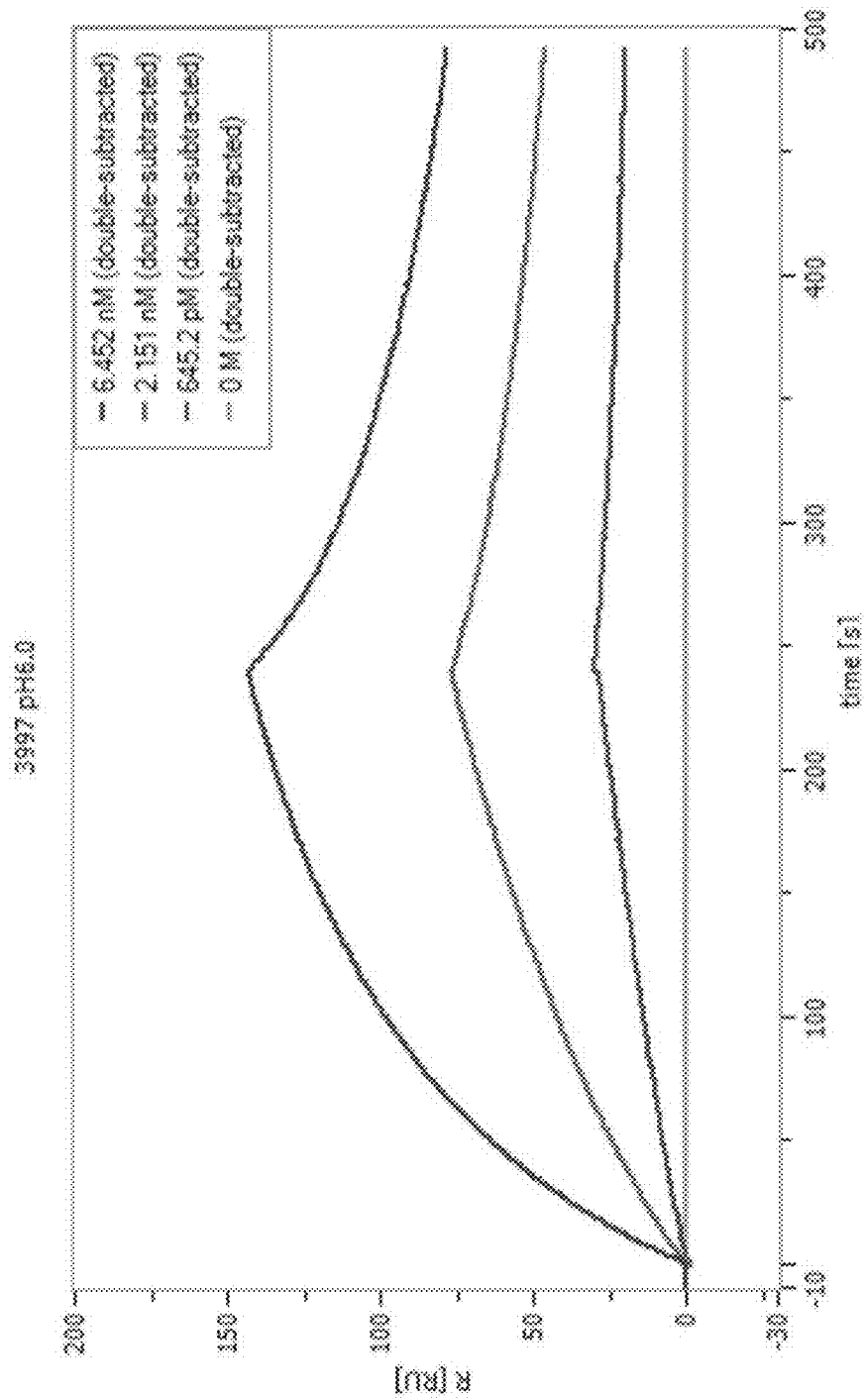
FIGS. 6A-6B show the selectivity of the conditionally active antibodies as measured by the SPR assay of Example 8.
Figure 6B:
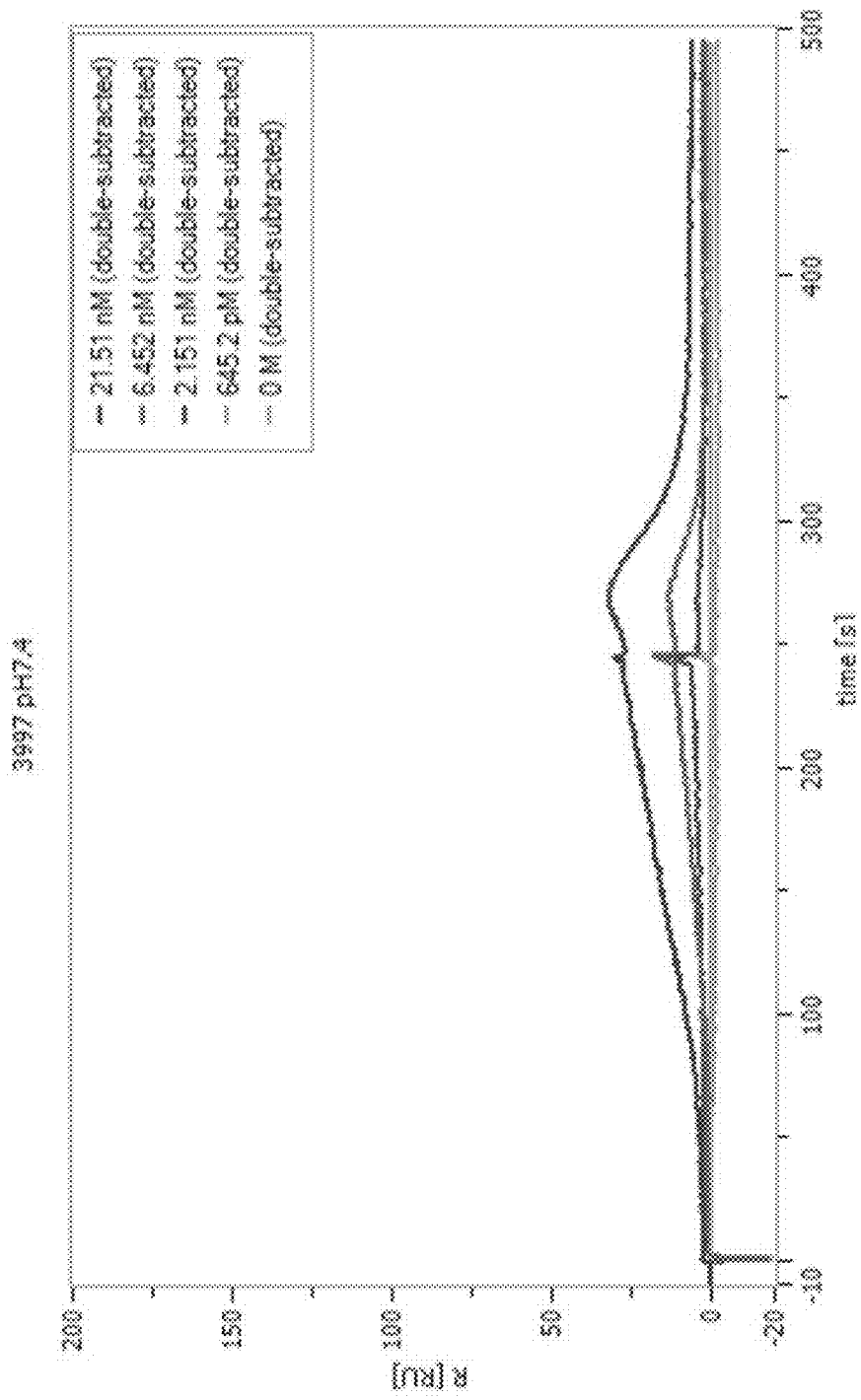

It was observed that the conditionally active antibodies have quick on-rates at pH 6.0 and slower on-rates at pH 7.4, in comparison with the negative control (BAP063 10F10 which has similar on-rates at both pH 6.0 and pH 7.4) (FIG. 5). In addition, raising the temperature from room temperature to 60° C. does not significantly alter the SPR assay results (FIG. 5). The SPR assay also showed that these conditionally active antibodies were highly selective at pH 6.0 as compared to pH 7.4 (FIGS. 6A-6B show one antibody as an example).

The conditionally active biologic antibodies are summarized in Table 4. Two of the antibodies were expressed as scFv (BAP063.9-13.3 and BAP063.9-48.3). Incubating the antibodies at 60° C. for one hour did not change the affinities of most of the antibodies ("Thermostability"). In the two columns reporting data using SPR to measure binding activity at pH 6.0 and pH 7.4 (the last two columns of Table 4), a comparison was made to "BAP063.6-hum10F10-FLAG" (a negative control, second row in Table 4). The selectivity of these antibodies may be determined by the differences between the data in the two last columns. The two scFv antibodies had very high selectivity (75% and 50% at pH 6 over 0% at pH 7.4).

its activity at pH 7.4. In addition, many of the conditionally active antibodies had an activity that was reversible at a pH between the normal physiologic pH of 7.4 and the aberrant pH of 6.0. Interestingly, most of the conditionally active antibodies generated from this example exhibited optimal binding activity at a pH of about 5.5 to 6.5, when the activity of the conditionally active antibodies was tested in the pH range of 5.0 to 7.4 by the ELISA assay.

The activity of the conditionally active antibodies generated by this example was also confirmed by a FACS (Fluorescence-activated cell sorting) assay using whole cells, where CHO cells were used to express the antigen of the antibodies at pH 6.0 and pH 7.4. The conditionally active antibodies were added to CHO cells in order to measure the binding activity. The FACS assay confirmed the general

TABLE 4

Summary of the conditionally active antibodies

| Clone | CAB scFv | mg/ml | Aggregation (PBS, pH 7.4) | Thermo-stability (1 h 60° C.) | Increased binding at pH 7.4 after heat treatment | Ka [M · s] | Kd[$s^{-1}$] | KD[M] pH 6.0 | SPR activity pH 6.0 | SPR activity pH 7.4 |
|---|---|---|---|---|---|---|---|---|---|---|
| BAP063.6-hum10F10-FLAG | | 7 | No | 100% | No | 5.14E+06 | 8.38E−04 | 1.63E−10 | 100% | 100% |
| BAP063.6-HC-H100Y-FLAG | | 6.6 | N.D. | | | 2.41E+06 | 5.12E−03 | 2.12E−09 | 80% | 40% |
| BAP063.9-13-1-FLAG | | 5.3 | No | 100% | Yes | 1.98E+06 | 2.88E−03 | 1.46E−09 | 100% | 75% |
| BAP063.9-29-2-FLAG | | 4.9 | No | 100% | Yes | 1.19E+06 | 2.14E−03 | 1.79E−09 | 90% | 50% |
| BAP063.9-45-2-FLAG | | 5.4 | No | Reduced | Yes | 1.53E+06 | 2.31E−03 | 1.51E−09 | 75% | 25% |
| BAP063.9-13-3-FLAG | Yes | 5.9 | No | 100% | Yes | 1.42E+06 | 1.82E−03 | 1.28E−09 | 75% | 0% |
| BAP063.9-21-3-FLAG | | 5.3 | No | 100% | No | 1.53E+06 | 4.13E−03 | 2.69E−09 | 50% | 25% |
| BAP063.9-21-4-FLAG | | 7 | No | 100% | No | 1.03E+06 | 3.26E−03 | 3.16E−09 | 50% | 0% |
| BAP063.9-29-4-FLAG | | 8.2 | No | 100% | (yes) | 1.40E+06 | 2.21E−03 | 1.58E−09 | 75% | 0% |
| BAP063-9-48-3-FLAG | Yes | 7 | <5% | reduced | No | 8.92E+05 | 2.33E−03 | 2.61E−09 | 50% | 0% |

Example 9: Evolving a Light Chain or a Heavy Chain of an Antibody

The heavy chain and light chain of an antibody F1-10F10 were separately evolved using CPE. The light chain mutants were screened to discover 26 light chain mutants with conditional activity, in this case the mutants were more active at pH 6.0 than the wild-type and the mutants less active at pH 7.4 than the wild-type. The 26 light chain mutants had their mutations at 8 different positions in the light chain. 3 of the 8 positions appeared in more than 5 of the 26 light chain mutants. These 3 positions were deemed to be hot spots in the light chain. The heavy chain mutants were screened to discover 28 heavy chain mutants with conditional activity. The 28 heavy chain mutants had their mutations at 8 different positions in the heavy chain. 3 of the 8 positions appeared in more than 5 of the 28 heavy chain mutants. These 3 positions were deemed to be hot spots in the heavy chain. The conditional activity of the light chain mutants and heavy chain mutants was confirmed by an ELISA assay.

The best conditionally active antibody generated by this example had a 17-fold difference in its activity at pH 6.0 to trend in the results of the ELISA assay for the selectivity of the conditionally active antibodies at pH 6.0 relative to pH 7.4.

Example 10: Selecting Conditionally Active Antibodies in a Special Buffer

Mutant antibodies generated by an evolving step in accordance with the present invention were subjected to an assay at a normal physiologic pH of 7.4 and to an assay at an aberrant pH of 6.0. Both assays were performed using a phosphate buffered saline (PBS) solution including a bicarbonate found in human serum. The concentration of Bicarbonate in the solution was a typical concentration of Bicarbonate in a human serum, i.e. a physiological concentration. A comparative test was done using the same PBS solution without bicarbonate.

The assay for measuring the binding activity for the mutant antibodies or conditionally active antibodies in this example was an ELISA assay. It was found that the assays in the PBS buffer solution containing bicarbonate resulted in a significantly higher success rate for the selection of conditionally active antibodies. In addition, the conditionally active antibodies selected using the PBS buffer solution containing bicarbonate tended to have much higher ratio of their activity at pH 6.0 to the activity at pH 7.4 thereby providing a significantly higher selectivity.

It was further observed that when the selected conditionally active antibodies (using PBS buffer solution with bicarbonate were tested in the PBS buffer solution without bicarbonate, the selectivity of the conditionally active antibodies at pH 6.0 relative to pH 7.0 was significantly reduced. However, when bicarbonate was added to this PBS buffer solution in a physiological amount, the selectivity of the same conditionally active antibodies was restored.

In another assay, the selected conditionally active antibodies were tested in a Krebs buffer solution with added bicarbonate. The higher ratio of the activity at pH 6.0 to the activity at pH 7.4 was also observed in this Krebs buffer solution with added bicarbonate. It appears that this may have been at least partly due to the presence of bicarbonate in the Krebs buffer solution.

When the concentration of bicarbonate was reduced in the PBS buffer solution to concentrations below its physiological concentration, it was observed that the activity of the conditionally active antibody at the normal physiological pH of 7.4 was increased. The increase in the activity of the conditionally active antibody at pH 7.4 was observed to be related to the decrease in the concentration of bicarbonate in the PBS buffer solution.

The wild-type antibody was not affected by the different amounts of bicarbonate in the PBS buffer solution when assayed at pH 7.4 as its activity remained the same at all the same concentrations of bicarbonate in the PBS buffer solution that were tested for the conditionally active antibody.

Example 11: Selecting Conditionally Active Antibodies in Different Buffers

The mutant antibodies generated by an evolving step according to the present invention were subjected to an ELISA assay at a normal physiologic pH (7.4) and an ELISA assay at an aberrant pH (6.0). Both ELISA assays were performed using different buffers, including buffers based on Krebs buffer with bovine serum albumin (BSA), and buffers based on PBS buffer with bicarbonate and BSA.

The conditionally active antibodies selected using assays in the PBS buffer solution with bicarbonate exhibited a much higher ratio of the activity at pH 6.0 to the activity at pH 7.4, in comparison with those selected using an assay in PBS buffer solution without bicarbonate. In addition, the Krebs buffer solution with added bicarbonate also provided a higher ratio of the activity at pH 6.0 to the activity at pH 7.4 when comparison with the assay in PBS buffer solution without bicarbonate. It appears the bicarbonate is important to the selection of desirable conditionally active antibodies.

All documents mentioned herein are hereby incorporated by reference in their entirety or alternatively to provide the disclosure for which they were specifically relied upon.

It must be noted that as used herein and in the appended claims, the singular forms "a", "an", and "the" include plural references unless the context clearly dictates otherwise. Furthermore, the terms "a" (or "an"), "one or more," and "at least one" can be used interchangeably herein. The terms "comprising," "including," "having," and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent or parameter disclosed herein is to be interpreted as being disclosed for use alone or in combination with one or more of each and every other component, compound, substituent or parameter disclosed herein.

It is also to be understood that each amount/value or range of amounts/values for each component, compound, substituent or parameter disclosed herein is to be interpreted as also being disclosed in combination with each amount/value or range of amounts/values disclosed for any other component(s), compounds(s), substituent(s) or parameter(s) disclosed herein and that any combination of amounts/values or ranges of amounts/values for two or more component(s), compounds(s), substituent(s) or parameters disclosed herein are thus also disclosed in combination with each other for the purposes of this description.

It is further understood that each range disclosed herein is to be interpreted as a disclosure of each specific value within the disclosed range that has the same number of significant digits. Thus, a range of from 1-4 is to be interpreted as an express disclosure of the values 1, 2, 3 and 4. It is further understood that each lower limit of each range disclosed herein is to be interpreted as disclosed in combination with each upper limit of each range and each specific value within each range disclosed herein for the same component, compounds, substituent or parameter. Thus, this disclosure is to be interpreted as a disclosure of all ranges derived by combining each lower limit of each range with each upper limit of each range or with each specific value within each range, or by combining each upper limit of each range with each specific value within each range.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A method of producing a conditionally active biologic protein, the method comprising:
   (i) selecting a wild-type biologic protein;
   (ii) evolving DNA which encodes the wild-type biologic protein using one or more evolutionary techniques to create mutant DNAs;
   (iii) expressing the mutant DNAs in a mammalian cell production host to obtain mutant proteins;
   (iv) subjecting the mutant proteins and the wild-type protein to an assay under a normal physiological condition and to an assay under an aberrant condition;
   (v) selecting a conditionally active biologic protein from the mutant proteins expressed in step (iii) which exhibit a decrease in activity in the assay at the normal physiological condition compared to a same activity in the assay under the aberrant condition; and
   (vi) producing the conditionally active biologic protein in the same mammalian cell production host as used in step (iii).

2. The method of claim 1 wherein the conditionally active biologic protein exhibits both (a) a decrease in activity in the assay at the normal physiological condition compared to the wild-type protein, and (b) an increase in activity in the assay under the aberrant condition compared to the wild-type protein.

3. The method of claim 1, wherein the wild-type biologic protein is an antibody.

4. The method of claim 3, further comprising the step of conjugating the conditionally active antibody to a molecule selected from cytokines, interleukins, enzymes, hormones, growth factors, cytotoxic agents, chemotherapy drugs, radioactive particles and diagnostic agents.

5. The method of claim 4, wherein the conjugating comprises forming a covalent bond between the conditionally active antibody and the molecule.

6. The method of claim 4, wherein the conjugating comprises forming a non-covalent bond between the conditionally active antibody and the molecule.

7. The method of claim 4, wherein the molecule is conjugated to the Fc region of the conditionally active antibody.

8. The method of claim 3, further comprising the step of engineering the conditionally active antibody to be multispecific, said multispecific antibody having binding affinities for at least two different epitopes.

9. The method of claim 8, wherein the at least two different epitopes are located on at least two antigens.

10. The method of claim 1, wherein the wild-type biologic protein is selected from tissue plasminogen activator, streptokinase, urokinase, renin, and hyaluronidase.

11. The method of claim 1, wherein the wild-type biologic protein is selected from calcitonin gene-related peptide, substance P, neuropeptide Y, vasoactive intestinal peptide, vasopressin, angiostatin, a protein that binds with a target protein on a target cell, and a DNA/RNA modifying protein.

12. The method of claim 1, wherein the normal physiological condition is selected from one or more of normal physiological temperature, pH, osmotic pressure, osmolality, oxidative stress and electrolyte concentration.

13. The method of claim 12, wherein the normal physiological condition is temperature; and wherein the conditionally active biologic protein is substantially inactive at the normal physiological temperature, and is active at an aberrant temperature less than the normal physiological temperature.

14. The method of claim 1, wherein the evolving step comprises a technique selected from the group consisting of PCR, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis, in vitro mutagenesis, ligase chain reaction, oligonucleotide synthesis and combination thereof.

15. The method of claim 1, wherein the mammalian cell production host is selected from Bowes melanoma cells, COS-7 cells, C127 cells, HeLa cells, BHK cells, 3T3 mouse fibroblast cells, BHK21 Syrian hamster fibroblast cells, MDCK dog epithelial cells, PtK1 rat kangaroo epithelial cells, SP2/0 mouse plasma cells, NS0 mouse plasma cells, HEK 293 human embryonic kidney cells, COS monkey kidney cells, CHO cells, CHO-S, R1 mouse embryonic cells, E14.1 mouse embryonic cells, H1 human embryonic cells, H9 human embryonic cells, and PER C6 human embryonic cells.

16. The method of claim 15, wherein the mammalian cell production host is selected from CHO cells, NS0 mouse plasma cells, and HEK293 human embryonic kidney cells.

17. The method of claim 1, wherein the producing step comprises manufacturing.

18. The method of claim 1, further comprising a step of inserting the conditionally active biologic protein into a viral particle as a recognition protein.

19. The method of claim 1, further comprising a step of integrating the conditionally active biologic protein into a chimeric antigen receptor as an antigen specific targeting region.

20. The method of claim 19, wherein the eukaryotic cell production host is a cytotoxic cell.

21. The method of claim 20, wherein the cytotoxic cell is a T-cell.

22. A conditionally active biologic protein prepared by the method of claim 1, wherein the conditionally active biologic protein is reversibly or irreversibly inactivated at the normal physiological condition.

23. The conditionally active biologic protein of claim 22, wherein the conditionally active biologic protein comprises at least one non-natural amino acid.

24. A chimeric antigen receptor comprising the conditionally active biologic protein of claim 22.

25. A cytotoxic cell comprising the chimeric antigen receptor of claim 24.

* * * * *

UNITED STATES PATENT AND TRADEMARK OFFICE
CERTIFICATE OF CORRECTION

| | |
|---|---|
| PATENT NO. | : 10,513,699 B2 |
| APPLICATION NO. | : 15/329491 |
| DATED | : December 24, 2019 |
| INVENTOR(S) | : Short |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 133 days.

Signed and Sealed this
First Day of July, 2025

Coke Morgan Stewart
*Acting Director of the United States Patent and Trademark Office*